US011751913B2

(12) United States Patent
Jackson et al.

(10) Patent No.: US 11,751,913 B2
(45) Date of Patent: Sep. 12, 2023

(54) LONGITUDINAL CONNECTING MEMBER WITH SLEEVED TENSIONED CORDS AND RELEASABLE END BLOCKER-BUMPER

(71) Applicant: Roger P. Jackson, Prairie Village, KS (US)

(72) Inventors: Roger P. Jackson, Prairie Village, KS (US); James L. Surber, Kansas City, KS (US)

( * ) Notice: Subject to any disclaimer, the term of this patent is extended or adjusted under 35 U.S.C. 154(b) by 0 days.

(21) Appl. No.: 15/835,216

(22) Filed: Dec. 7, 2017

(65) Prior Publication Data
US 2018/0168693 A1 Jun. 21, 2018

Related U.S. Application Data

(63) Continuation of application No. 12/802,849, filed on Jun. 15, 2010, now abandoned, which is a continuation-in-part of application No. 12/221,442, filed on Aug. 1, 2008, now abandoned, which is a continuation-in-part of application No. 11/328,481, filed on Jan. 9, 2006, now Pat. No. 7,862,587, said application No. 12/802,849 is a continuation-in-part of application No. 12/148,465, filed on Apr. 18, 2008, now Pat. No. 10,258,382.

(60) Provisional application No. 61/268,708, filed on Jun. 15, 2009, provisional application No. 61/270,754, filed on Jul. 13, 2009, provisional application No. 61/336,911, filed on Jan. 28, 2010, provisional
(Continued)

(51) Int. Cl.
*A61B 17/70* (2006.01)
*A61B 17/68* (2006.01)

(52) U.S. Cl.
CPC ............ *A61B 17/702* (2013.01); *A61B 17/68* (2013.01); *A61B 17/7008* (2013.01); *A61B 17/7032* (2013.01); *A61B 17/7037* (2013.01); *A61B 17/7076* (2013.01)

(58) Field of Classification Search
CPC ........................................ A61B 17/7001–7046
See application file for complete search history.

(56) References Cited

U.S. PATENT DOCUMENTS 5,171,279 A 12/1992 Mathews
D346,217 S 4/1994 Sparker et al.
(Continued)

OTHER PUBLICATIONS

U.S. Appl. No. 15/918,181, filed Mar. 12, 2018, Jackson.
U.S. Appl. No. 16/543,235, filed Aug. 16, 2019, Jackson.

*Primary Examiner* — Nicholas J Plionis
(74) *Attorney, Agent, or Firm* — Polsinelli PC

(57) ABSTRACT

A dynamic fixation medical implant having at least two bone anchors includes a longitudinal connecting member assembly having rigid sleeves for attachment to the bone anchors, at least one spacer engaging the bone anchors and the sleeves, and in some embodiments, an end elastic bumper. A flexible cord is initially slidingly received within the rigid sleeves, the spacer and the bumper. The spacer may include an optional inelastic inner liner, with at least one of the sleeves having an extension slidingly receivable within the liner. Some sleeves include apertures for receiving a closure top portion for locking the cord against the sleeve, or alternatively receiving a closure top that does not extend into the aperture, the slip or grip option provided by the aperture in each sleeve resulting in an overall connector with variable segmental stiffness.

24 Claims, 58 Drawing Sheets

Related U.S. Application Data application No. 61/395,564, filed on May 14, 2010, provisional application No. 61/395,752, filed on May 17, 2010, provisional application No. 61/396,390, filed on May 26, 2010, provisional application No. 60/927,111, filed on May 1, 2007.

(56) References Cited

U.S. PATENT DOCUMENTS

| | | |
|---|---|---|
| 5,487,742 A | 1/1996 | Cotrel |
| 5,569,253 A | 10/1996 | Farris et al. |
| 6,132,431 A | 10/2000 | Nilsson et al. |
| 6,248,106 B1 | 6/2001 | Ferree |
| 6,251,112 B1* | 6/2001 | Jackson ............. A61B 17/7032 606/270 |
| 6,280,442 B1 | 8/2001 | Barker et al. |
| 6,290,700 B1 | 9/2001 | Schmotzer |
| 6,565,565 B1 | 5/2003 | Yuan et al. |
| 6,997,927 B2 | 2/2006 | Jackson |
| 7,713,288 B2 | 5/2010 | Timm et al. |
| 7,815,665 B2 | 10/2010 | Jahng et al. |
| 7,828,825 B2 | 11/2010 | Bruneau et al. |
| 7,842,072 B2 | 11/2010 | Dawson |
| 7,901,437 B2 | 3/2011 | Jackson |
| 7,988,710 B2 | 8/2011 | Jahng et al. |
| 8,029,544 B2 | 10/2011 | Hested et al. |
| 8,114,133 B2 | 2/2012 | Logan |
| 8,128,667 B2 | 3/2012 | Jackson |
| 8,157,843 B2 | 4/2012 | Biederman et al. |
| 8,292,926 B2 | 10/2012 | Jackson |
| 8,366,745 B2 | 2/2013 | Jackson |
| 8,465,526 B2 | 6/2013 | Friedrich et al. |
| 9,101,404 B2 | 8/2015 | Jackson |
| 9,439,683 B2 | 9/2016 | Jackson |
| 9,451,989 B2 | 9/2016 | Jackson |
| 9,668,771 B2 | 6/2017 | Jackson |
| 9,750,540 B2 | 9/2017 | Jackson |
| 9,861,394 B2 | 1/2018 | Jackson et al. |
| 9,931,139 B2 | 4/2018 | Jackson |
| 9,956,002 B2 | 5/2018 | Jackson |
| 10,130,393 B2 | 11/2018 | Jackson |
| 2002/0035366 A1 | 3/2002 | Walder et al. |
| 2002/0055740 A1 | 5/2002 | Lieberman |
| 2002/0107570 A1 | 8/2002 | Sybert et al. |
| 2002/0116001 A1 | 8/2002 | Schafer |
| 2002/0116065 A1 | 8/2002 | Jackson |
| 2002/0198526 A1 | 12/2002 | Shaolian et al. |
| 2003/0083657 A1 | 5/2003 | Drewry et al. |
| 2003/0212398 A1* | 11/2003 | Jackson ............. A61B 17/7049 606/300 |
| 2004/0049190 A1 | 3/2004 | Biederman et al. |
| 2004/0138662 A1 | 7/2004 | Landry et al. |
| 2004/0143265 A1 | 7/2004 | Landry et al. |
| 2004/0167523 A1 | 8/2004 | Jackson |
| 2004/0172032 A1 | 9/2004 | Jackson |
| 2004/0215191 A1 | 10/2004 | Kitchen |
| 2004/0236327 A1 | 11/2004 | Paul et al. |
| 2004/0236328 A1 | 11/2004 | Paul et al. |
| 2005/0010220 A1 | 1/2005 | Casutt et al. |
| 2005/0085815 A1 | 4/2005 | Harms et al. |
| 2005/0131407 A1 | 6/2005 | Sicvol et al. |
| 2005/0149020 A1 | 7/2005 | Jahng |
| 2005/0203514 A1 | 9/2005 | Jahng et al. |
| 2005/0203517 A1 | 9/2005 | Jahng et al. |
| 2005/0261685 A1 | 11/2005 | Fortin |
| 2005/0277919 A1 | 12/2005 | Slivka et al. |
| 2005/0277920 A1* | 12/2005 | Slivka ................ A61B 17/7022 606/263 |
| 2005/0277922 A1 | 12/2005 | Trieu et al. |
| 2005/0277932 A1 | 12/2005 | Farris |
| 2005/0288671 A1 | 12/2005 | Yuan et al. |
| 2005/0288672 A1 | 12/2005 | Ferree |
| 2006/0025767 A1 | 2/2006 | Khalili |
| 2006/0036240 A1 | 2/2006 | Colleran et al. |
| 2006/0058788 A1 | 3/2006 | Hammer et al. |
| 2006/0064090 A1 | 3/2006 | Park |
| 2006/0079894 A1* | 4/2006 | Colleran ................ A61B 5/103 606/86 A |
| 2006/0142760 A1 | 6/2006 | McDonnell |
| 2006/0149238 A1 | 7/2006 | Sherman et al. |
| 2006/0241602 A1* | 10/2006 | Jackson ............. A61B 17/7049 606/251 |
| 2006/0241769 A1 | 10/2006 | Gordon et al. |
| 2006/0247635 A1 | 11/2006 | Gordon et al. |
| 2006/0247779 A1 | 11/2006 | Gordon et al. |
| 2006/0264937 A1 | 11/2006 | White |
| 2007/0005063 A1 | 1/2007 | Bruneau et al. |
| 2007/0032123 A1 | 2/2007 | Timm et al. |
| 2007/0100341 A1 | 5/2007 | Reglos et al. |
| 2007/0118123 A1 | 5/2007 | Strausbaugh et al. |
| 2007/0123864 A1 | 5/2007 | Walder et al. |
| 2007/0129729 A1 | 6/2007 | Petit et al. |
| 2007/0191841 A1 | 8/2007 | Justis et al. |
| 2007/0233064 A1 | 10/2007 | Holt |
| 2007/0233075 A1 | 10/2007 | Dawson |
| 2007/0270821 A1 | 11/2007 | Trieu et al. |
| 2007/0270840 A1 | 11/2007 | Chin et al. |
| 2007/0276380 A1 | 11/2007 | Jahng et al. |
| 2007/0288011 A1 | 12/2007 | Logan |
| 2008/0021469 A1 | 1/2008 | Holt |
| 2008/0051787 A1 | 2/2008 | Remington et al. |
| 2008/0058812 A1 | 3/2008 | Zehnder |
| 2008/0086125 A1 | 4/2008 | Molz et al. |
| 2008/0086130 A1 | 4/2008 | Lake |
| 2008/0161857 A1 | 7/2008 | Hestad et al. |
| 2008/0183213 A1* | 7/2008 | Veldman ............ A61B 17/7008 606/257 |
| 2008/0234691 A1 | 9/2008 | Schwab |
| 2008/0234737 A1* | 9/2008 | Boschert ............ A61B 17/7031 606/254 |
| 2008/0234744 A1 | 9/2008 | Zylber et al. |
| 2008/0262551 A1 | 10/2008 | Rice et al. |
| 2008/0262553 A1 | 10/2008 | Hawkins et al. |
| 2008/0275504 A1* | 11/2008 | Bonin ................. A61B 17/702 606/246 |
| 2008/0294198 A1 | 11/2008 | Jackson |
| 2008/0319482 A1 | 12/2008 | Jackson |
| 2008/0319486 A1 | 12/2008 | Hestad et al. |
| 2009/0005817 A1 | 1/2009 | Friedrich et al. |
| 2009/0012562 A1 | 1/2009 | Hestad et al. |
| 2009/0036924 A1 | 2/2009 | Egli et al. |
| 2009/0054932 A1 | 2/2009 | Butler et al. |
| 2009/0082815 A1 | 3/2009 | Zylber et al. |
| 2009/0088799 A1 | 4/2009 | Yeh |
| 2009/0093846 A1 | 4/2009 | Hestad |
| 2009/0099606 A1 | 4/2009 | Hestad et al. |
| 2009/0105757 A1 | 4/2009 | Gimbel et al. |
| 2009/0105758 A1 | 4/2009 | Gimbel et al. |
| 2009/0177231 A1 | 7/2009 | Kiester |
| 2009/0198280 A1 | 8/2009 | Spratt et al. |
| 2009/0204152 A1 | 8/2009 | Blain |
| 2009/0228045 A1 | 9/2009 | Hayes et al. |
| 2009/0240285 A1 | 9/2009 | Friedrich et al. |
| 2009/0240286 A1 | 9/2009 | Friedrich et al. |
| 2009/0259257 A1 | 10/2009 | Prevost |
| 2009/0275983 A1 | 11/2009 | Veldman et al. |
| 2009/0299411 A1* | 12/2009 | Laskowitz ......... A61B 17/7008 606/246 |
| 2010/0010542 A1 | 1/2010 | Jackson |
| 2010/0010543 A1 | 1/2010 | Jackson |
| 2010/0036423 A1 | 2/2010 | Hayes |
| 2010/0137912 A1 | 6/2010 | Alcock et al. |
| 2010/0174319 A1 | 7/2010 | Jackson |
| 2010/0211105 A1 | 8/2010 | Moumene et al. |
| 2010/0228292 A1* | 9/2010 | Arnold ............... A61B 17/7005 606/264 |
| 2010/0331887 A1 | 12/2010 | Jackson et al. |
| 2011/0004222 A1* | 1/2011 | Biedermann ...... A61B 17/7091 606/104 |
| 2011/0301644 A1 | 12/2011 | Belliard |
| 2012/0035660 A1 | 2/2012 | Jackson |
| 2012/0053636 A1 | 3/2012 | Schmocker |
| 2012/0221054 A1 | 8/2012 | Jackson |

(56) References Cited

U.S. PATENT DOCUMENTS

| | | |
|---|---|---|
| 2013/0123853 A1 | 5/2013 | Seme et al. |
| 2013/0197582 A1 | 8/2013 | Prevost et al. |
| 2014/0018857 A1 | 1/2014 | Jackson |
| 2014/0039555 A1 | 2/2014 | Jackson |
| 2014/0121703 A1 | 5/2014 | Jackson |
| 2014/0222076 A1 | 8/2014 | Jackson |
| 2014/0343610 A1 | 11/2014 | Jackson |
| 2014/0379030 A1 | 12/2014 | Jackson |
| 2015/0216567 A1 | 8/2015 | Trautwein et al. |
| 2015/0230827 A1 | 8/2015 | Zylber et al. |
| 2015/0320449 A1 | 11/2015 | Jackson |
| 2016/0310169 A1 | 10/2016 | Jackson et al. |
| 2016/0354118 A1 | 12/2016 | Belliard et al. |
| 2017/0100165 A1 | 4/2017 | Jackson |
| 2017/0231662 A1 | 8/2017 | Jackson |
| 2018/0132901 A1 | 5/2018 | Jackson et al. |
| 2018/0185068 A1 | 7/2018 | Jackson |
| 2018/0221063 A1 | 8/2018 | Jackson |
| 2018/0243008 A1 | 8/2018 | Jackson |
| 2019/0183534 A1 | 6/2019 | Jackson |
| 2019/0231395 A1 | 8/2019 | Jackson |
| 2019/0239925 A1 | 8/2019 | Jackson |
| 2020/0138482 A1 | 5/2020 | Jackson |

\* cited by examiner

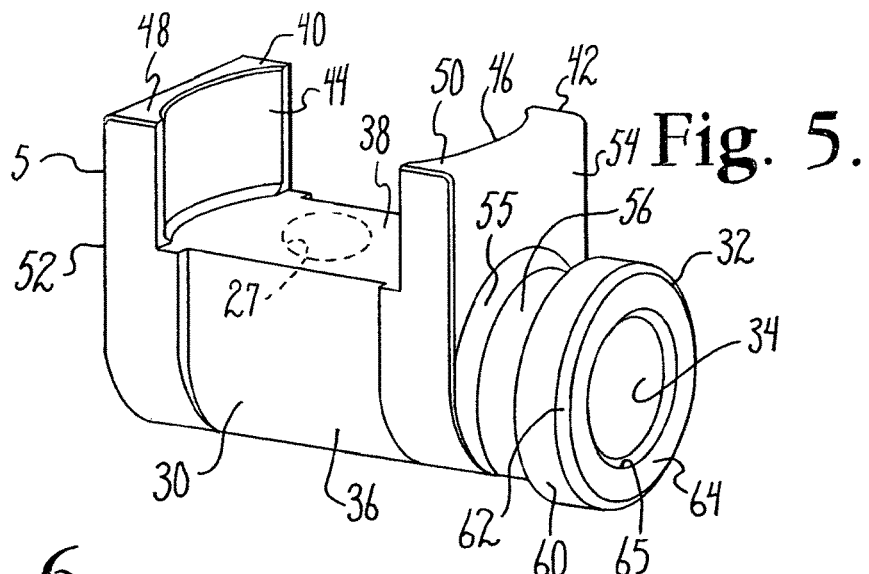
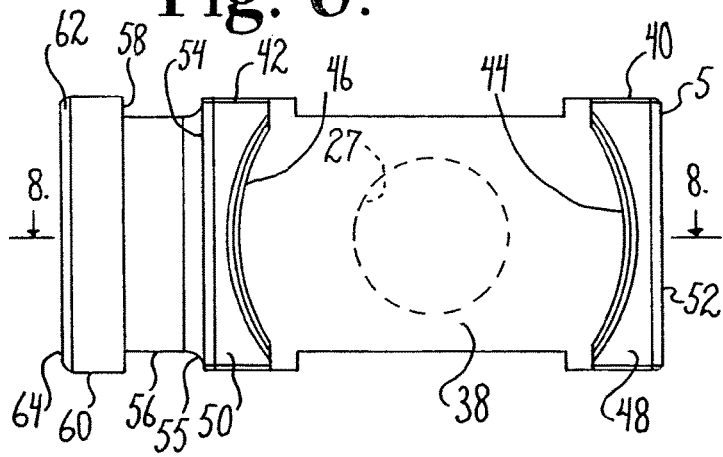
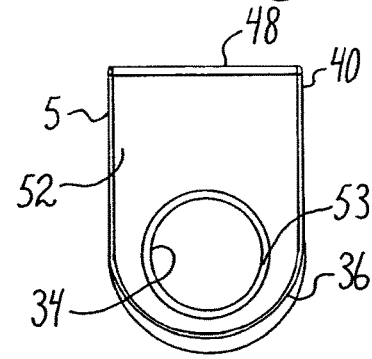
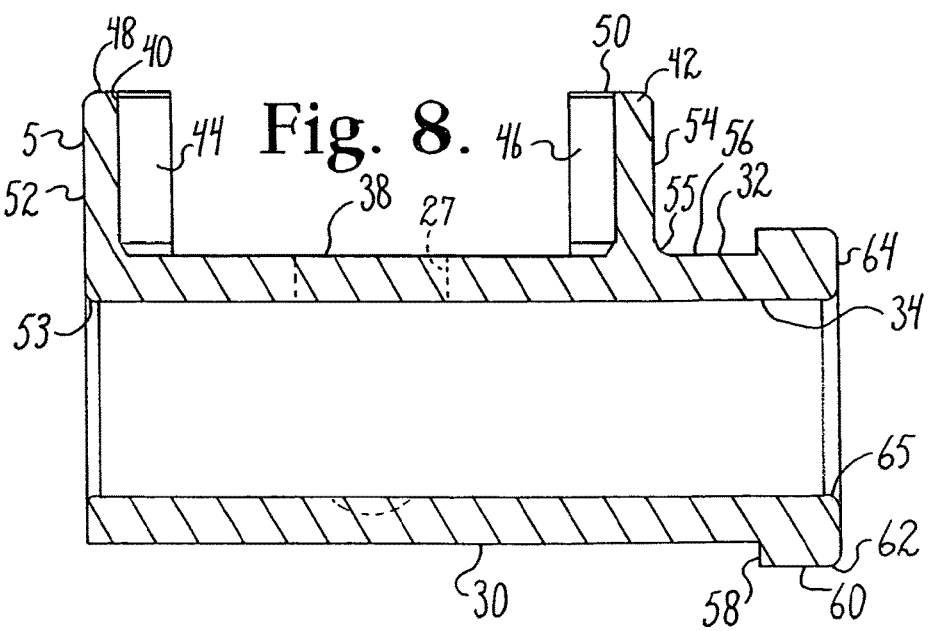

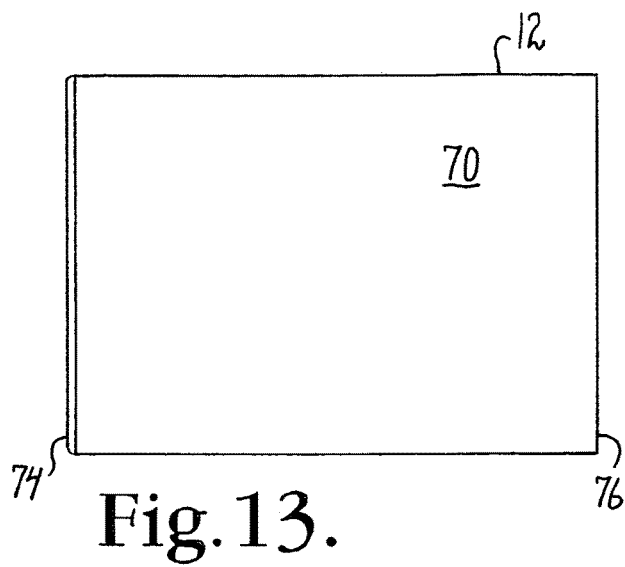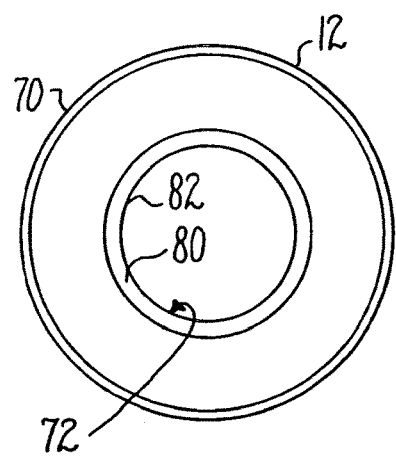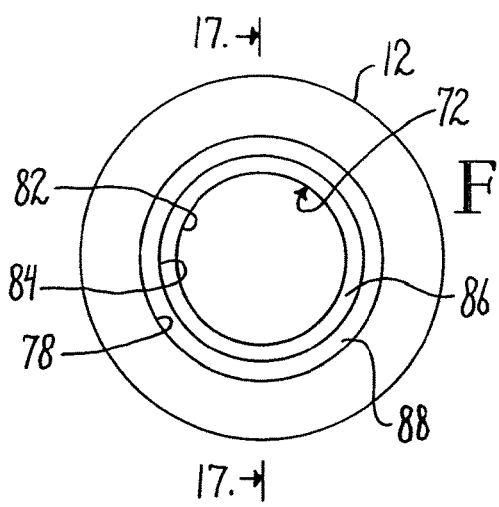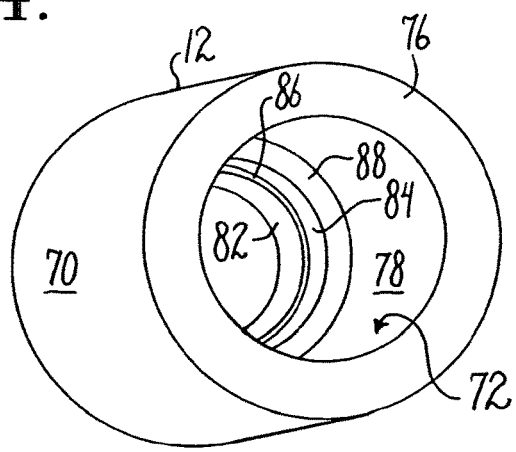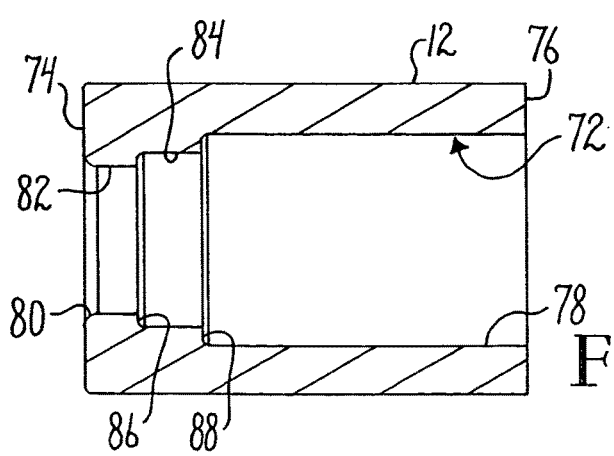

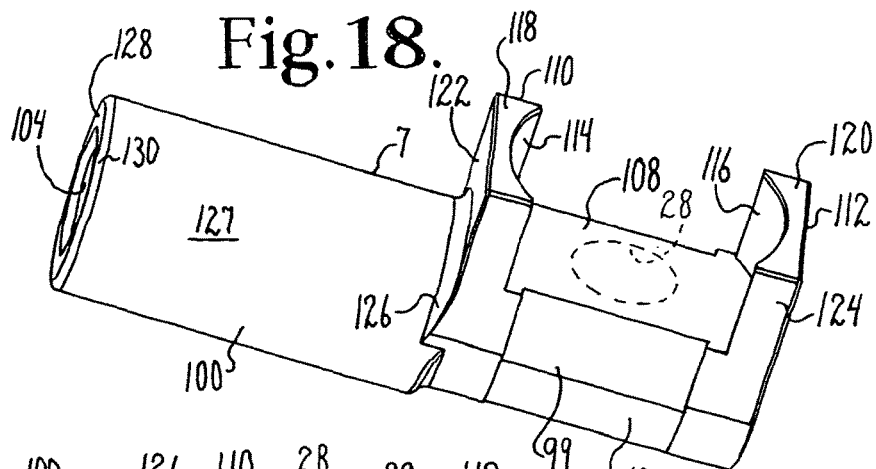
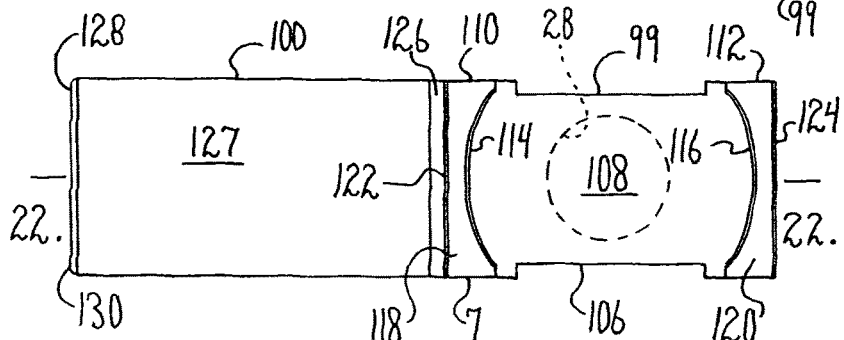
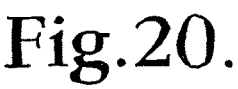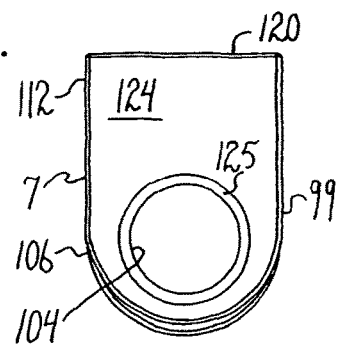
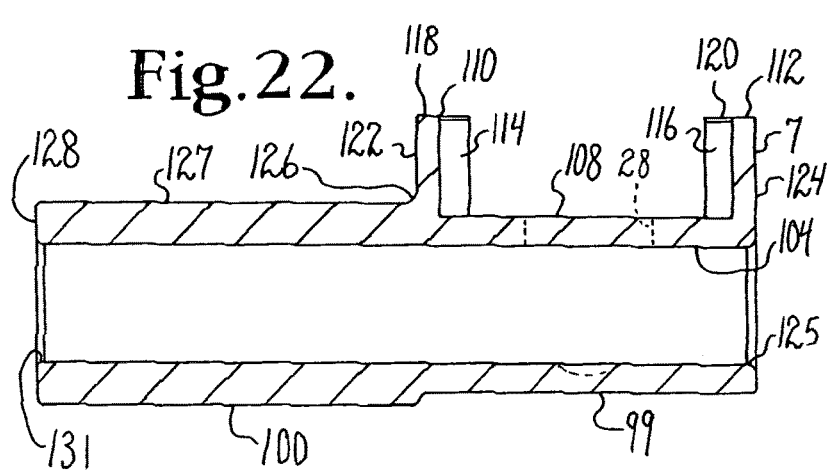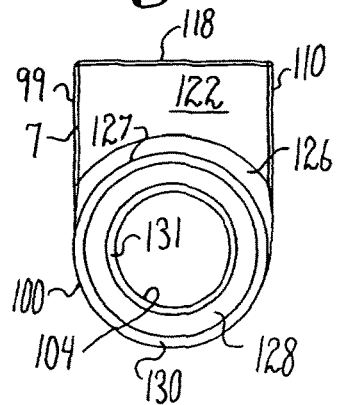

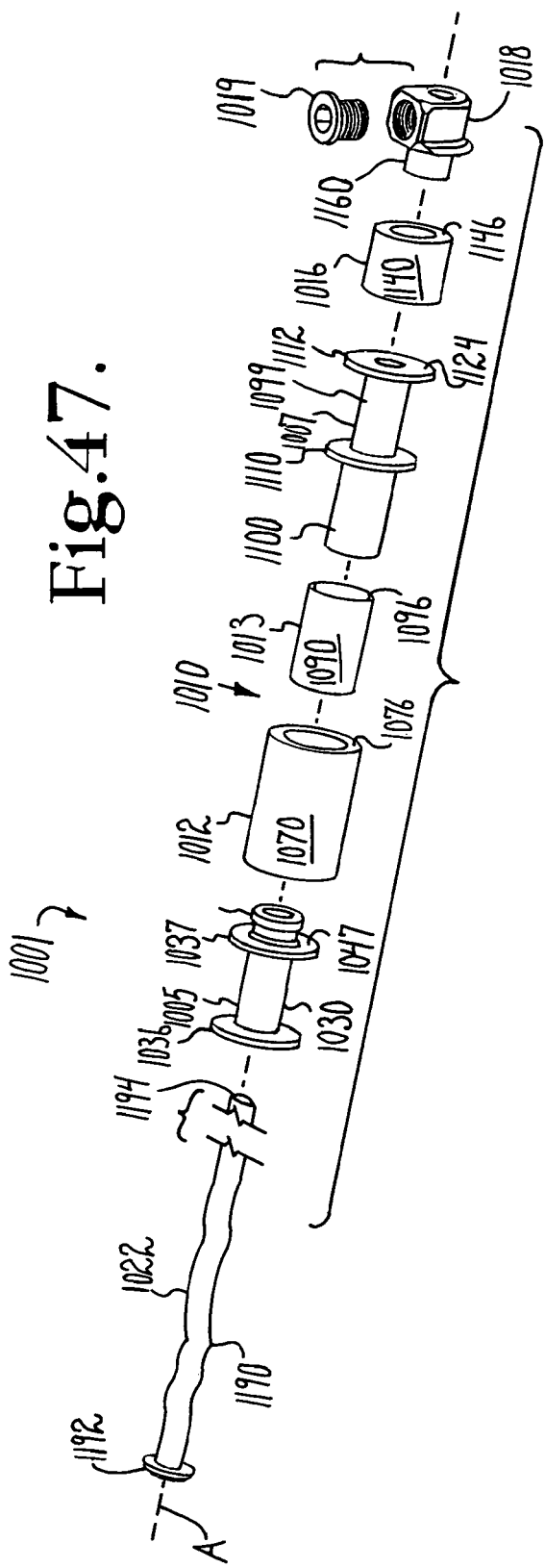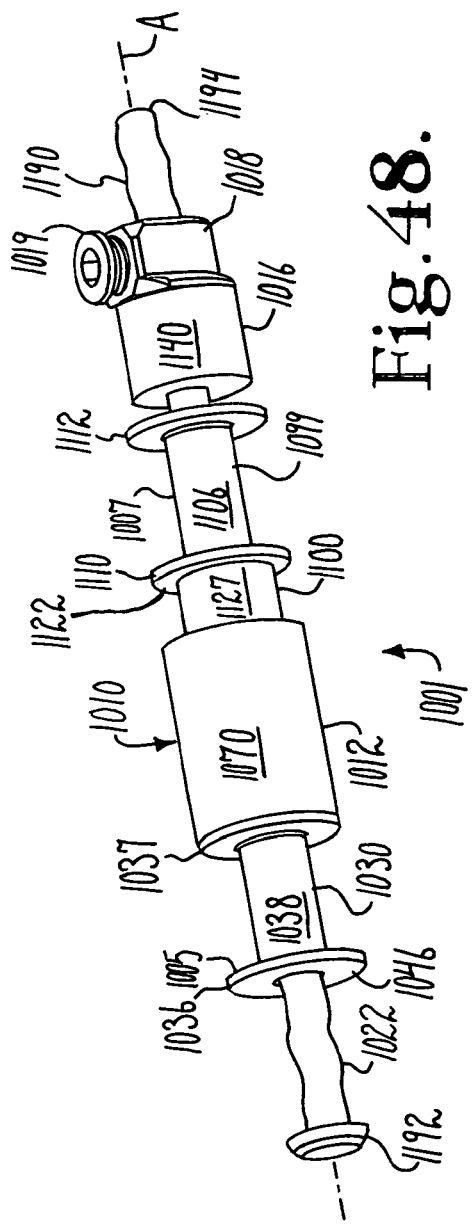

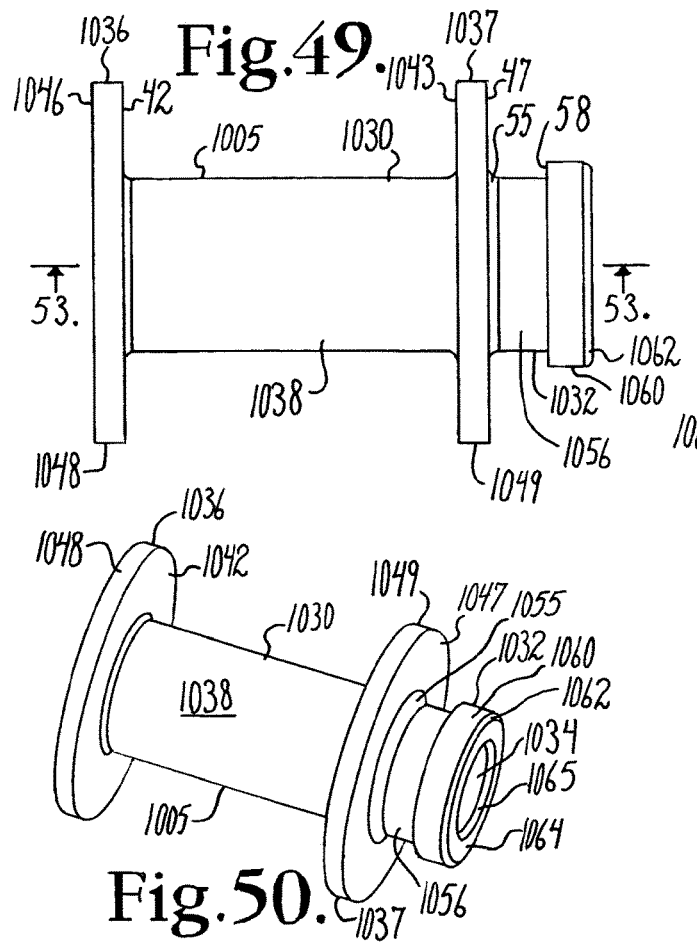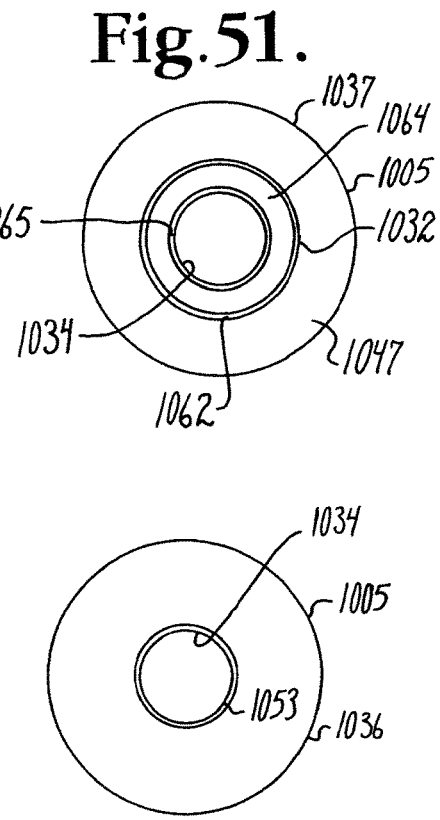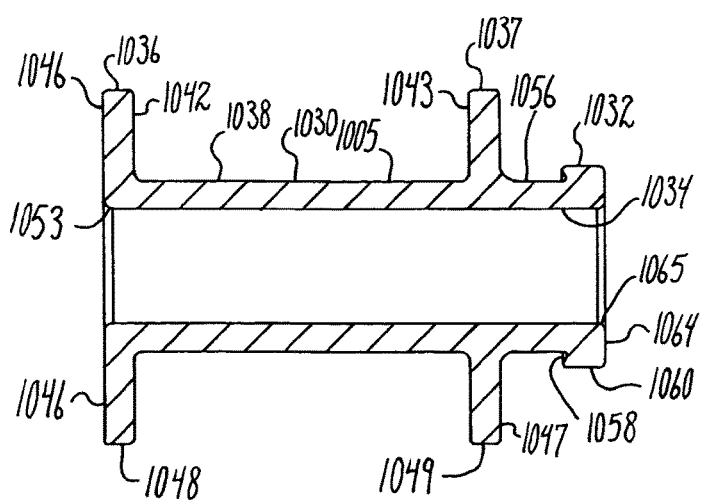

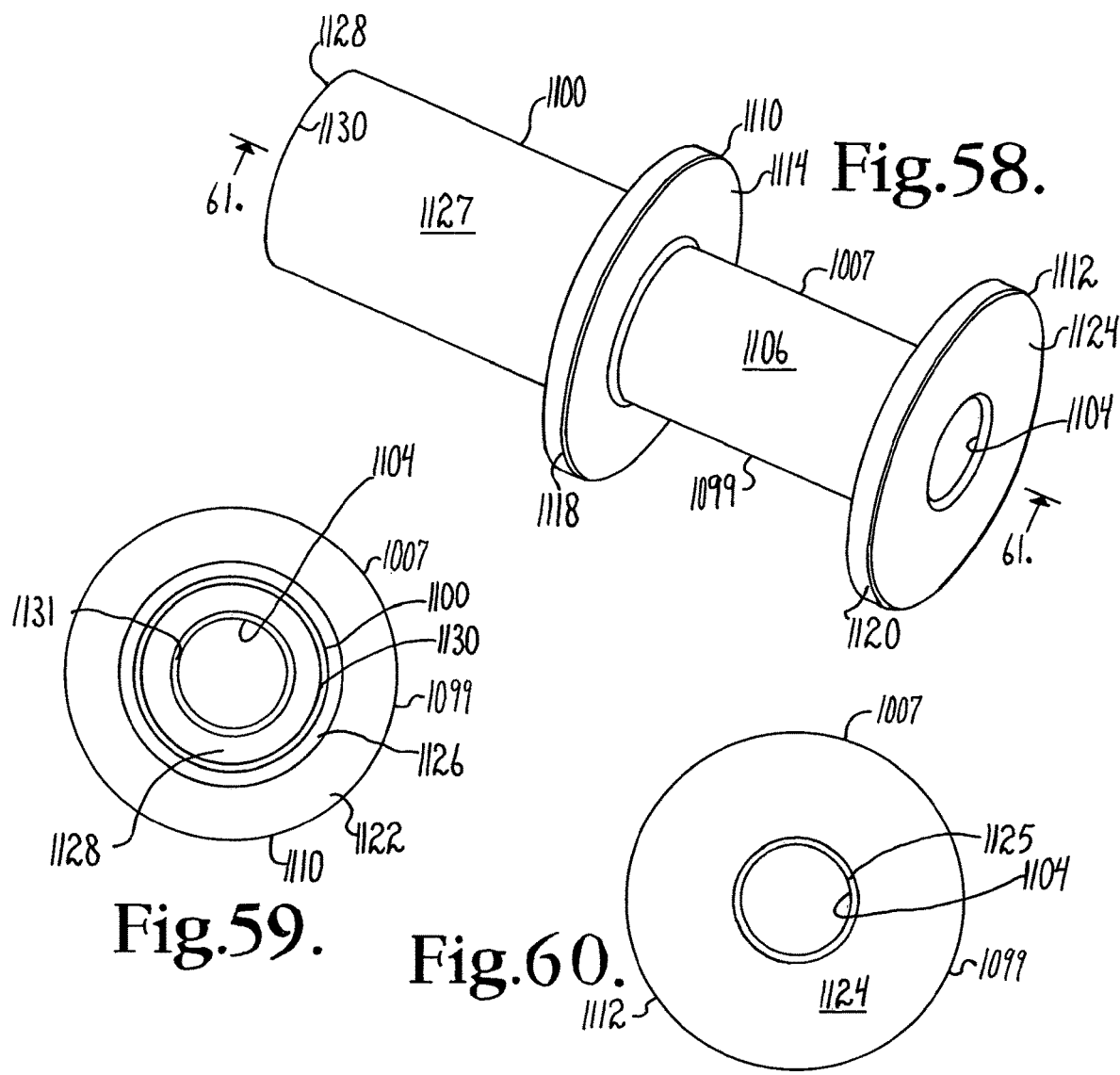
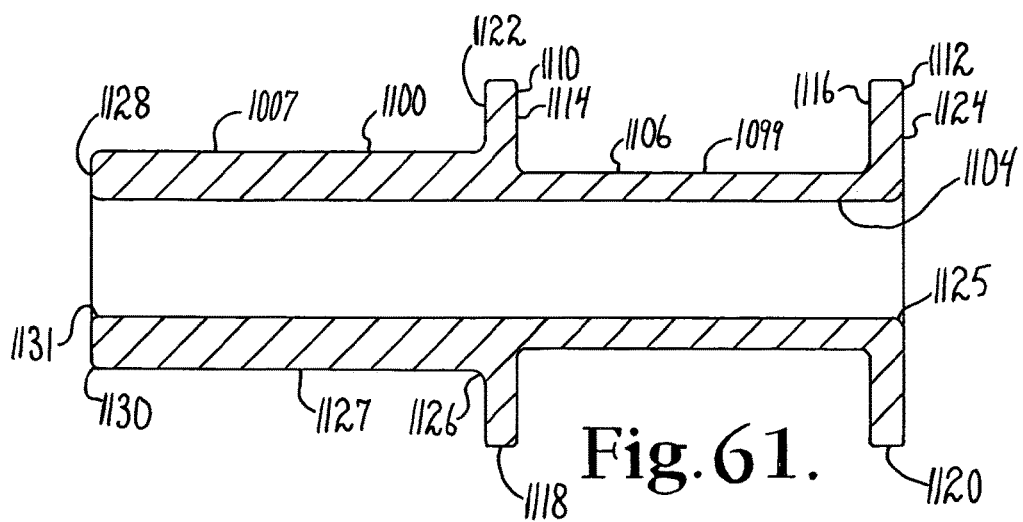

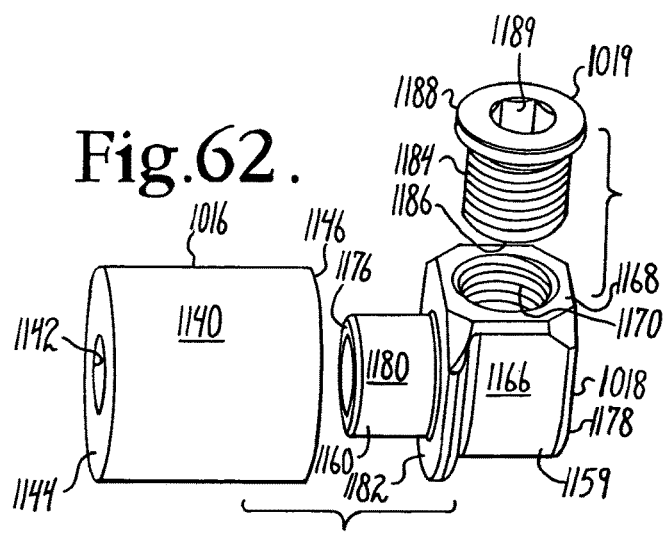
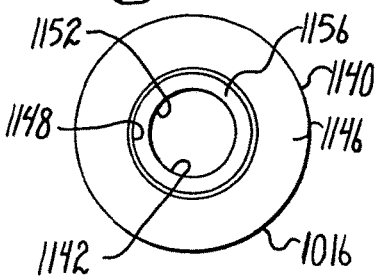
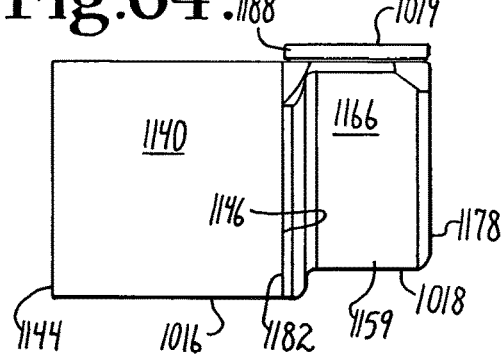
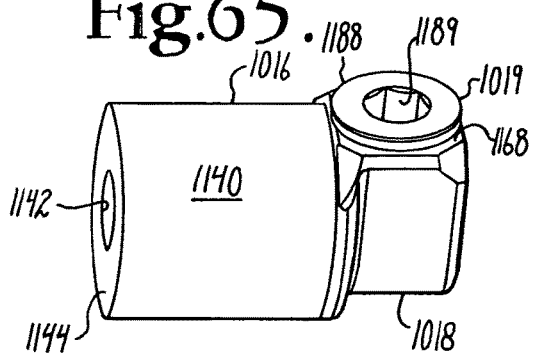
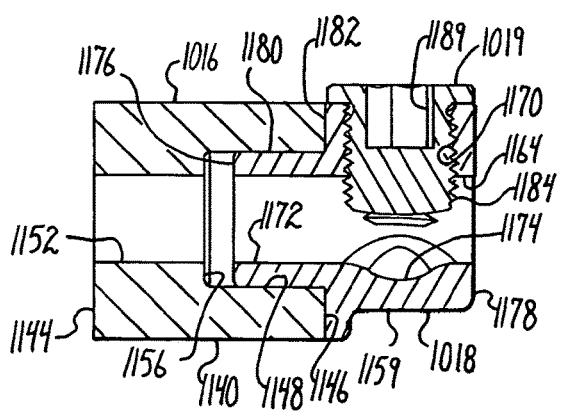
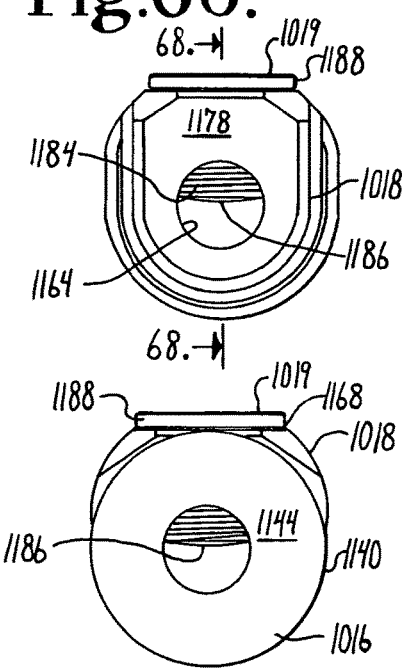

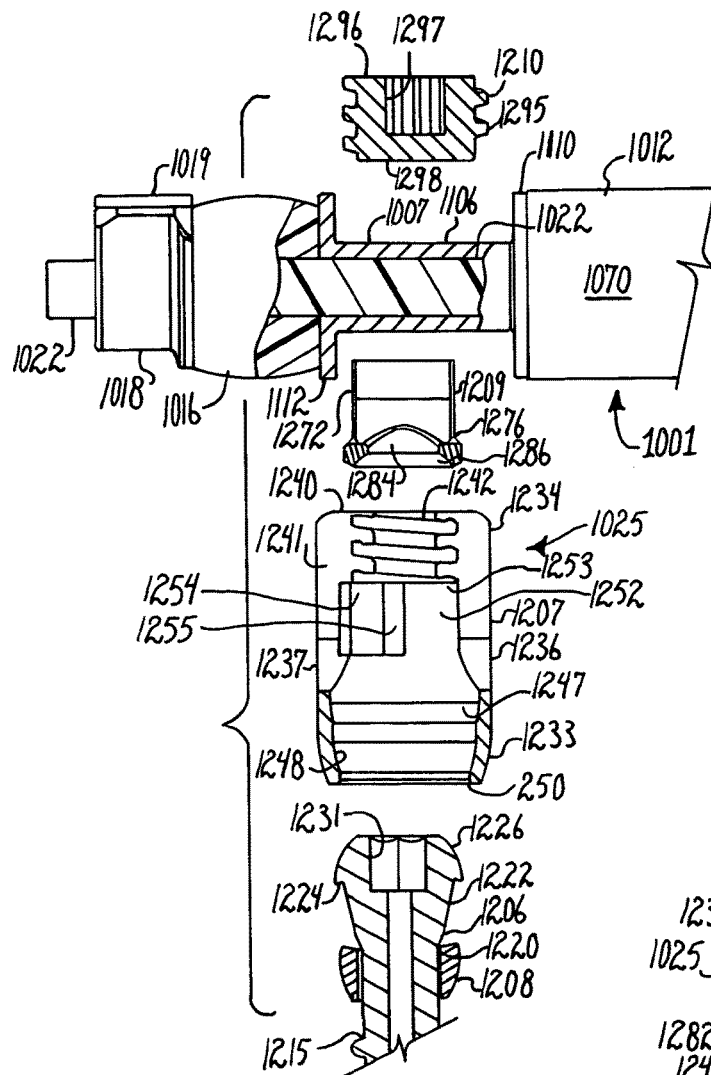
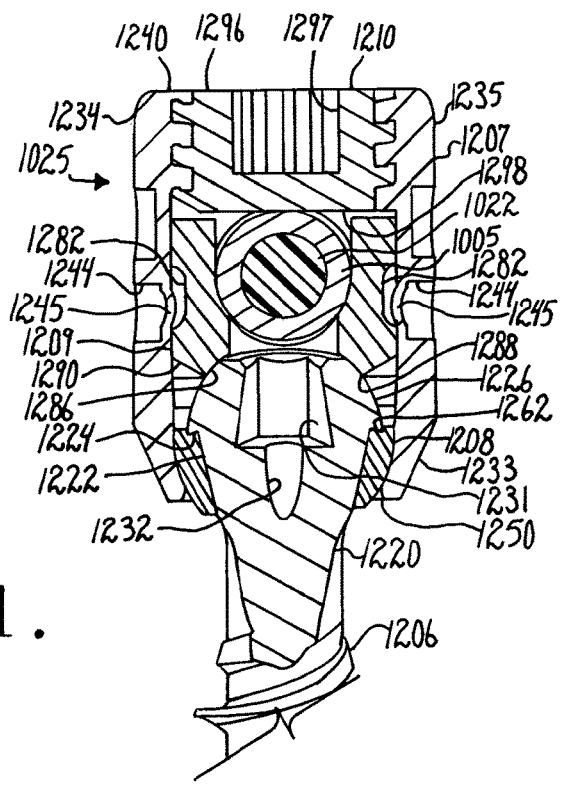
Fig.70.
Fig.71.

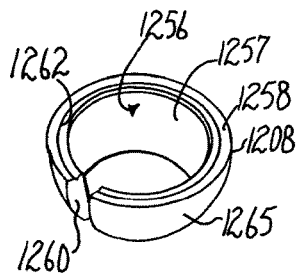
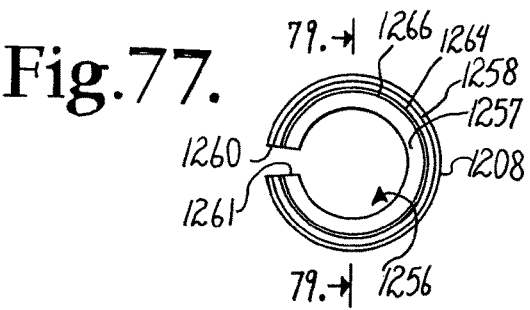
Fig.77.
Fig.76.
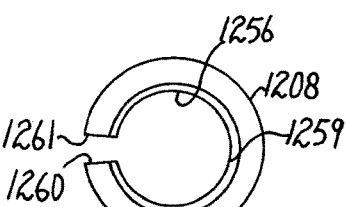
Fig.78.
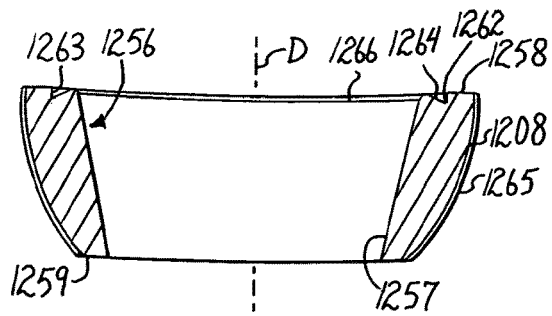
Fig.79.
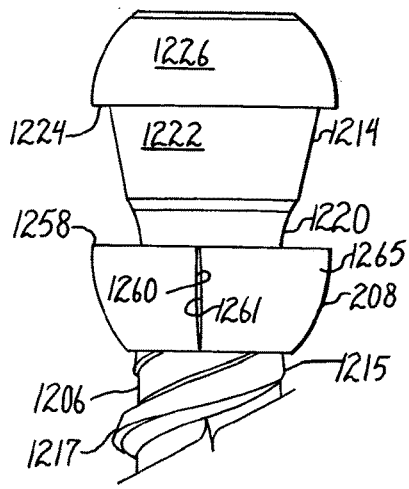
Fig.80.
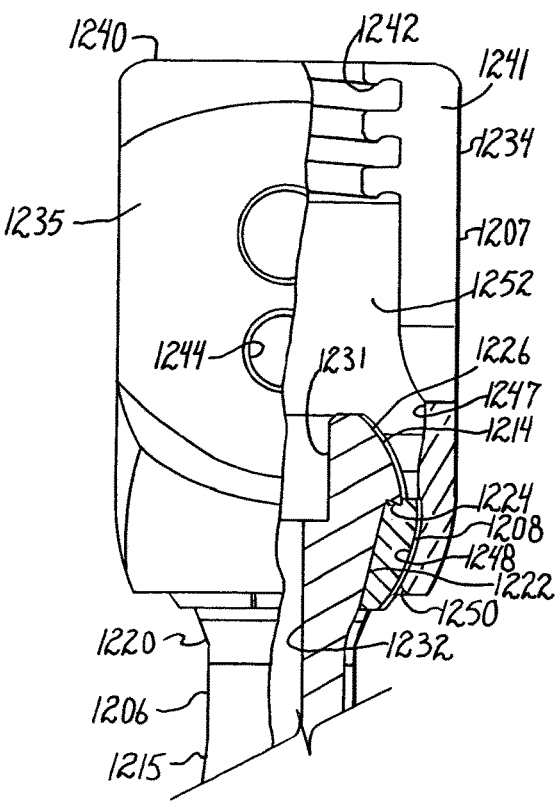
Fig.81.

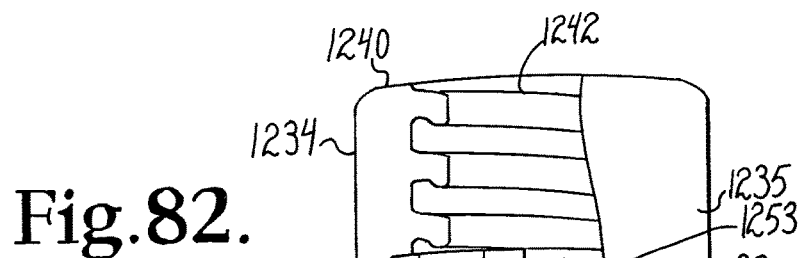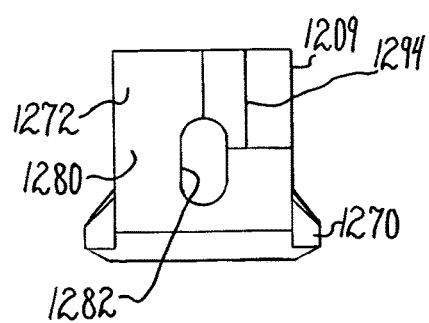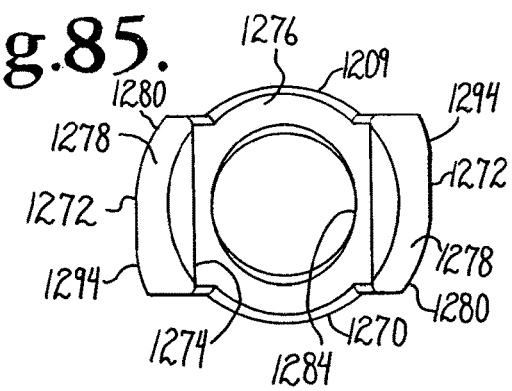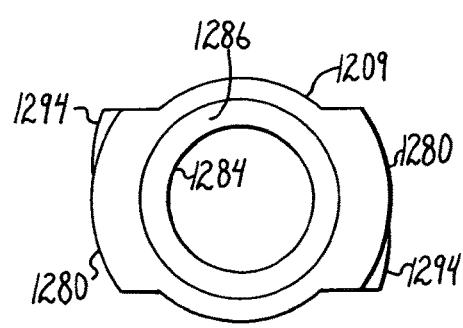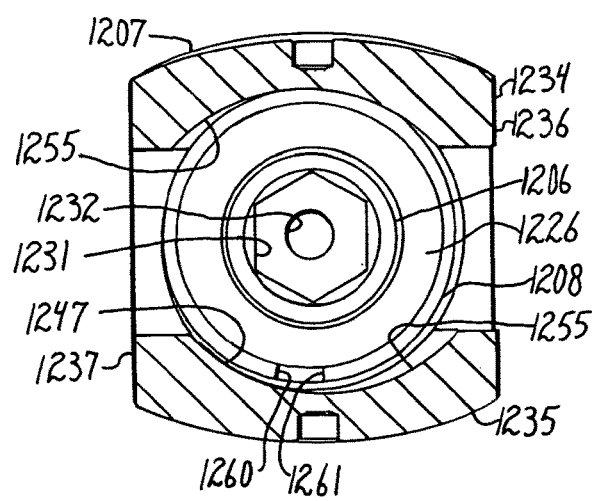

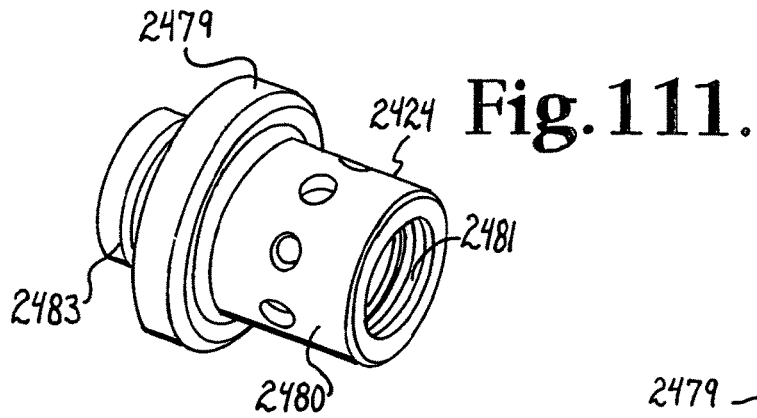
Fig. 111.
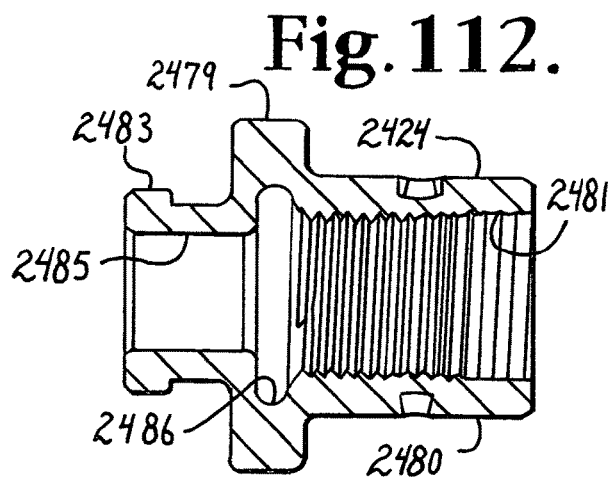
Fig. 112.
Fig. 113.
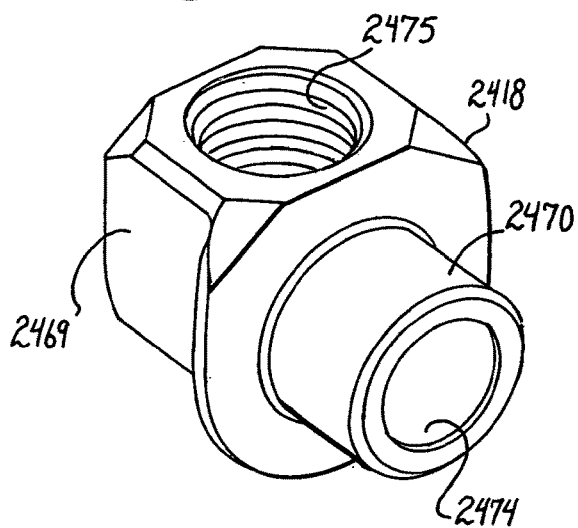
Fig. 114.
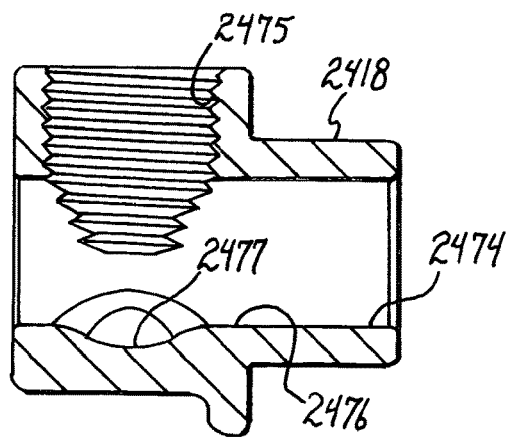

LONGITUDINAL CONNECTING MEMBER WITH SLEEVED TENSIONED CORDS AND RELEASABLE END BLOCKER-BUMPER

CROSS-REFERENCE TO RELATED APPLICATIONS

This application is a continuation of U.S. application Ser. No. 12/802,849 filed Jun. 15, 2010, which application claims the benefit of the following U.S. Provisional Patent Application Ser. Nos. 61/268,708, filed Jun. 15, 2009; 61/270,754, filed Jul. 13, 2009; 61/336,911 filed Jan. 28, 2010; 61/395,564 filed May 14, 2010; 61/395,752 filed May 17, 2010; and 61/396,390 filed May 26, 2010; all of which are incorporated by reference herein. Application Ser. No. 12/802,849 is also a continuation-in-part of U.S. patent application Ser. No. 12/221,442 filed Aug. 1, 2008 that is a continuation-in-part of U.S. patent application Ser. No. 11/328,481 filed Jan. 9, 2006, now U.S. Pat. No. 7,862,587, both of which are also incorporated by reference herein. Application Ser. No. 12/802,849 is also a continuation-in-part of U.S. patent application Ser. No. 12/148,465 filed Apr. 18, 2008 that claims the benefit of U.S. Provisional Patent Application Ser. No. 60/927,111 filed May 1, 2007, both of which are incorporated by reference herein. Application Ser. No. 12/802,849 is also a continuation-in-part of U.S. patent application Ser. No. 12/661,042 filed Mar. 10, 2010 that claims the benefit of U.S. Provisional Patent Application Ser. No. 61/210,058 filed Mar. 13, 2009, both of which are incorporated by reference herein.

BACKGROUND OF THE INVENTION

The present invention is directed to dynamic fixation assemblies for use in bone surgery, particularly spinal surgery, and in particular to longitudinal connecting members and cooperating bone anchors or fasteners for such assemblies, the connecting members being attached to at least two bone anchors.

Historically, it has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist bending (flexion, extension and lateral), torsion, shear, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially inelastic rigid support in all planes.

An alternative to fusion, which immobilizes at least a portion of the spine, and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, side bending, distraction, compression and torsion. Another type of soft or dynamic system known in the art includes bone anchors connected by flexible cords or strands, typically made from a plastic material. Such a cord or strand may be threaded through cannulated spacers that are disposed between adjacent bone anchors when such a cord or strand is implanted, tensioned and attached to the bone anchors. The spacers typically span the distance between bone anchors, providing limits on the bending movement of the cord or strand and thus strengthening and supporting the overall system. Shear forces are not well resisted by the typical cord and spacer stabilization systems. Such tensioned cord and spacer systems may also cause facet joint compression during spinal movement, especially flexion.

The complex dynamic conditions associated with spinal movement create challenges for the design of elongate elastic longitudinal connecting members that exhibit an adequate fatigue strength to provide stabilization and protected motion of the spine, without fusion, and that allow for some natural movement of the portion of the spine being reinforced and supported by the elongate elastic or flexible connecting member. A further challenge are situations in which a portion or length of the spine requires a more rigid stabilization, possibly including fusion, while another portion or length may be better supported by a more dynamic system that allows for protective movement.

SUMMARY OF THE INVENTION

Longitudinal connecting member assemblies according to the invention for use between at least two bone anchors provide dynamic, protected motion of the spine and may be extended to provide additional dynamic sections or more rigid support along an adjacent length of the spine, with fusion, if desired. A dynamic longitudinal connecting member assembly according to the invention has an inner segment or core made from a cord in the disclosed embodiment, the core being tensioned and fixed at either end of the assembly. The core is received by at least one hard, inelastic segment or sleeve, the sleeve attachable to at least one bone anchor. In some embodiments, the core is received by at least a pair of such sleeves, each sleeve attachable to a bone anchor. In some embodiments, the sleeve or sleeves slidingly receive the core. In other embodiments, the sleeve or sleeves are either fixed or left unfixed to the core by the surgeon, resulting in a connecting member having variable segmental stiffness along a length thereof. A variety of embodiments according to the invention are possible. Additional sleeves may be attached to additional bone anchors and cooperate with additional cut-to-length spacers with or without cooperating liners to create longer assemblies. Sleeves may also be extended to provide inelastic rod, bar or tube extensions, especially on one end. Spacers and optional cooperating liners with different measures of rigidity may be connected according to embodiments of the invention. Either rigid lengths or cords may be of greater or lesser lengths for attaching to one or a plurality of bone anchors. In some embodiments, longitudinal connecting member assemblies may be dynamically loaded before insertion, or after being operatively attached to at least the pair of bone anchors along a patient's spine by tensioning the inner core and at least partially compressing an end bumper and/or at least one spacer located between the bone anchors. Typically, the at least one spacer with or without an inner liner has some flexibility in bending, with the spacer/liner combination protecting and limiting flexing movement of the inner core and providing shear resistance.

An object of the invention is to provide a lightweight, reduced volume, low profile assemblies for use with at least two bone anchors. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 5 is an enlarged perspective view of the first sleeve of FIG. 2.

FIG. 6 is an enlarged top plan view of the first sleeve of FIG. 5.

FIG. 7 is an enlarged rear elevational view of the first sleeve of FIG. 5.

FIG. 8 is an enlarged cross-sectional view taken along the line 8-8 of FIG. 6.

FIG. 13 is an enlarged side elevational view of the spacer of the spacer/liner combination of FIG. 2.

FIG. 14 is an enlarged rear elevational view of the spacer of FIG. 13.

FIG. 15 is an enlarged front elevational view of the spacer of FIG. 13.

FIG. 16 is an enlarged perspective view of the spacer of FIG. 13.

FIG. 17 is an enlarged cross-sectional view taken along the line 17-17 of FIG. 14.

FIG. 18 is an enlarged perspective view of the second sleeve shown in FIG. 2.

FIG. 19 is en enlarged top plan view of the second sleeve of FIG. 18.

FIG. 20 is an enlarged front elevational view of the second sleeve of FIG. 18.

FIG. 21 is an enlarged rear elevational view of the second sleeve of FIG. 18.

FIG. 22 is an enlarged cross-sectional view taken along the line 22-22 of FIG. 19.

FIG. 47 is an enlarged and exploded perspective view of the connecting member of FIG. 45 shown without the polyaxial bone screws, the connecting member including an inner cord, first and second sleeves, a spacer/liner combination, an elastic bumper and a cord blocker with set screw.

FIG. 48 is an enlarged perspective view of the connecting member of FIG. 47 shown with the components loosely connected along the inner cord and prior to tensioning.

FIG. 49 is an enlarged side elevational view of the first sleeve of FIG. 48.

FIG. 50 is an enlarged perspective view of the first sleeve of FIG. 49.

FIG. 51 is an enlarged front elevational view of the first sleeve of FIG. 49.

FIG. 52 is an enlarged rear elevational view of the first sleeve of FIG. 49.

FIG. 53 is an enlarged cross-sectional view taken along the line 53-53 of FIG. 49.

FIG. 58 is an enlarged perspective view of the second sleeve shown in FIG. 47.

FIG. 59 is en enlarged rear elevational view of the second sleeve of FIG. 58.

FIG. 60 is an enlarged front elevational view of the second sleeve of FIG. 58.

FIG. 61 is an enlarged cross-sectional view taken along the line 61-61 of FIG. 58.

FIG. 62 is an enlarged exploded perspective view of the bumper, blocker and set screw shown in FIG. 47.

FIG. 63 is an enlarged front elevational view of the bumper of FIG. 62.

FIG. 64 is an enlarged side elevational view of the bumper, blocker and set screw of FIG. 62 shown assembled.

FIG. 65 is an enlarged perspective view of the bumper, blocker and set screw of FIG. 64.

FIG. 66 is an enlarged front elevational view of the bumper, blocker and set screw of FIG. 64.

FIG. 67 is an enlarged rear elevational view of the bumper, blocker and set screw of FIG. 64.

FIG. 68 is an enlarged cross-sectional view taken along the line 68-68 of FIG. 66.

FIG. 70 is an enlarged and partial and partially exploded side elevational view of the connector and bone screws, similar to FIG. 69, with portions broken away to show the detail thereof and the retainer and shank shown in a stage of assembly.

FIG. 71 is an enlarged and partial cross-sectional view taken along the line 71-71 of FIG. 69.

FIG. 76 is an enlarged perspective view of the retainer of FIG. 69.

FIG. 77 is a top plan view of the retainer of FIG. 69.

FIG. 78 is a bottom plan view of the retainer of FIG. 69.

FIG. 79 is a cross-sectional view taken along the line 79-79 of FIG. 77.

FIG. 80 is an enlarged and partial front elevational view of the shank and retainer of FIG. 69 shown in an early stage of assembly.

FIG. 81 is an enlarged and partial side elevational view of an assembled shank, retainer and receiver of FIG. 69 with portions broken away to show the detail thereof.

FIG. 82 is another enlarged and partial side elevational view of an assembled shank, retainer and receiver of FIG. 69 with portions broken away to show the detail thereof.

FIG. 83 is a cross-sectional view taken along the line 83-83 of FIG. 82.

FIG. 84 is an enlarged side elevational view of the compression insert of FIG. 69.

FIG. 85 is an enlarged top plan view of the compression insert of FIG. 69.

FIG. 86 is an enlarged bottom plan view of the compression insert of FIG. 69.

FIG. 111 is an enlarged perspective view of the rod/cord coupler of FIG. 97.

FIG. 112 is a side elevational view of the rod/cord coupler of FIG. 111 with portions broken away to show the detail thereof.

FIG. 113 is an enlarged perspective view the cord blocker of FIG. 97.

FIG. 114 is a side elevational view of the cord blocker of FIG. 113 with portions broken away to show the detail thereof.

FIG. 118 is a front elevational view of the closure top of FIG. 117 with portions broken away to show the detail thereof.

FIG. 119 is an enlarged front elevational view of another of the closure tops shown in FIG. 99.

FIG. 120 is a front elevational view of the closure top of FIG. 119 with portions broken away to show the detail thereof.

FIG. 121 is an enlarged front elevational view of another of the closure tops shown in FIG. 99.

FIG. 122 is a front elevational view of the closure top of FIG. 121 with portions broken away to show the detail thereof.

FIG. 123 is a perspective view of another sleeve according to the invention shown mounted within a polyaxial bone screw.

FIG. 124 is an enlarged and partial exploded perspective view of the assembly and sleeve of FIG. 123.

FIG. 125 is an enlarged and partial front elevational view of the assembly and sleeve of FIG. 123.

FIG. 126 is a cross-sectional view taken along the line 126-126 of FIG. 125.

FIG. 127 is an enlarged top plan view of the sleeve of FIG. 123.

FIG. 128 is an enlarged bottom plan view of the sleeve of FIG. 123.

FIG. 129 is a front elevational view of the assembly of FIG. 123 with portions broken away to show the detail thereof.

Figure 123:
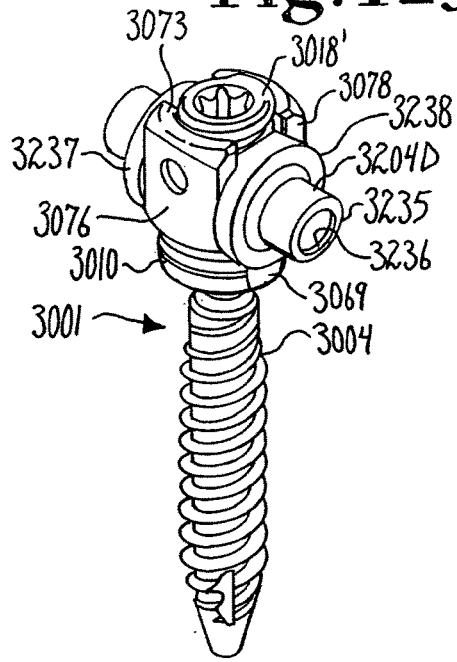
Figure 124:
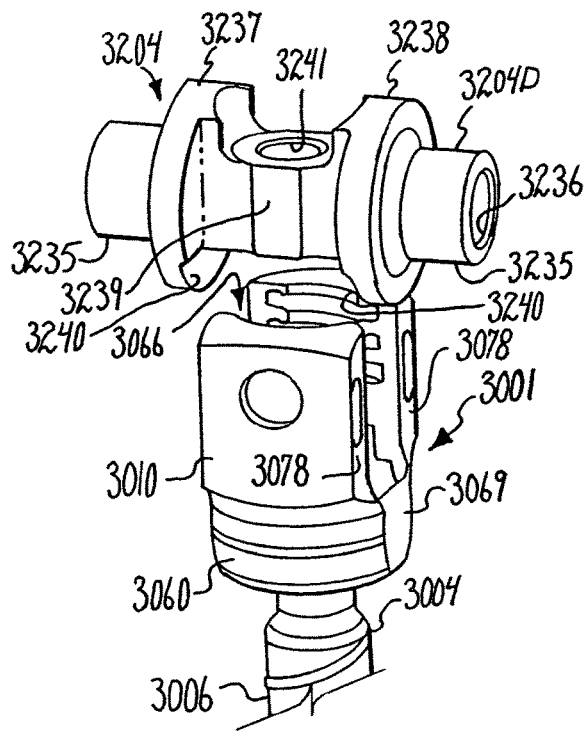
Figure 125:
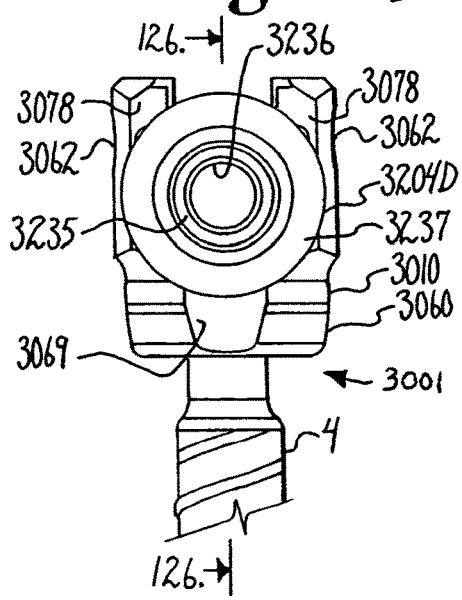
Figure 126:
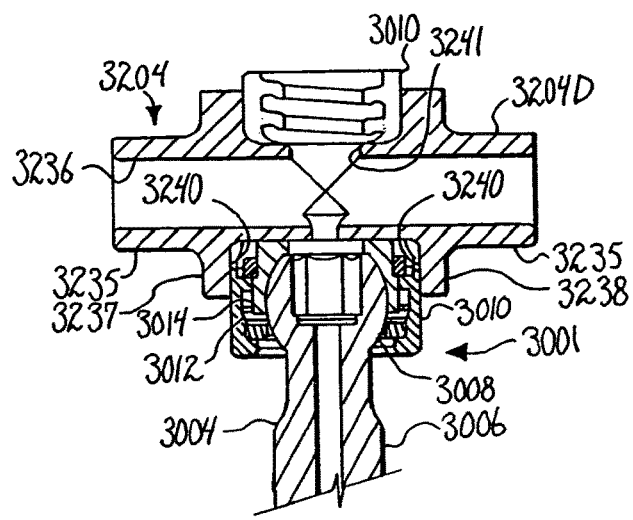
Figure 127:
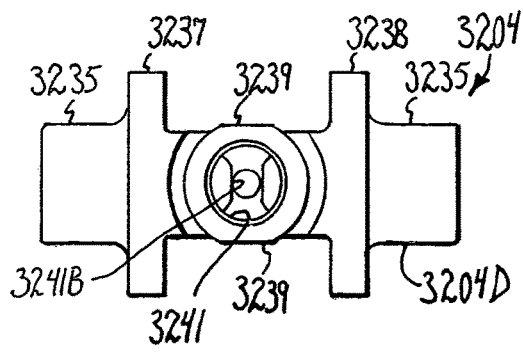
Figure 128:
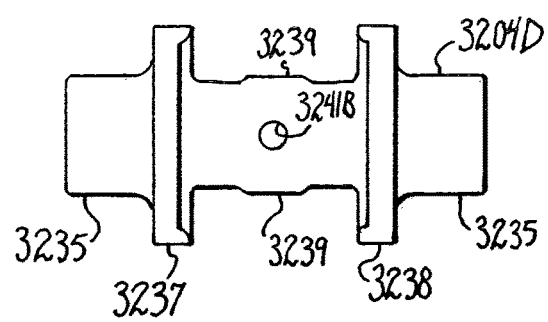
Figure 130:
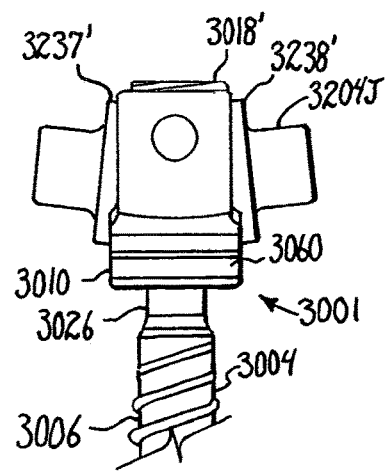

FIG. 130 is a partial side elevational view of the bone screw of FIG. 123 shown with an alternative lordotic sleeve of the invention.

Figure 131:
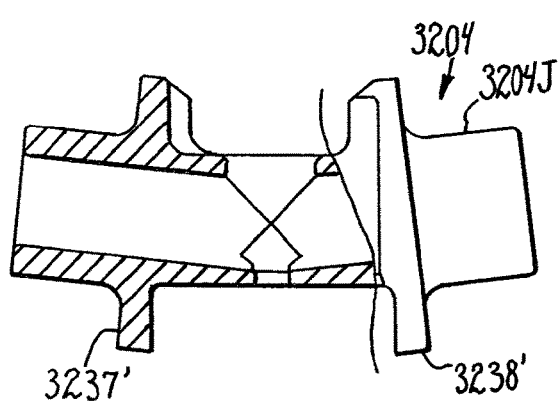

FIG. 131 is an enlarged side elevational view of the sleeve of FIG. 130 with portions broken away to show the detail thereof.

Figure 132:
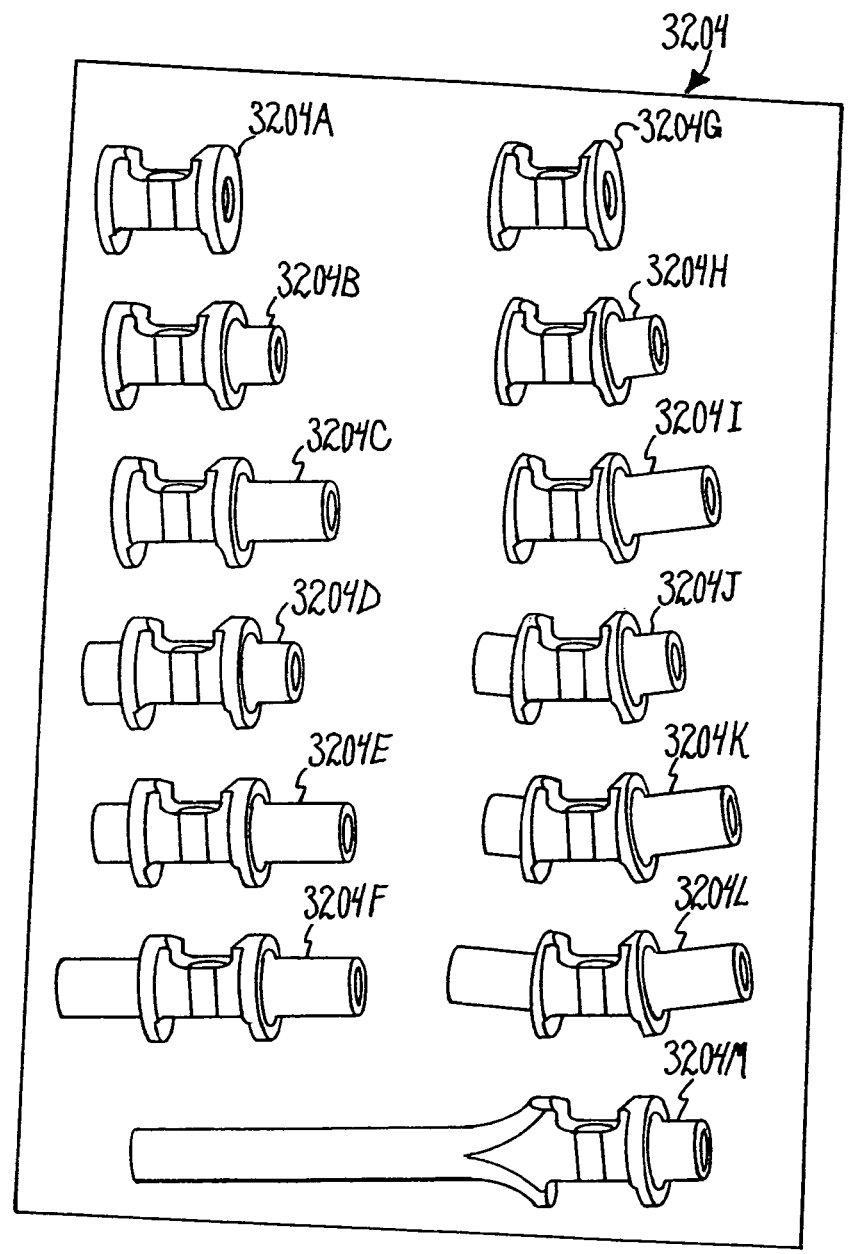

FIG. 132 is a perspective view of a set of sleeves as shown in FIGS. 123-131.

Figure 133:
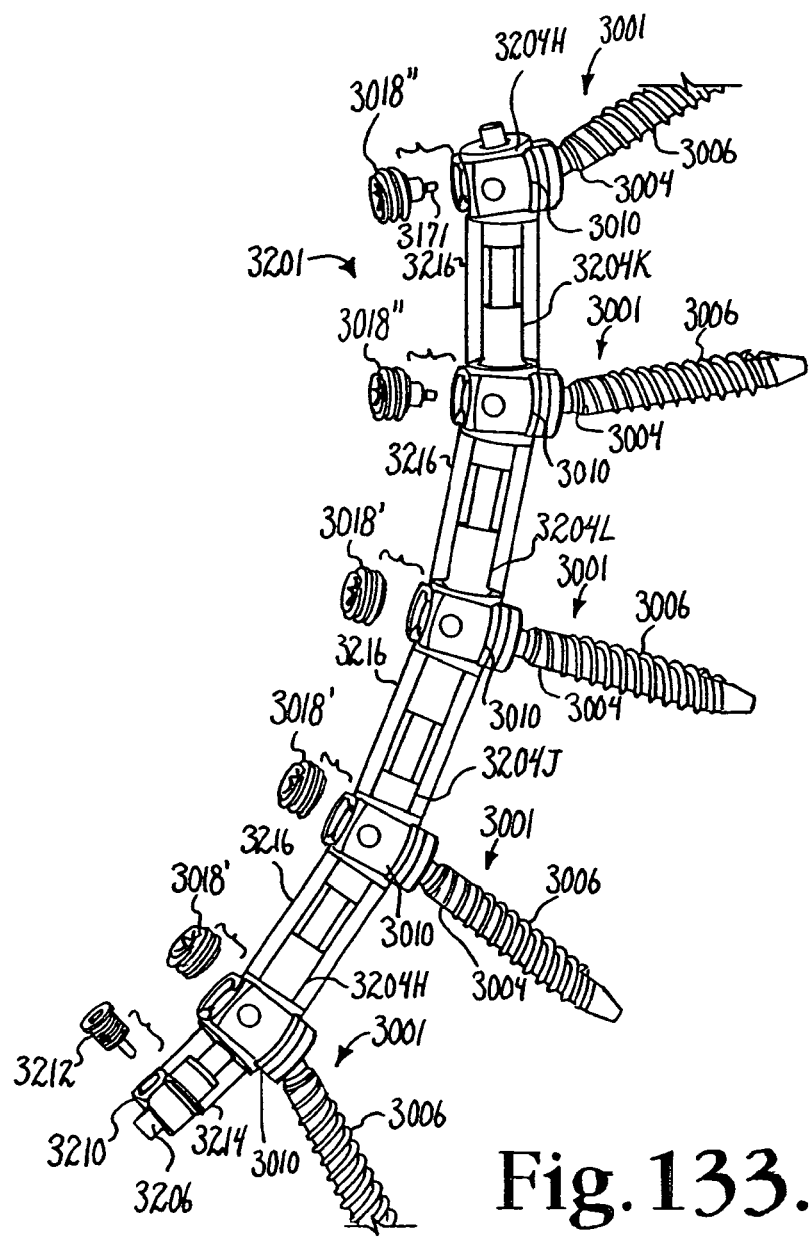

FIG. 133 is a partially exploded perspective view of a longitudinal connecting member including the assembly further including some of the sleeves of FIG. 132.

Figure 134:
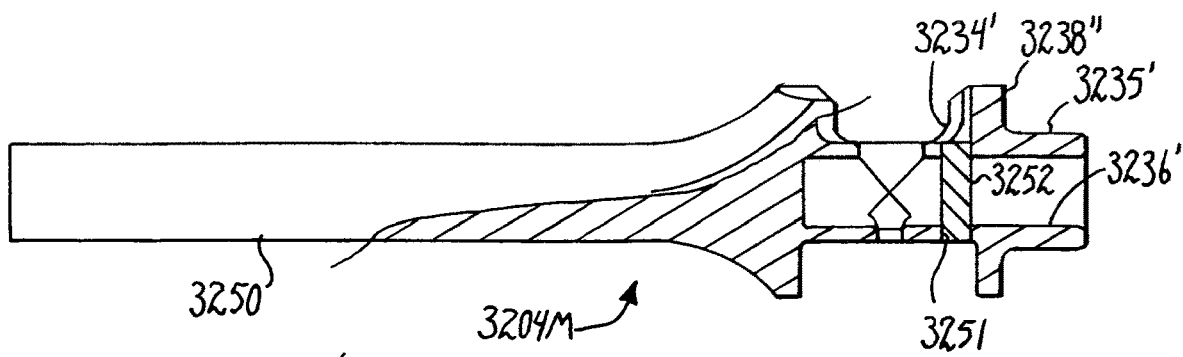

FIG. 134 is an enlarged front elevational view of one of the sleeves shown in FIG. 132 with portions broken away to show the detail thereof, the sleeve also including a cord fixer and a solid rod.

Figure 135:
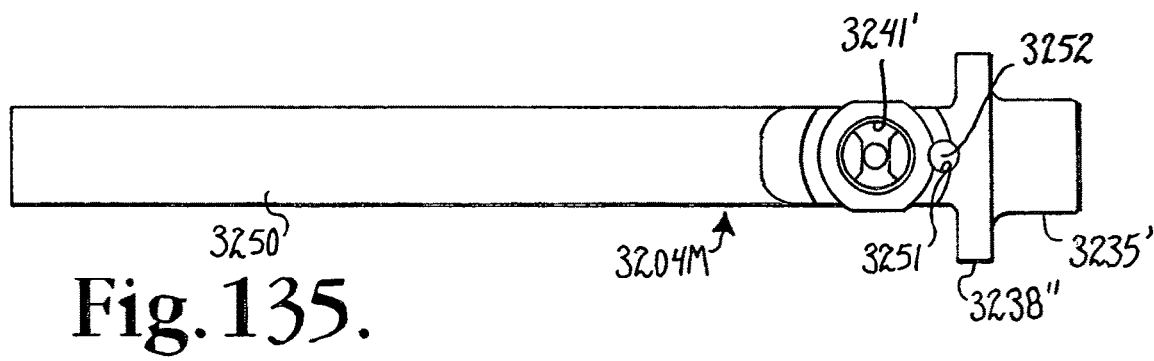

FIG. 135 is a top plan view of the sleeve of FIG. 134.

Figure 136:
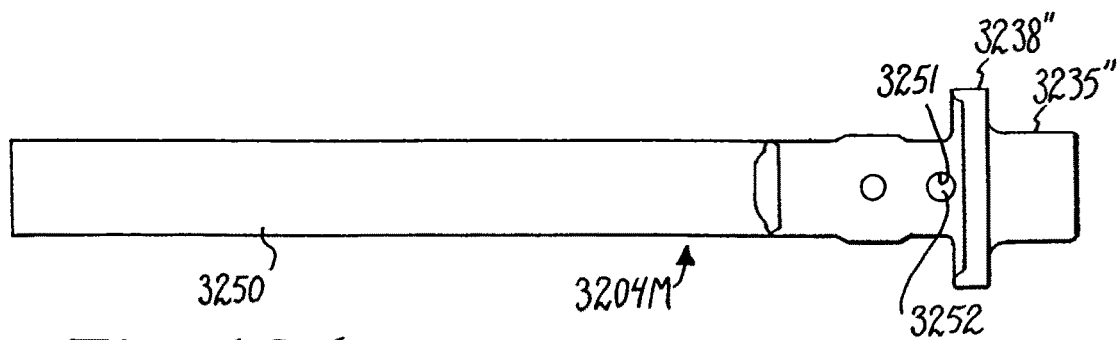

FIG. 136 is a bottom plan view of the sleeve of FIG. 134.

Figure 137:
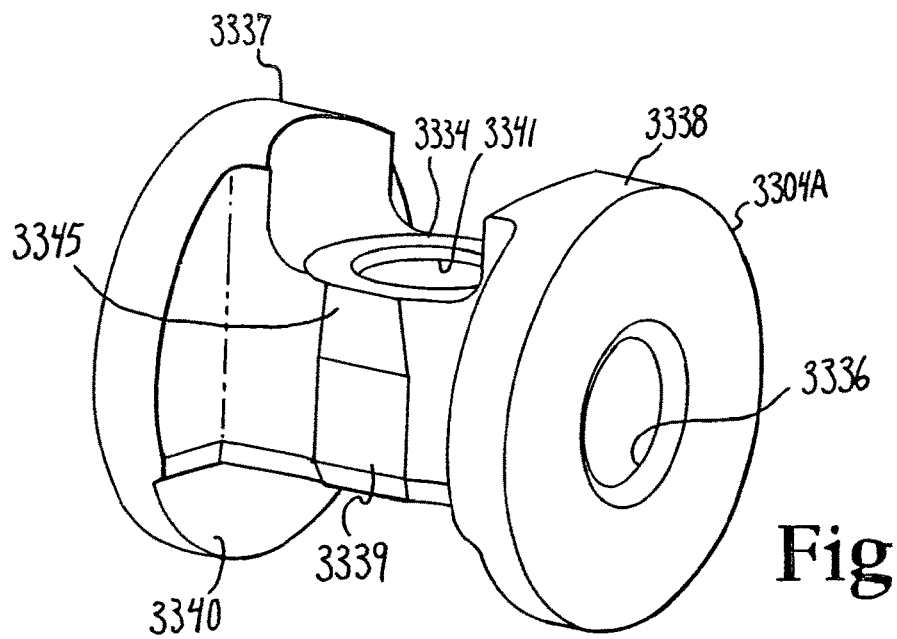

FIG. 137 is a perspective view of another alternative sleeve according to the invention.

Figure 138:
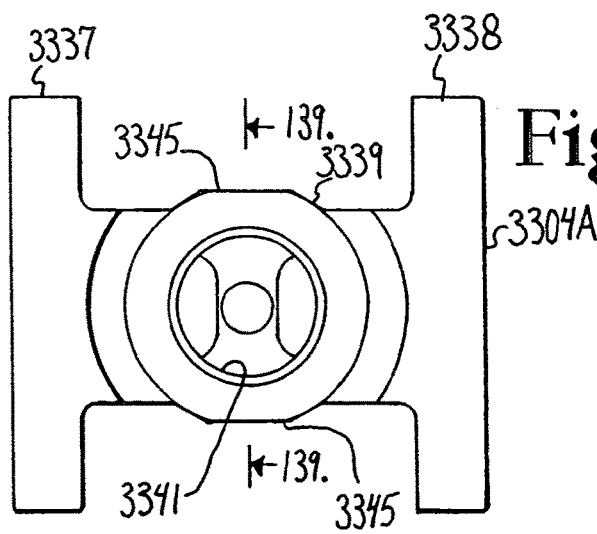

FIG. 138 is a top plan view of the sleeve of FIG. 137.

Figure 139:
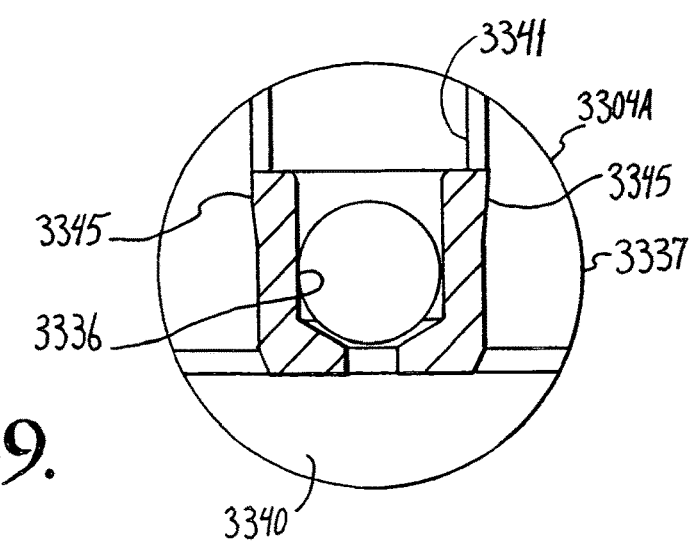

FIG. 139 is a cross-sectional view taken along the line 139-139 of FIG. 138.

Figure 140:
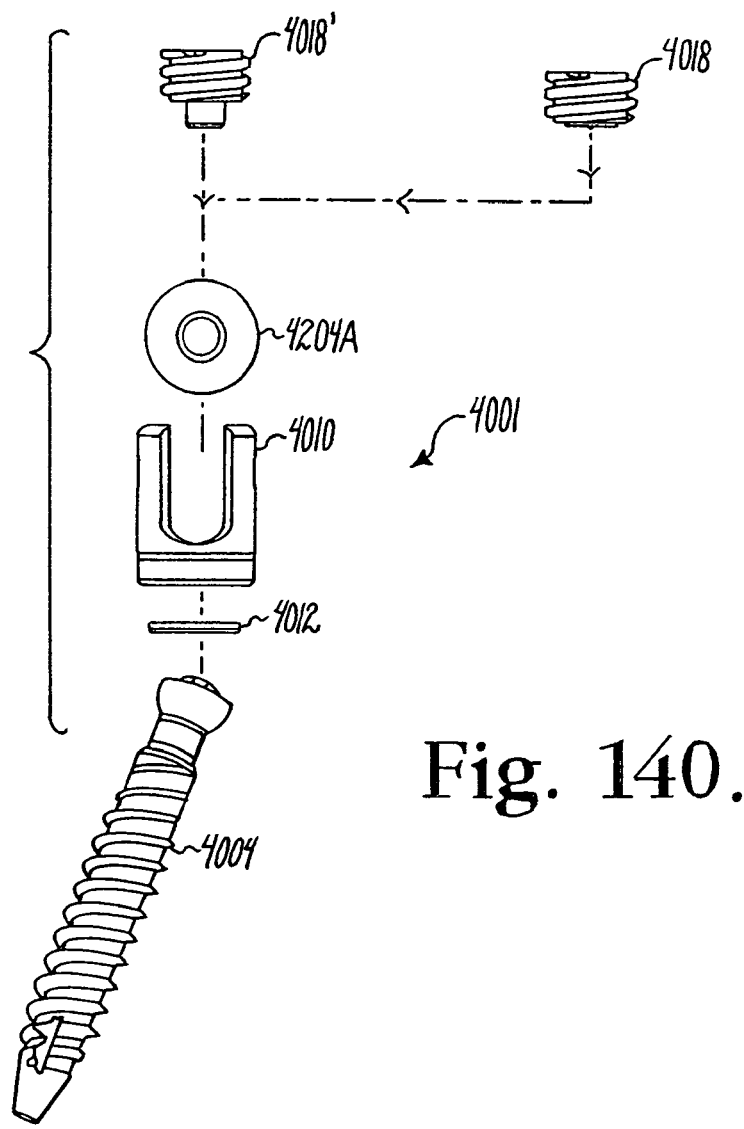

FIG. 140 is an exploded front elevational view of another sleeve according to the invention shown with a polyaxial bone screw and a pair of alternative closure tops.

Figure 141:
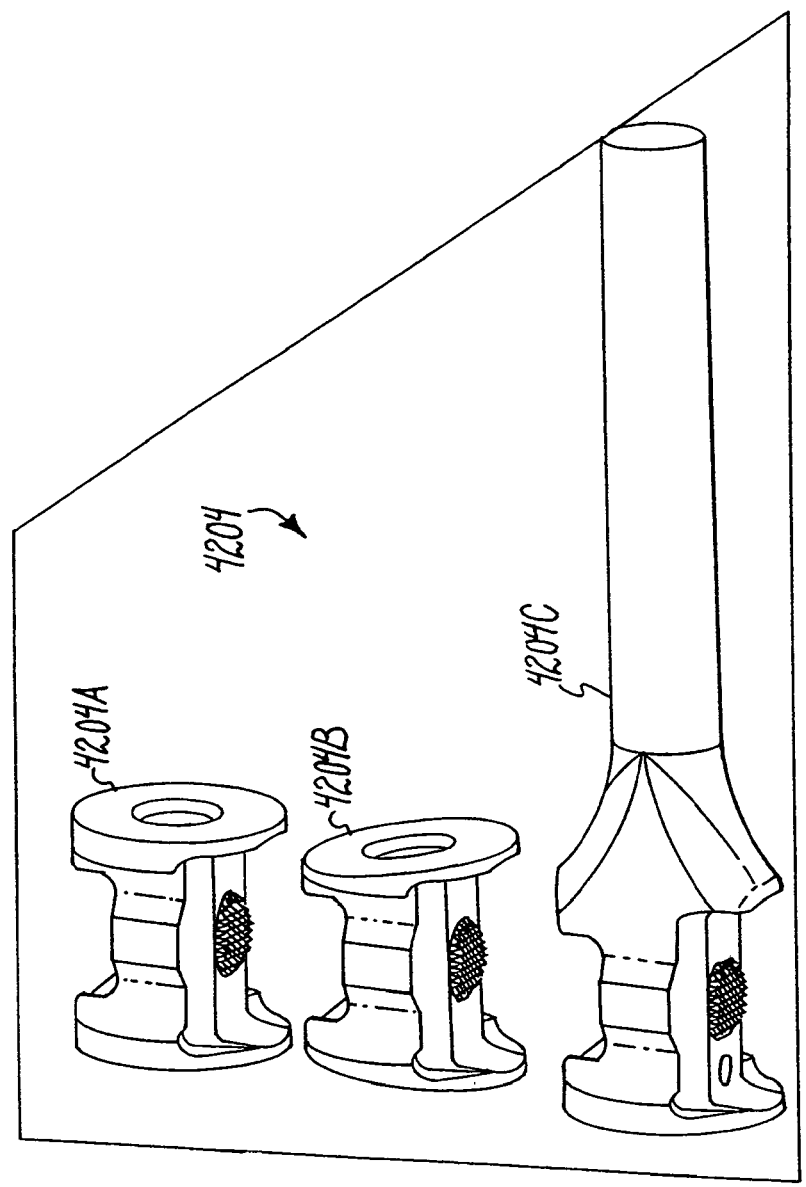

FIG. 141 is a perspective view of a set of sleeves, one of which is shown in FIG. 140.

Figure 142:
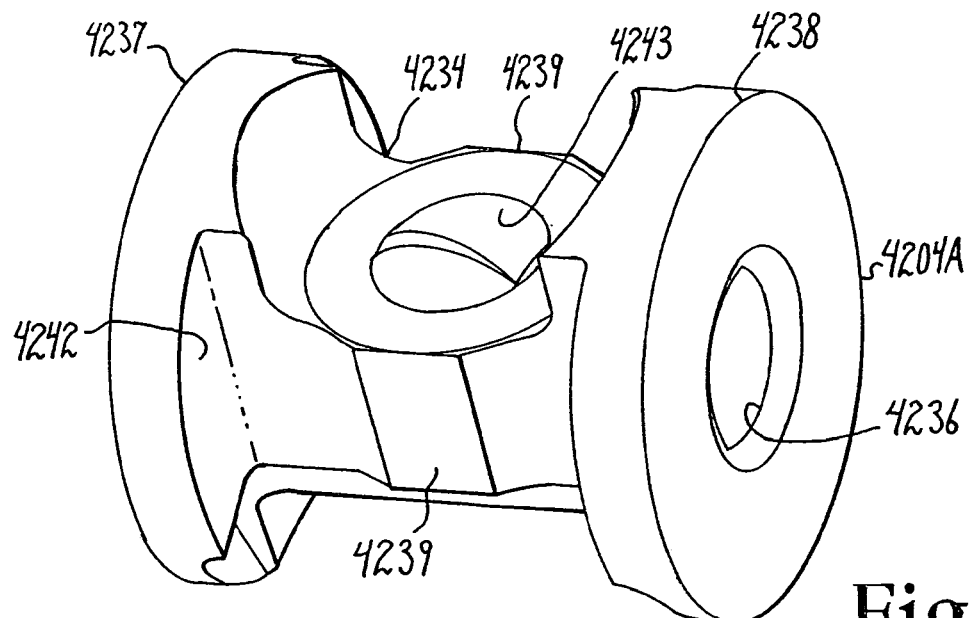

FIG. 142 is an enlarged perspective view of one of the sleeves of FIG. 141 that is also the sleeve shown in FIG. 140.

Figure 143:
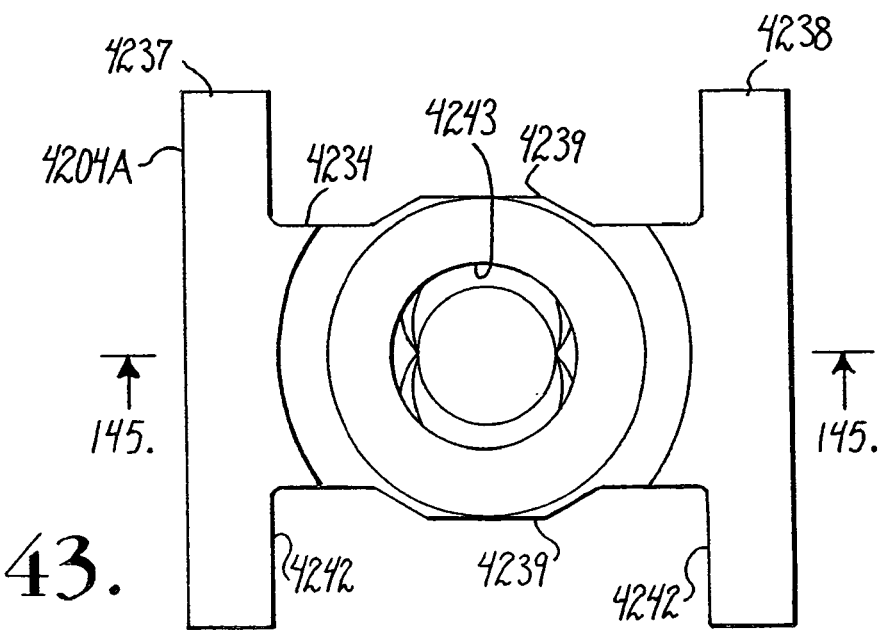

FIG. 143 is a top plan view of the sleeve of FIG. 142.

Figure 144:
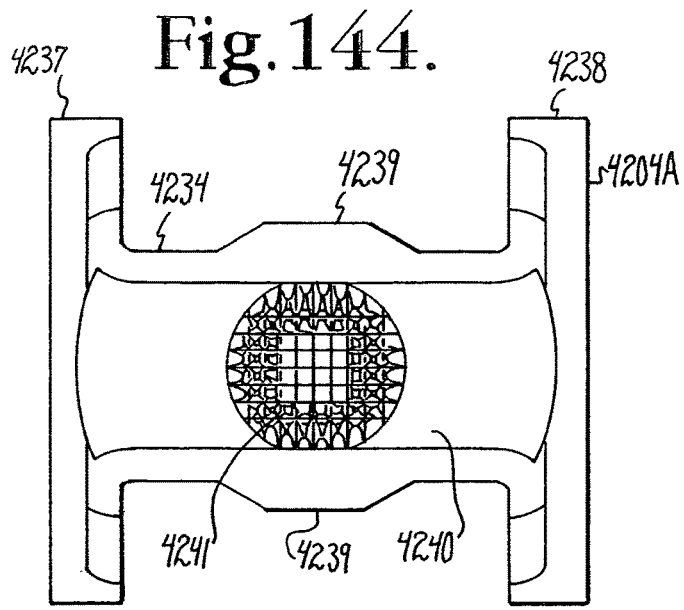

FIG. 144 is a bottom plan view of the sleeve of FIG. 142.

Figure 145:
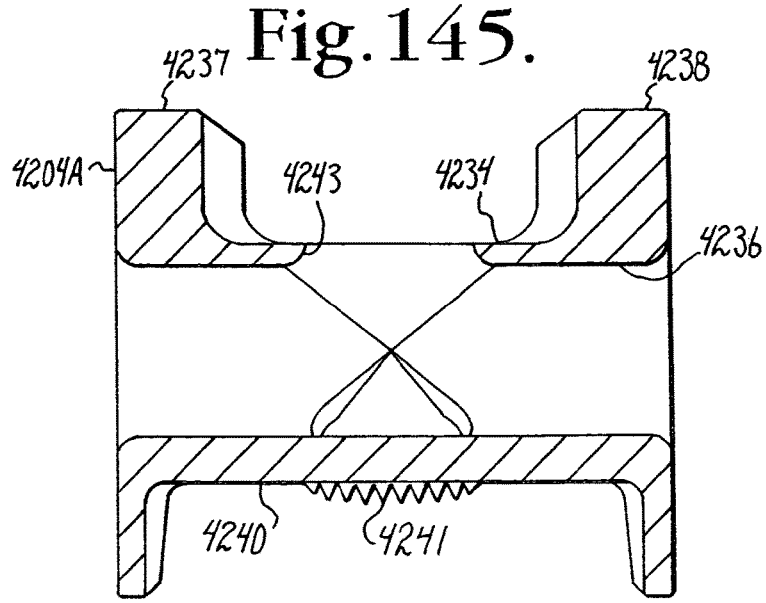

FIG. 145 is a cross-sectional view taken along the line 145-145 of FIG. 143.

Figure 146:
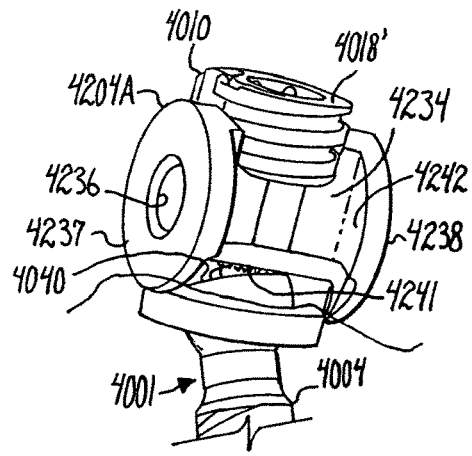

FIG. 146 is a partial perspective view of the assembly of FIG. 140 with portions broken away to show the detail thereof.

Figure 147:
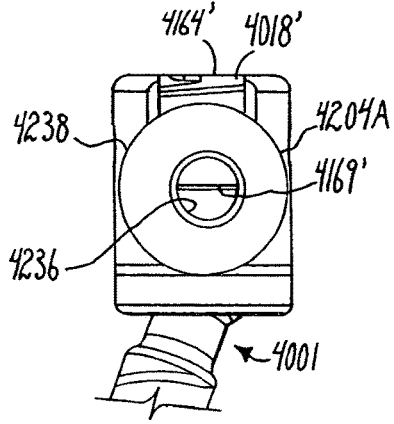

FIG. 147 is a partial front elevational view of the assembly of FIG. 146.

Figure 148:
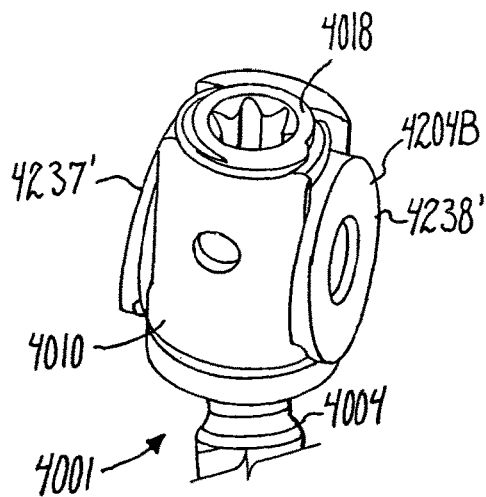

FIG. 148 is a partial perspective view of the bone screw assembly of FIG. 140 shown with one of the lordotic sleeve illustrated in FIG. 141.

Figure 149:
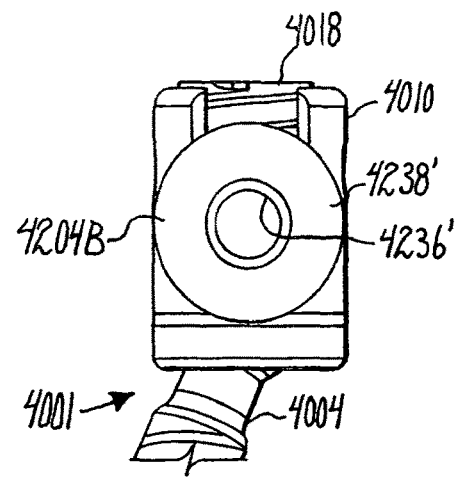

FIG. 149 is a partial front elevational view of the assembly of FIG. 148.

Figure 150:
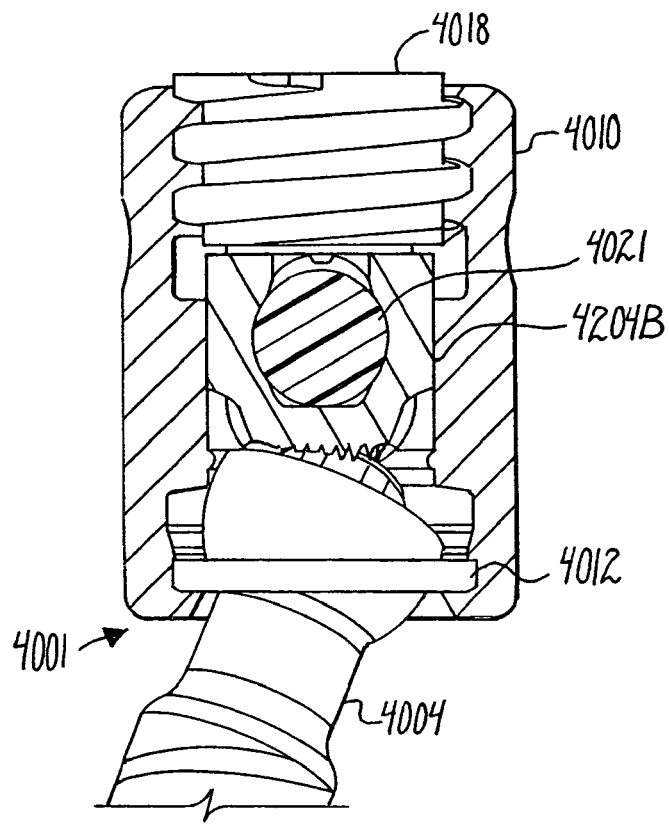

FIG. 150 is an enlarged and partial front elevational view, similar to FIG. 149 with portions broken away to show the detail thereof.

Figure 151:
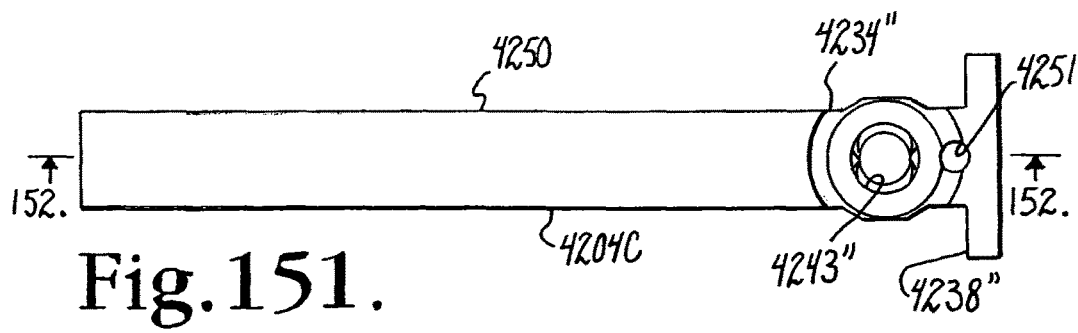

FIG. 151 is a top plan view of one of the sleeves illustrated in FIG. 141 that further includes an elongate rod.

Figure 152:
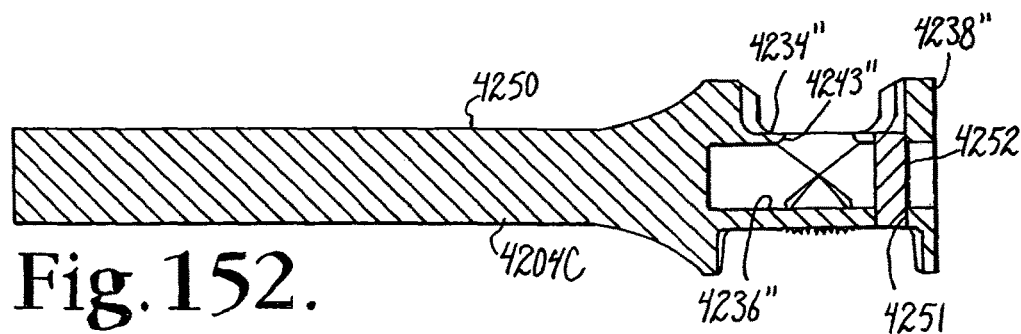

FIG. 152 is a cross-sectional view taken along the line 152-152 of FIG. 151.

Figure 153:
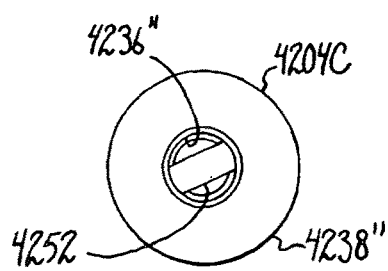

FIG. 153 is a front elevational view of the sleeve of FIG. 151.

Figure 154:
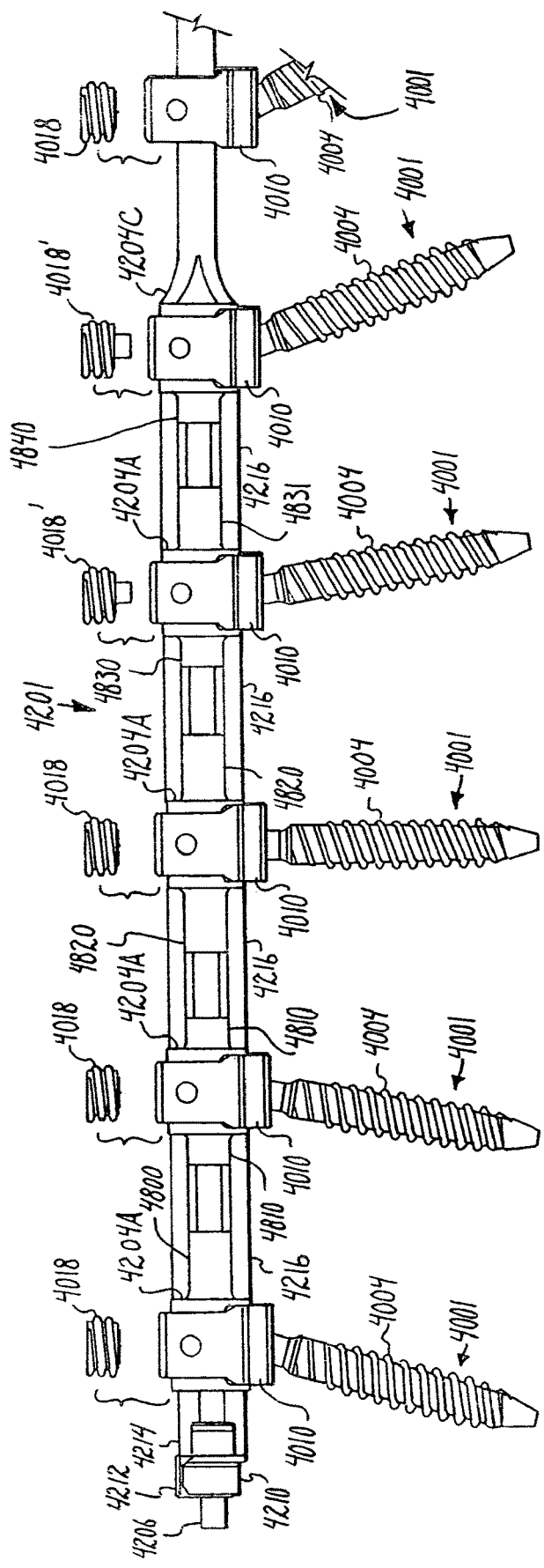

FIG. 154 is a reduced and partial and partially exploded side elevational view of a plurality of bone screws of FIG. 140 shown with various sleeves similar to that shown in FIG. 140, the sleeves having various lengths of tubal extensions thereon, and further shown with a sleeve similar to the sleeve of FIG. 151 and also a cord, bumper/blocker, spacers and various closure tops.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

Figure 1:
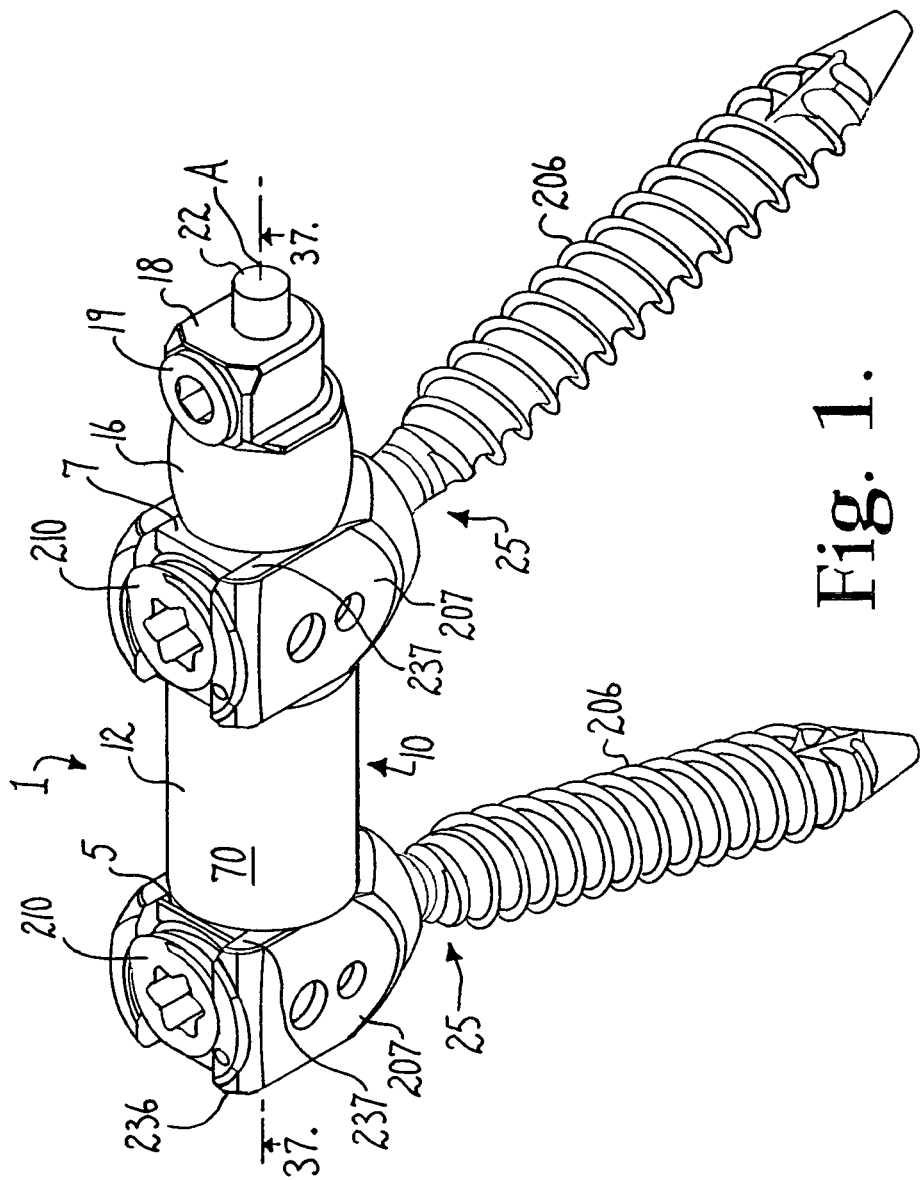
FIG. 1 is a perspective view of a longitudinal connecting member according to the invention having a tensioned cord and a pair of sleeves, each sleeve shown cooperating with a polyaxial bone screw.
Figure 1A:
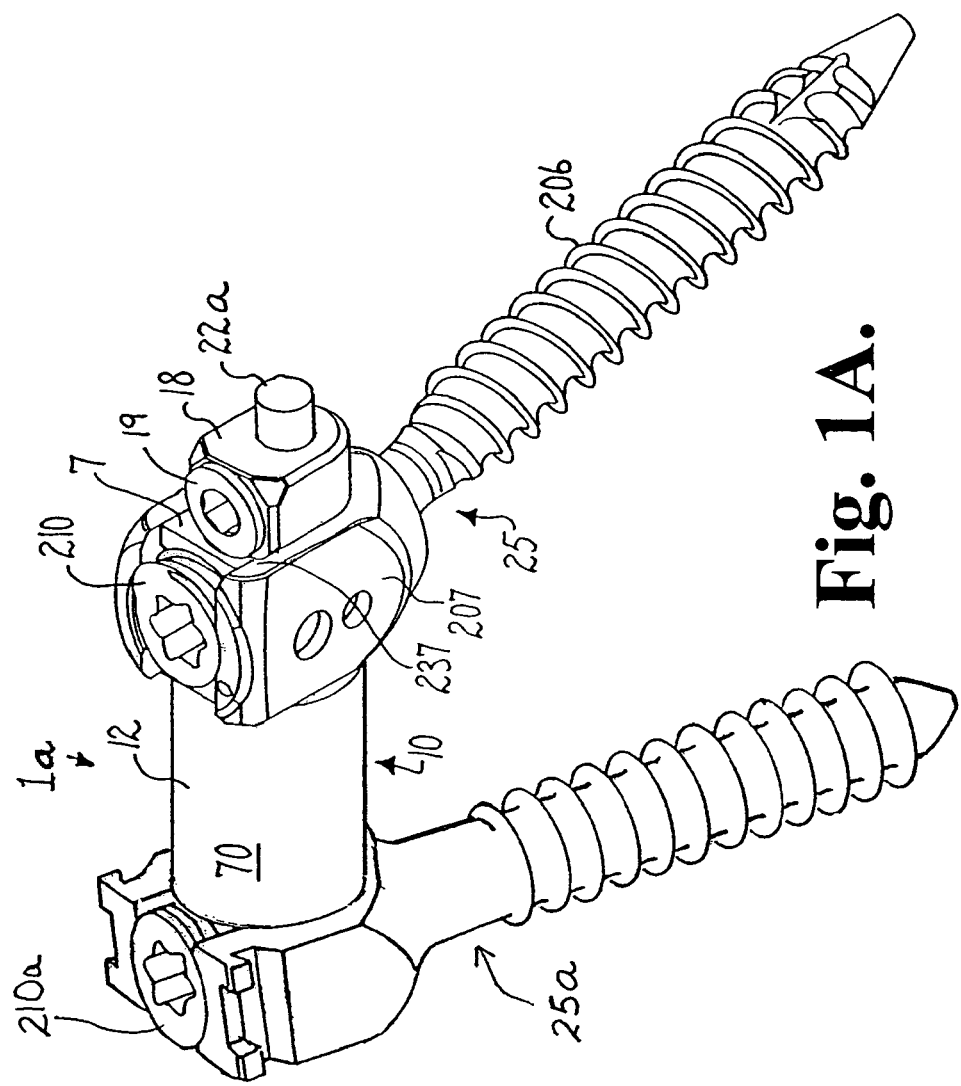
FIG. 1A is a perspective view of an alternative embodiment of a longitudinal connecting member according to the invention shown with one monoaxial screw clamped directly to an inner tensioned cord and one polyaxial screw having a sleeve for slidable engagement with the cord.
Figure 36:
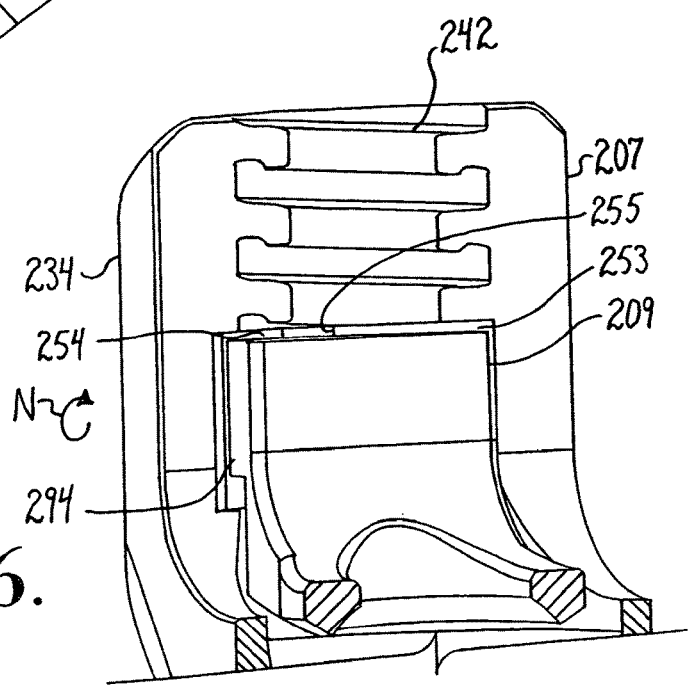
FIG. 36 is an enlarged and partial perspective view of the receiver and compression insert of FIG. 35 with portions broken away to show the detail thereof and shown in a later stage of assembly.
Figure 37:
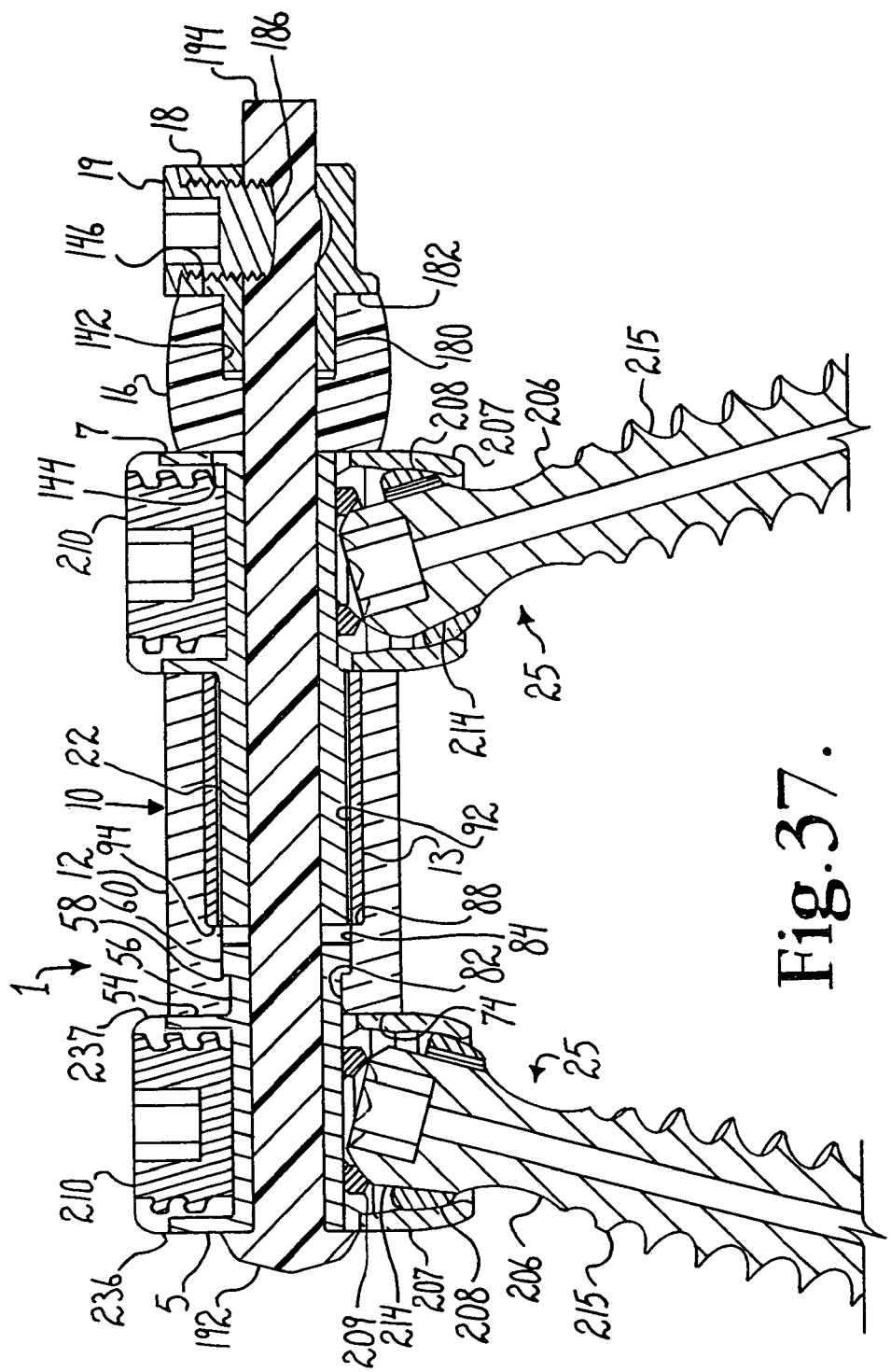
FIG. 37 is an enlarged and partial cross-sectional view taken along the line 37-37 of FIG. 1.
Figure 44:
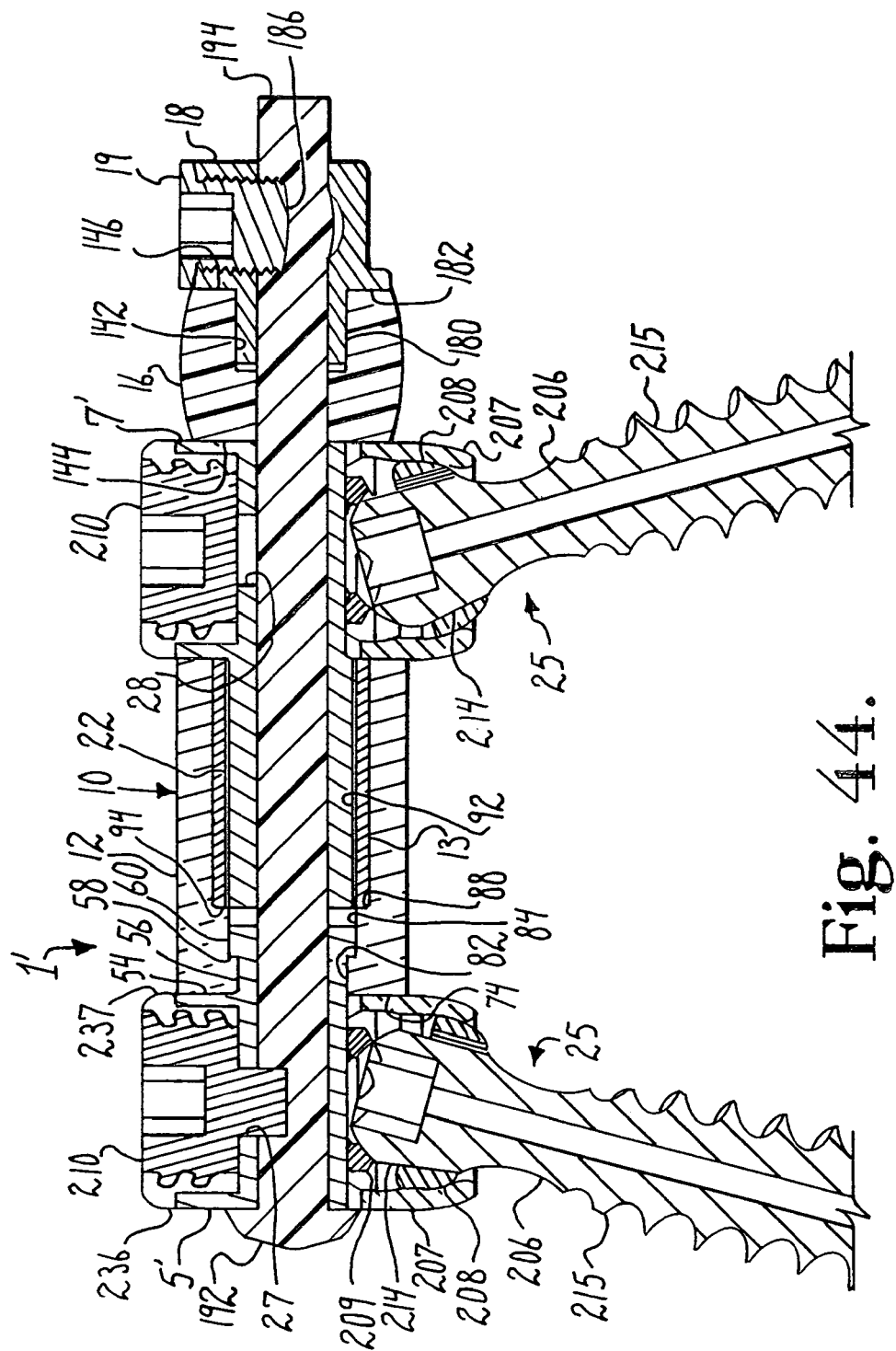
FIG. 44 is an enlarged and partial cross-sectional view, similar to FIG. 37, but showing an alternative assembly with sleeves having apertures for receiving closure top portions therein to grip the inner core.

With reference to FIGS. 1-44, the reference numeral 1 generally designates a non-fusion dynamic stabilization longitudinal connecting member assembly according to the present invention. The connecting member assembly 1 is elongate, having a substantially central axis A. With particular reference to FIGS. 1-4, the illustrated connecting member assembly 1 generally includes at least first and second hard, inelastic sleeves 5 and 7 with an optional spacer/liner combination, generally 10, located therebetween. In particular, the spacer/liner combination 10 includes an outer spacer 12 and an inner liner 13. The assembly 1 further includes an elastic bumper 16, a cord blocker 18 with cooperating set screw 19 and an inner core that in the present embodiment is a cord 22. The cord 22 extends along the axis A and successively through and within the sleeve 5, the spacer 12, the sleeve 7 (and optional spacer/liner 10), the bumper 16 and the cord blocker 18 as shown, for example, in FIG. 37. In FIGS. 1 and 37, the assembly 1 is shown attached to two polyaxial bone screws, generally 25 at the sleeves 5 and 7. A portion of the sleeve 7 extends into and through the spacer/liner 10 and is in slidable relationship therewith. A portion of the cord blocker 18 extends into a bore of the bumper 16. As will be described and explained in greater detail below, the bumper 16 is typically made from an elastomer while the outer spacer 12 is also elastomeric, but typically made from a material with a different durometer, being tougher and less compressible than the material of the bumper 16. Furthermore, the sleeves 5 and 7 and the spacer liner 13 are made from a hard, non-elastic material, such as a metal or metal alloy, like cobalt chromium. The hard and stiff sliding sleeve 7 includes an extension that slides into the liner 13, providing a dynamic no- or low-wear, sliding relationship between the sleeve 7 and the liner 13 that is non-binding, and provides excellent shear resistance while at the same time, the optional thin liner 13 cooperating with the elastomeric spacer 12 as well as the tensioned cord 22 provide controlled bending, with the tensioned cord 22 and compressed bumper 16, performing well under tension and compression. Portions of the sleeves 5 and 7 are disposed flush to side surfaces of the cooperating bone screws 25 that abut against the spacer 12 or the bumper 16, such flush surface geometry results in stable, secure substantially full contact between such outer elements of the assembly 1 and the cooperating bone screws. In certain embodiments of the invention, the sleeves 5 and 7 may further include respective openings 27 and 28 (shown in phantom in the drawings with the exception of FIG. 44) sized and shaped to receive a portion of a closure top therethrough for gripping the cord 22 when desired by the surgeon. Such openings 27 and 28 and cooperating closure tops will be described in greater detail below with respect to FIGS. 100-110 and 117-118, for example. With particular reference to FIG. 44, when a longitudinal connecting member according to the invention includes two or more sleeves 5' and/or 7' equipped with closure top receiving openings, the openings 27 and 28 allow a surgeon to decide whether to allow the cord 22 to slide or slip with respect to the particular sleeve 5' or 7' or to be gripped within such sleeve 5' or 7', advantageously providing for variable segmental stiffness along a length of a longitudinal connecting member, and thus custom-made for the needs of the individual patient. When sleeves 5' and 7' having respective openings 27 and 28 are utilized in a longitudinal connecting member, the bumper 16 and cord blocker 18/setscrew 19 combination is an optional component and thus may or may not be included in such a longitudinal connecting member assembly as the cord 22 may be fixed in place at a sleeve 5' or 7' located near an end of such assembly. It is noted that the sleeves 5 and 7 may also include tubular extensions of varying lengths on one or both sides thereof (not shown), but as otherwise shown and described with respect to other sleeves of the invention, for example, on FIG. 132. With reference to FIG. 1a, and as will be described in greater detail below, it is noted that sleeves 5 and 5' and 7 and 7' according to the invention may be used with or without a bumper 16, but may cooperate with one or more blockers 18. As stated elsewhere herein, connecting members of the invention may or may not include bumpers 16 or blockers 18. Furthermore, a single sleeve 5, 5', 7 or 7' (or other sleeves described herein) may be used in a longitudinal connecting member according to the invention, cooperating with one or more other bone anchors (mono- or polyaxial) that do not engage a sleeve, but rather fixedly or slidingly cooperate directly with the tensioned cord (also shown in FIG. 1a and described in greater detail below).

With particular reference to FIGS. 5-8, the sleeve 5 further includes a body portion 30 generally sized and shaped for being received within the polyaxial bone screw 25 and a tubular extension 32 sized and shaped to engage and hold the spacer 12 in fixed engagement with the sleeve 5. The illustrated body portion 30 and tubular extension 32 are integral or otherwise fixed to one another. A through bore 34 extends through a lower portion of the body portion 30 and centrally through the tubular extension 32. The bore 34 is sized and shaped to slidingly receive the cord 22 and when assembled with a remainder of the assembly 1 extends along the axis A. The body portion 30 includes an outer side and lower surface 36 that is substantially U-shaped in cross-section, being sized and shaped to fit within a U-shaped opening of the bone screw 25 as will be described in greater detail below. A substantial portion of the surface 36 terminates at an upper planar surface 38, with the U-shaped surface extending on either side of the planar surface 38 into upwardly extending arms or flanges 40 and 42. Inner surfaces 44 and 46 of the respective arms 40 and 42 form a discontinuous cylindrical wall sized and shaped to receive a closure top of the bone screw 25 as will be described in greater detail below. The planar surface 38 is also a seating surface for the bone screw closure top. As will be described in greater detail below, the arms 40 and 42 and the U-shaped body 36 are sized and shaped to fit within the receiver of the bone screw 25 and resist rotation and other forces placed on the sleeve 5. However, it is noted that in some embodiments, the sleeve 5 may be substantially cylindrical in outer form and thus receivable within a variety of fixed or polyaxial screw heads, such as will be described below with respect to FIGS. 45-95. In the embodiment illustrated in FIGS. 1-44, the arms 40 and 42 that are received within the polyaxial screw 25 terminate at respective upper planar surfaces 48 and 50. The arms 40 and 42 further include respective substantially planar outer or end surfaces 52 and 54, such surfaces being operatively flush with surfaces of the bone screw 25 as will be described more fully below. The outer surface 52 is also an end surface of the sleeve 5, extending from the arm 40 top surface 48 downwardly and around the bore 34 and running adjacent and perpendicular to the U-shaped outer surface 36. The surface 52 is adjacent to a flared or beveled surface 53 that defines an opening of the bore 34. The outer surface 54 is adjacent to a tapered surface 55 that extends toward and terminates at a first cylindrical surface 56 of the tubular extension 32. The outer cylindrical surface 56 terminates at a radially extending annular wall 58 that is perpendicular thereto. The wall 58 terminates at a second substantially cylindrical surface 60 of greater outer diameter than the cylindrical surface 56. The surface 60 terminates at an annular inwardly tapering beveled surface 62. The bevel 62 is adjacent to a planar annular end surface 64 that is disposed perpendicular to the cylindrical surface 60. The surface 64 is adjacent to a flared or beveled surface 65 that defines an opening of the bore 34. The surfaces 56, 58 and 60 provide a push-on connective element for attachment to inner surfaces of the spacer 12 as will be described in greater detail below. The sleeve 5, as well as the sleeve 7, the liner 13 and the cord blocker 18 with set screw 19 may be made from a variety of inelastic materials, including, but not limited to metals, metal alloys, including cobalt chromium, and inelastic plastics including, but not limited to plastic polymers such as polyetheretherketone (PEEK), ultra-high-molecular weight-polyethylene (UHMWP), polyurethanes and composites, including composites containing carbon fiber and layers of different materials.

With particular reference to FIGS. 4 and 13-17, the spacer 12 is substantially cylindrical and tubular in form, having an outer cylindrical surface 70 and an inner, graduated through bore, generally 72. The spacer 12 has opposed substantially planar annular end surfaces 74 and 76. The bore 72 is defined in part by a first inner cylindrical surface 78 that begins at the surface 76 and extends substantially along a length of the spacer 12. The surface 78 closely receives the inner liner 13 thereon. In fact, the spacer 12/liner 13 combination is typically assembled or manufactured with the liner 13 being fixed to the surface 78 such that a surgeon receives the spacer 12/liner 13 combination already assembled and ready for the surgeon to cut the spacer 12/liner 13 combination to a desired length near the end 76 as will be described in greater detail below. Adjacent the end 74, the spacer 12 includes a flared or beveled opening surface 80 extending to an inner cylindrical surface 82 having an inner diameter smaller than the cylindrical surface 78. A third inner cylindrical surface 84 is located between the surface 82 and the surface 78, the surface 84 having a diameter larger than the surface 82 and smaller than the surface 78. A curved transition surface 86 spans between the cylindrical surfaces 82 and 84 and a curved transition surface 88 spans between the cylindrical surfaces 84 and 78. Portions of the transition surfaces 86 and 88 are substantially perpendicular to the cylindrical surfaces 78, 82 and 84. As will be described in greater detail below, when the spacer 12/liner 13 combination is pushed onto the tubular extension 32 of the sleeve 5 during assembly, the flared surface 80 of the spacer engages the tapered surface 55 of the sleeve, the inner cylindrical surface 82 engages the outer cylindrical surface 56 of the sleeve, the surface 86 of the spacer engages the surface 58 of the sleeve, and the inner cylindrical surface 84 of the spacer engages the outer cylindrical surface 60 of the tubular extension 32. As best shown in FIG. 37, the close fit between the spacer inner cylindrical surfaces 82 and 84 and the tubular extension 32 of the sleeve 5, provide a secure, fixed positioning of the spacer 12 with respect to the sleeve 5 along the axis A, prohibiting the spacer 12 from being pulled away from the sleeve surface 54 during spinal movement. However, some relative rotational movement between the spacer 12 and the sleeve 5 about the axis A is possible, allowing for some twist or turn, providing some relief for torsional stresses. The spacer 12 is typically elastic and made from a plastic, for example, a thermoplastic elastomer made from a polyurethane or polyurethane blend, such as a polycarbonate urethane.

With particular reference to FIGS. 9-12, the optional inelastic liner 13 is substantially cylindrical and tubular in form, having an outer cylindrical surface 90 and an inner cylindrical through bore 92. The liner 13 has opposed annular end surfaces 94 and 96. As best shown in FIG. 37, the end surface 94 abuts against the annular surface 88 of the spacer 12 and the outer cylindrical surface 90 is adhered or otherwise fixed to the inner cylindrical surface 78 of the spacer 12. The end surface 96 is disposed flush to the end surface 76 of the spacer 12, these surfaces being the cut-to-length side of the spacer 12/liner 13 combination as will be described in greater detail below. As previously stated, although shown as a separate part or element in the drawings, when used, the optional liner 13 is typically provided pre-assembled within the spacer 12. The liner 13 may be made from a variety of non-elastic materials, including metals, metal alloys and some plastics, with cobalt chromium being a preferred material. The inner cylindrical surface 92 is sized and shaped to slidingly receive a tubular extension of the inelastic sleeve 7 as will be described in greater detail below.

With particular reference to FIGS. 18-22, the sleeve 7 includes a body portion 99 generally sized and shaped for being received within the polyaxial bone screw 25 and a tubular extension 100 sized and shaped to be slidingly received in the spacer 12/liner 13 combination. The illustrated body portion 99 and tubular extension 100 are integral or otherwise fixed to one another. More than one size of sleeve 7 is typically provided to the surgeon, the sleeves 7 differing only in the length of the tubular extension 100, so as to appropriately match the size of the patient's spine. A through bore 104 extends through a lower portion of the body portion 99 and centrally through the tubular extension 100. The bore 104 is sized and shaped to slidingly receive the cord 22 and when assembled with a remainder of the assembly 1 extends along the axis A. The body portion 99 includes an outer side and lower surface 106 that is substantially U-shaped in cross-section, being sized and shaped to fit within a U-shaped opening of the bone screw 25 as will be described in greater detail below. A substantial portion of the surface 106 terminates at an upper planar surface 108, with the U-shaped surface extending on either side of the planar surface 108 into upwardly extending arms or flanges 110 and 112. Inner surfaces 114 and 116 of the respective arms 110 and 112 form a discontinuous cylindrical wall sized and shaped to receive a closure top of the bone screw 25 as will be described in greater detail below. The planar surface 108 is also a seating surface for the bone screw closure top. As will be described in greater detail below, the arms 110 and 112 and the U-shaped body 106 are sized and shaped to fit within the receiver of the bone screw 25 and resist rotation and other forces placed on the sleeve 7. However, it is noted that in some embodiments, the sleeve 7 may be substantially cylindrical in outer form and thus receivable within a variety of fixed or polyaxial screw heads. In the illustrated embodiment, the arms 110 and 112 that are received within the polyaxial screw 25 terminate at respective upper planar surfaces 118 and 120. The arms 110 and 112 further include respective substantially planar outer or end surfaces 122 and 124, such surfaces being operatively flush with side surfaces of the bone screw 25 as will be described more fully below. The outer surface 124 is also an end surface of the sleeve 7, extending from the arm 112 top surface 120 downwardly and around the bore 104 and running adjacent and perpendicular to the U-shaped outer surface 106. The surface 124 is adjacent to a flared or beveled surface 125 that defines an opening of the bore 104. The outer surface 122 is adjacent to a tapered surface 126 that extends toward and terminates at a cylindrical surface 127 of the tubular extension 100. The outer cylindrical surface 127 extends toward an annular planar end surface 128 that is perpendicular thereto. A beveled surface 130 spans between the cylindrical surface 127 and the end surface 128. The end surface 128 terminates at an inner flared surface 131, the surface 131 defining an opening of the bore 104. Upon assembly with the spacer 12/liner 13 combination, the cylindrical surface 127 is in slidable relationship with the inner surface of the liner 13 defining the through-bore 92. As stated above, a desirable material for both the liner 13 and the tubular extension 100 is cobalt chromium. Furthermore, in some embodiments of the invention, in order to have low or no wear debris, the liner 13 inner surface and the outer surface 127 of the tubular extension 100 may be coated with an ultra thin, ultra hard, ultra slick and ultra smooth coating, such as may be obtained from ion bonding techniques and/or other gas or chemical treatments. It is further noted that inner surfaces of the sleeves 5 and 7 that receive the cord 22 may also be likewise coated to provide a slick, low to no wear debris interface with the cord 22.

With particular reference to FIGS. 4 and 23-26, the bumper 16 is substantially cylindrical and tubular in form, having an outer cylindrical surface 140 and an inner, graduated through bore, generally 142. The bumper 16 has opposed substantially planar annular end surfaces 144 and 146. The bore 142 is defined in part by a first inner cylindrical surface 148 that begins at the surface 146. The surface 148 closely receives a tubular extension of the cord blocker 18 as will be described in greater detail below. Adjacent the end 144, the bumper 16 includes a flared or beveled opening surface 150 extending to an inner cylindrical surface 152 having an inner diameter smaller than a diameter of the inner cylindrical surface 148. A curved transition surface 156 spans between the cylindrical surfaces 152 and 148. A substantial portion of the surface 156 is disposed perpendicular to the cylindrical surfaces 152 and 148. The bumper 16 is elastic and may be made from a variety of compressible and stretchable materials, including, but not limited to natural or synthetic elastomers such as polyisoprene (natural rubber), and synthetic polymers, copolymers, and thermoplastic elastomers, for example, polyurethane elastomers such as polycarbonate-urethane elastomers. In order to have low or no wear debris, the bumper 16 inner surface may also be coated with an ultra thin, ultra hard, ultra slick and ultra smooth coating, such as may be obtained from ion bonding techniques and/or other gas or chemical treatments.

With particular reference to FIGS. 27-30, the cord blocker 18 and cooperating set screw 19 are shown. The blocker 18 includes a body portion 159 and a tubular extension 160 sized and shaped to be slidingly received in the bumper 16 at the inner cylindrical surface 148. The illustrated body portion 159 and tubular extension 160 are integral or otherwise fixed to one another. A through bore 164 extends through a lower portion of the body portion 159 and centrally through the tubular extension 160. The bore 164 is sized and shaped to receive the cord 22 and when assembled with a remainder of the assembly 1 extends along the axis A. The body portion 159 includes an outer side and lower surface 166 that is substantially U-shaped in cross-section, however, the surface 166 may have a variety of outer geometries, including cylindrical or of other curved or polygonal cross-sections. The surface 166 terminates at an upper planar surface 168. Formed in the surface 168 is a threaded bore 170 sized and shaped to receive and threadably mate with the set screw 19. The threaded bore 170 communicates with the through bore 164 and is substantially perpendicular thereto. Near the intersection of the bore 164 and the threaded bore 170, a surface 172 partially defining the bore 164 includes a depression 174, sized and shaped for receiving the cord 22 therein when the set screw 19 engages the cord 22 as will be described in greater detail below. The blocker 18 further includes opposed substantially planar end surfaces 176 and 178. The end surface 176 is also the end surface of the tubular extension 160 that has an outer cylindrical surface 180. The end surface 178 is also the end surface of the body 159. The body further includes a substantially annular planar end surface 182 adjacent the tubular extension 160. In operation, the end surface 146 of the bumper 16 abuts against the end surface 182.

The set screw 19 includes a threaded body 184 having a concave or domed bottom surface 186 and a substantially cylindrical head 188. Formed in the cylindrical head 188 is an inner drive 189 sized and shaped to receive a driving tool for rotating and advancing the set screw 19 into the blocker 18 at the threaded bore 170. Specifically, the threaded body 184 mates under rotation with the threaded bore 170. The set screw 19 and blocker 18 are sized and shaped to have a limited travel or stop such that when the set screw 19 is rotated into the bore 170 and extends into the bore 164, the set screw 19 locks and cannot be advanced any further at a desired location wherein the cord 22 is frictionally held firmly and snugly in place between the domed bottom 186 and the concave or depressed surface 174 without damaging or destroying the cord 22.

With reference to FIG. 31*a*, it is noted that the blocker 18 and set screw 19 combination is typically provided with the bumper 16 pre-attached thereto and handled as a unit assembly. Thus, prior to being received by the surgeon, the bumper 16 is wedged and in some cases adhered or otherwise fixed onto the tubular extension 160 at the factory, with the surface 148 of the bumper frictionally engaging the surface 180 of the blocker 18 and the surface 146 of the bumper 16 abutting against and fixed to the surface 182 of the blocker 18.

Figure 4:
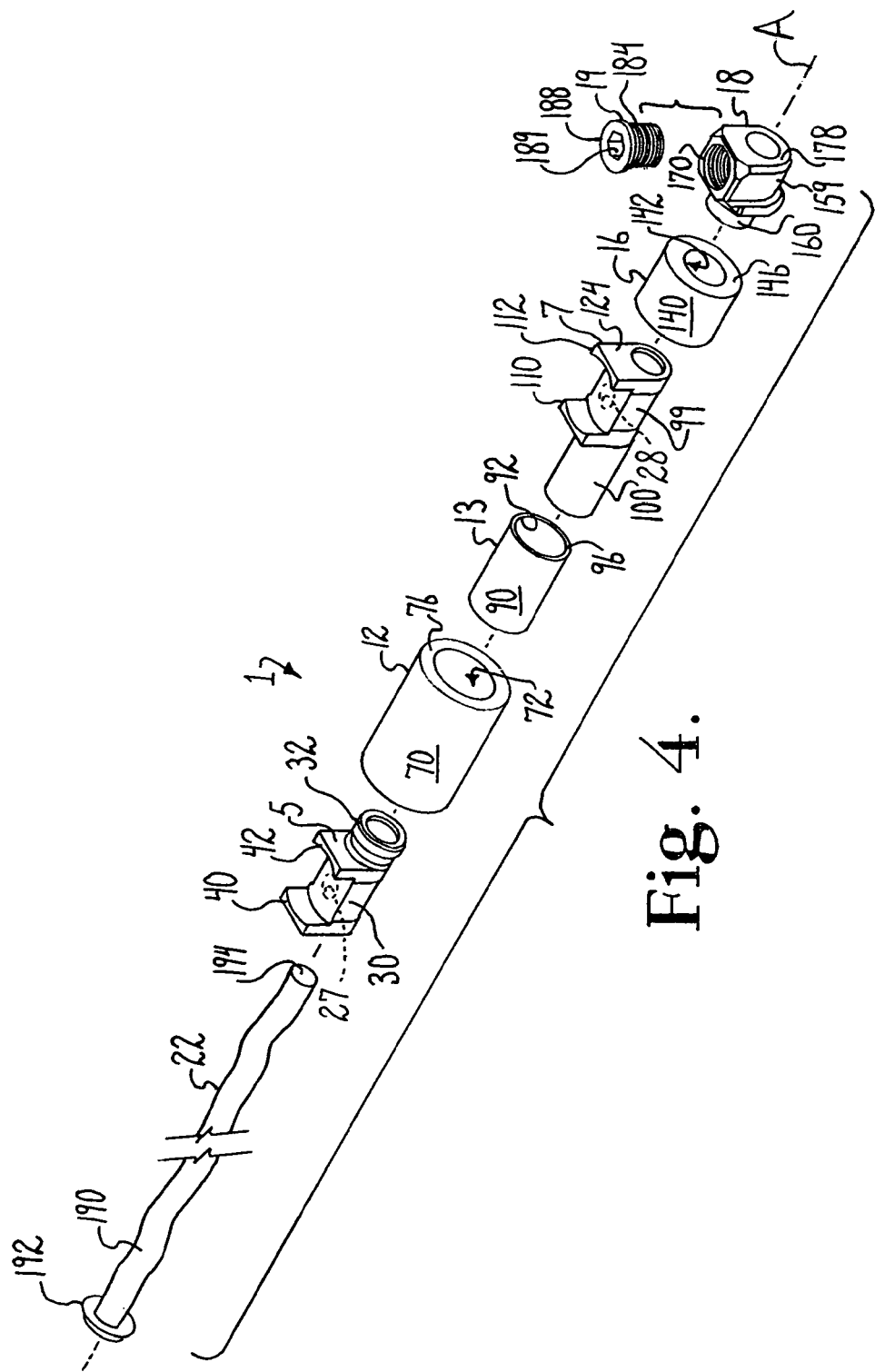
FIG. 4 is a reduced exploded view of the connecting member of FIG. 2.
Figure 9:
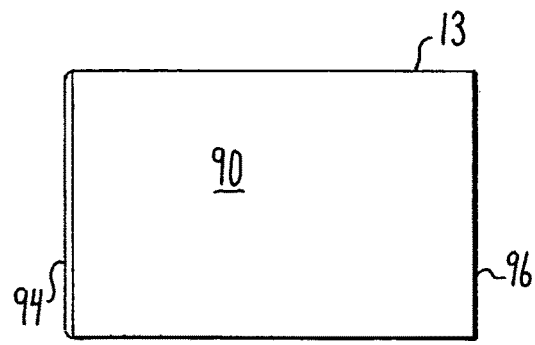
FIG. 9 is an enlarged side elevational view of the liner of the spacer/liner combination of FIG. 2.
Figure 12:
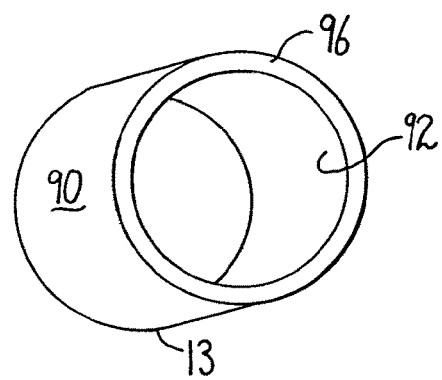
FIG. 12 is an enlarged perspective view of the liner of FIG. 9.
Figure 10:
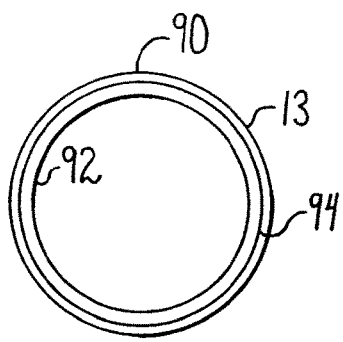
FIG. 10 is an enlarged rear elevational view of the liner of FIG. 9.
Figure 11:
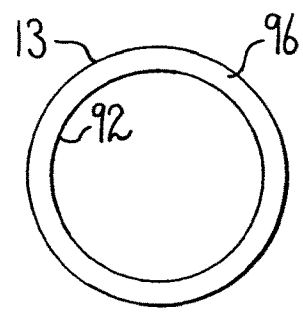
FIG. 11 is an enlarged front elevational view of the liner of FIG. 9.
Figure 23:
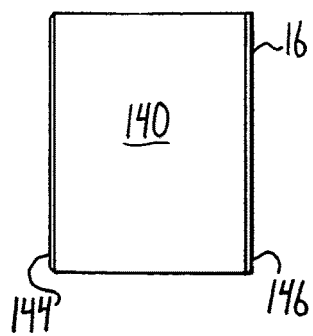
FIG. 23 is an enlarged side elevational view of the bumper shown in FIG. 2.
Figure 24:
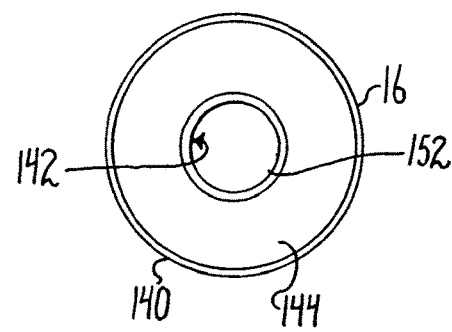
FIG. 24 is an enlarged rear elevational view of the bumper of FIG. 23.
Figure 25:
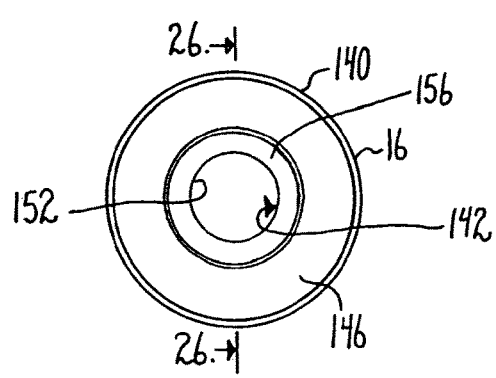
FIG. 25 is an enlarged front elevational view of the bumper of FIG. 23.
Figure 26:
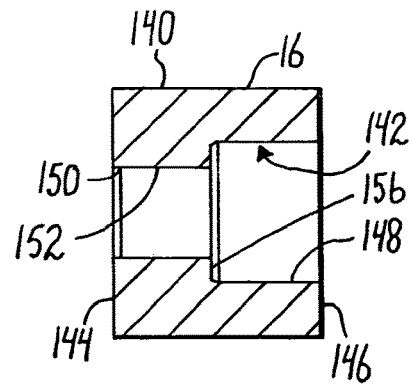
FIG. 26 is an enlarged cross-sectional view taken along the line 26-26 of FIG. 25.
Figure 27:
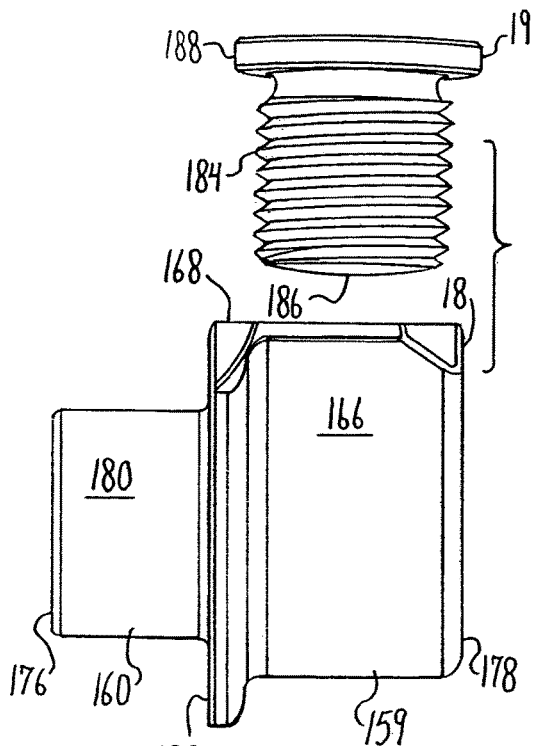
FIG. 27 is an enlarged side elevational view of the blocker and set screw shown in FIG. 2.
Figure 28:
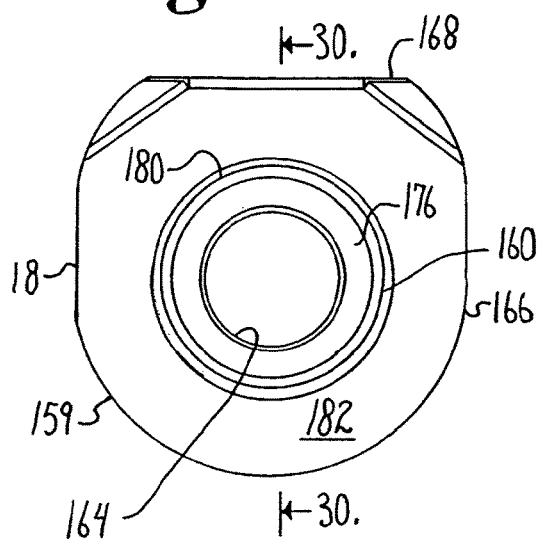
FIG. 28 is an enlarged rear elevational view of the blocker of FIG. 27.
Figure 29:
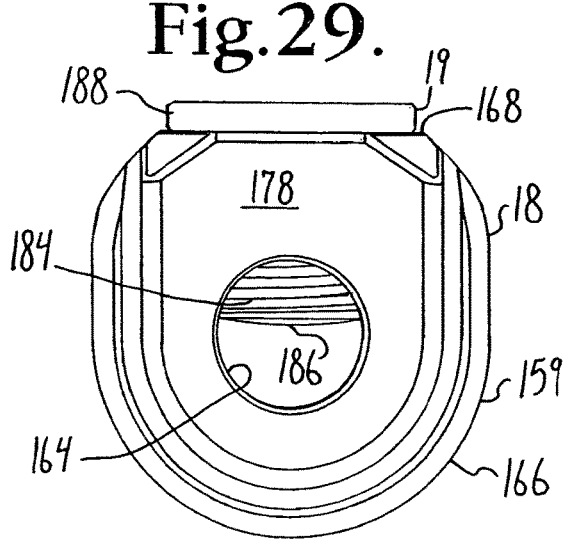
FIG. 29 is an enlarged front elevational view of the blocker and set screw of FIG. 27.
Figure 31:
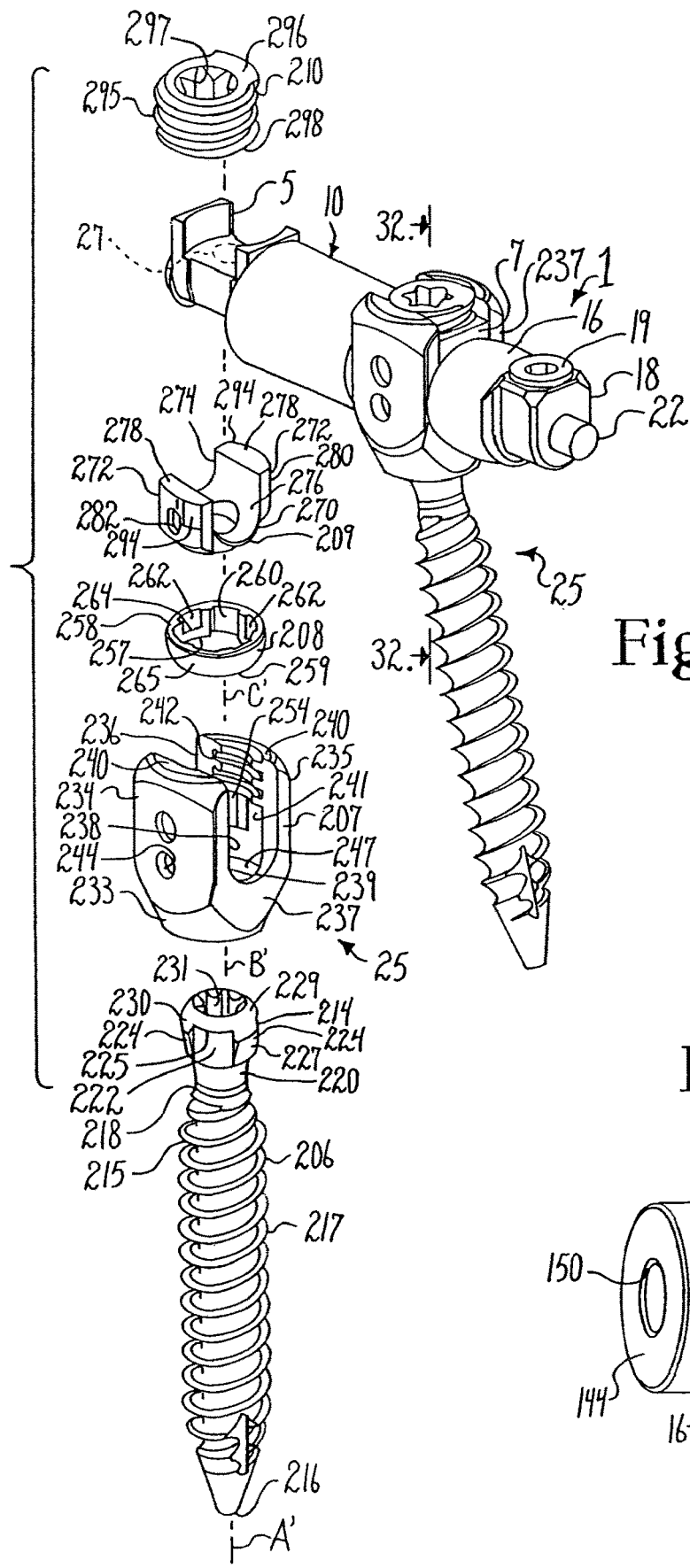
FIG. 31 is an enlarged and partial perspective view of the connector and bone screws of FIG. 1 further showing a first bone screw in exploded view, the bone screw including a bone screw shank, retainer, receiver, compression insert and closure top.

With particular reference to FIG. 4, the illustrated cord 22 includes an elongate body 190 with an enlarged end 192 and an opposed cut-to-length end 194. The enlarged end 192 may be created by heating the cord 22 to melt the cord and create the enlarged end 192 that abuts against the surface 52 of the sleeve 5 and is too large to enter the bore 34. Alternatively an outer pin or knob (not shown) may be fixed to the cord 22. In other embodiments of the invention a blocker and set screw combination, similar to the blocker 18 and set screw 19 may be used to fix the cord 22 outside of the sleeve 5 and thus allow the cord 22 to be in slidable relationship with the sleeve 5. The cord 22 may be made from a variety of materials, including polyester or other plastic fibers, strands or threads, such as polyethyleneterephthalate. A cord according to the invention typically does not illustrate elastic properties, such as any significant additional axial distraction and lengthening after the assembly 1 is operatively assembled and the cord is tensioned. However, it is foreseen that in some embodiments, the cord 22 may be made of an elastic or semi-elastic material, such as a plastic or rubber (natural or synthetic) having at least some elastic properties, allowing for some further distraction of the assembly 1 during operation thereof.

With particular reference to FIGS. 31-37 the reference number 25 generally represents a polyaxial bone screw apparatus or assembly in accordance with the present invention operably utilized by implantation into a vertebra (not shown) and in conjunction with the connecting member assembly 1 of the invention. The bone anchor assembly 25 generally includes a shank 206, a receiver 207, a retainer structure or ring 208, a lower pressure insert 209 and a closure structure or top 210.

The shank 206 is elongate and has an upper body portion 214 integral with a lower body portion 215, ending in a tip 216. The shank body 215 has a helically wound bone implantable thread 217 extending from near the tip 216 to near the top 218 of the lower body 215 and extending radially outward therefrom. During use, the body 215 utilizing the thread 217 is implanted into a vertebra. The shank 206 has an elongated axis of rotation generally identified by the reference letter A'.

Axially extending outward and upward from the shank body 215 is a neck 220, typically of reduced radius as compared to the adjacent top 218 of the body 215. Further extending axially and outwardly from the neck 220 is the shank upper portion 214 operably providing a connective or capture structure free from the bone or vertebra for joining with the receiver 207. The shank upper portion or capture structure 214 has a radially outer cylindrical surface 222. The cylindrical surface 222 has at least one non-helically wound and radially outward extending projection or spline 224 that extends beyond the surface 222. In the embodiment shown, the shank upper portion 214 has three such splines 224. It is noted that bone anchors of the invention have at least one and up to a plurality of splines 224. Preferably, the bone anchor includes from one to four splines. The splines 224 are located near and extend outwardly from an upper edge 225 of the shank upper portion cylindrical surface 222 and are equally circumferentially centered and spaced thereabout so as to be centered at approximately 120 degree intervals relative to each other. Each of the splines 224 has a substantially triangular shaped profile and a front wedge forming face 227 that slopes downwardly and radially inwardly from near the upper edge 225. Adjacent the upper edge 225 is a centrally located, axially extending and upwardly directed convex annular projection or dome-shaped upper end 229 that is centrally radiused. Each of the splines 224 includes an upper surface 230 that is adjacent to and extends from the upper end surface 229, having the same radius as the upper end surface 229. Also formed in the shank upper portion 214 within an annular rim 228 of the end surface 229 is a tool engagement aperture 231 for engagement by a tool driving head (not shown) that is sized and shaped to fit into the aperture for both driving and rotating the shank 206 into a vertebra. In the illustrated embodiment, the aperture 231 is star-shaped and runs parallel to the axis A'. It is foreseen that various sizes, shapes and numbers of apertures, slots or the like may be utilized in accordance with the invention for engaging a driving tool of suitable and similar mating shape. The illustrated shank 206 is cannulated, having a through bore extending an entire length of the shank 206 along the axis A'. The bore is defined by an inner cylindrical wall of the shank 206 and has a circular opening at the shank tip 206 and an upper opening communicating with the internal drive feature 231. The bore provides a passage through the shank 206 interior for a length of wire (not shown) inserted into the vertebra (not shown) prior to the insertion of the shank body 215, the wire providing a guide for insertion of the shank body 215 into the vertebra (not shown).

To provide a biologically active interface with the bone, the threaded shank body 215 may be coated, cannulated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bioceramic calcium phosphate coatings include, but are not limited to: alpha-tri-calcium phosphate and beta-tri-calcium phosphate $(Ca_3(PO_4)_2$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

The receiver 207 has a generally squared-off U-shaped appearance with a partially cylindrical inner profile and a substantially faceted outer profile; however, the outer profile could also include other geometrical configurations. Side surfaces of the receiver 207 that engage the spacer 12 and/or the bumper 16 are preferably planar. A receiver axis of rotation B' is aligned with the axis of rotation A' of the shank 206 during assembly of the receiver 207 with the shank 206 and the retainer 208. After the receiver 207 is pivotally connected to the shank 206, and such assembly is implanted in a vertebra (not shown), the axis B' is typically disposed at an angle with respect to the axis A' of the shank 206.

The receiver 207 has a base 233 with a pair of upstanding arms 234 and 235 forming a U-shaped channel 238 between the arms 234 and 235 having a lower seat 239. Opposed planar side surfaces 236 and 237 define the channel 238 and extend upwardly from the base 233 and to top surfaces 240 of the arms. The insert 209 that is disposed within the receiver 207 is sized and shaped to closely receive the sleeve 5 or the sleeve 7 at the respective U-shaped surfaces 36 and 106. When assembled, the sleeve arms 40 and 42 and 110 and 112 lie flush with the side surfaces 236 and 237, advantageously providing a full support for the spacer 12 and/or the bumper 16 at abutting ends thereof. Each of the arms 234 and 235 has an interior surface 241 that includes a partial helically wound guide and advancement structure 242. In the illustrated embodiment, the guide and advancement structure 242 is a partial helically wound flangeform that mates under rotation with a similar structure on the closure top 210, as described below. However, it is foreseen that the guide and advancement structure 242 could alternatively be a buttress thread, a reverse angle thread or other thread like or non-thread like helically wound advancement structures for operably guiding under rotation and advancing the closure top between the arms 234 and 235. Also, non-helically wound closure tops or caps are foreseen. Tool engaging apertures 244 are formed on the outsides of the arms 234 and 235 for holding the receiver 207 during certain assembly steps and/or implantation of the assembly and also for access to a thin deformable wall 245 during assembly with the pressure insert 209.

A chamber or cavity 247 is located within the receiver base 233 that opens upwardly into the U-shaped channel 238. The cavity 247 includes a partial spherical shaped surface 248, at least a portion of which forms a partial internal hemispherical seat for the retainer 208, as is described further below. A lower neck 250 defining a lower bore further communicates between the cavity 247 and the bottom exterior of the base 233 and is coaxial with the rotational axis B' of the receiver 207. The neck 250 at least partially defines a restriction having a radius which is smaller than the radius of the retainer 208, so as to form a restrictive constriction at the location of the neck 250 relative to the retainer 208 to prevent the retainer 208 from passing between the cavity 247 and the lower exterior of the receiver 207. In an upper portion of the cavity 247, is a substantially cylindrical surface 252 that includes a run-out surface 253 located directly beneath the guide and advancement structure 242. With particular reference to FIGS. 33-36, formed in the surface 253 under the structure 242 of both of the arms 234 and 235 is a recess 254 partially defined by a stop or abutment wall 255. As will be described in greater detail below, the cooperating compression insert 209 includes a protruding structure 294 on each arm thereof that abuts against the respective wall 255 of each of the receiver arms, providing a centering stop when the insert 209 is rotated into place as will be described below.

The retainer 208 is substantially ring-shaped and has an operational central axis which is the same as the elongate axis A' associated with the shank 206, but when the retainer 208 is separated from the shank 206, the axis of rotation is identified as axis C'. The retainer 208 has a central bore 257 that passes entirely through the retainer 208 from a top surface 258 to a bottom surface 259 thereof. The bore 257 is sized and shaped to fit snugly, but slidably over the shank capture structure cylindrical surface 222 in such a manner as to allow sliding axial movement therebetween under certain conditions, as described below. Three axially aligned channels 260 are spaced from the axis C' and extend radially outward from the bore 257 and into the wall of the retainer 208 so as to form three top to bottom grooves or slots therein. Backs of the channels 260 are the same radial distance from the axis C' as the distance the outermost portion of the splines 224 extend from the axis A' of the shank 206. The channels 260 are also circumferentially angularly spaced equivalent to and have a width that corresponds with the splines 224. In this manner, the shank upper portion 214 can be uploaded into the retainer 208 by axially sliding the shank upper portion 214 through the retainer 208 central bore 257 whenever the splines 224 are aligned with the channels 260 or are in an aligned configuration. The details of assembly and subsequent cooperation between the shank 206, the retainer 208 and the receiver 207 are similarly described in Applicant's U.S. Pat. No. 6,716,214 issued Apr. 6, 2004, the entire disclosure of which is incorporated by reference herein.

The retainer 208 also has three capture partial slots, receivers or recesses 262 which extend radially outward from the upper part of the bore 257 and that do not extend the entire length from top to bottom of the retainer 208, but rather only open on the top surface 258 and extend partly along the height of the retainer 208 thereof. The recesses 262 are sized and positioned and shaped to receive the splines 224 from above when the splines 224 are in a non-aligned configuration relative to the channels 260. That is, each of the recesses 262 has a width that approximates the width of the splines 224 and has a mating wedge engaging surface 264 that is shaped similar to the spline wedge forming faces 227, so that the splines 224 can be slidably received into the recesses 262 from above by axially translating or moving the shank 206 downward relative to the retainer ring 208 when the splines 224 are positioned above the recesses 262 in a recess aligned configuration. In some embodiments, the wedge engaging faces 264 slope slightly greater than the wedge forming faces 227 on the splines 224 so that there is additional outward wedging that takes place when the splines 224 are urged downwardly into the recesses 262.

In this manner the shank upper portion 214 can be uploaded or pushed upwardly through the retainer central bore 257 so as to clear the top 258 of the retainer ring 208, rotated approximately 60 degrees and then downloaded or brought downwardly so that the splines 224 become located and captured in the recesses 262. Once the splines 224 are seated in the recesses 262 the shank 206 cannot move further axially downward relative to the retainer ring 208. Preferably, the retainer 208 is constructed of a metal or other material having sufficient resilience and elasticity as to allow the retainer 208 to radially expand slightly outward by downward pressure of the splines 224 on the recesses 262 under pressure from structure above, as will be discussed further below. This produces a slight outward radial expansion in the retainer ring 208 at the location of the recesses 262.

The retainer 208 has a radially outer partial hemispherical shaped surface 265 sized and shaped to mate with the partial spherical shaped surface 248 and having a radius approximately equal to a radius associated with the surface 248. The retainer 208 radius is substantially larger than the radius associated with the annular curved surface 229 of the shank upper portion 214 and also substantially larger than the radius of the receiver neck 250.

The lower compression or pressure insert 209 includes a substantially cylindrical body 270 integral with a pair of upstanding arms 272. The body 270 and arms 272 form a generally U-shaped, open, through-channel 274 having a lower seat 276 sized and shaped to closely, snugly engage the sleeve 5 or the sleeve 7. The arms 272 disposed on either side of the channel 274 extend outwardly from the body 270. The arms 272 are sized and configured for placement near the run-out 253 below the guide and advancement structure 242 at the receiver inner arms 234 and 235. Each of the arms 272 includes a top surface 278 ultimately located directly beneath the guide and advancement structure 242, but are not directly engaged by the closure top 210. However, in some embodiments of the bone screw for use with other longitudinal connecting members, the closure top may directly engage the top surfaces 278 for locking the polyaxial mechanism of the assembly 25. Therefore, the assembly 1 may be used with a wide variety of longitudinal connecting members, including the sleeves 5 and 7 or rods or other connecting members that engage the closure top 210 and are locked into position by such closure top 210 as well as rods of smaller diameter or, for example cords that are captured by the closure top 210, but are otherwise movable within the receiver 207 and are thus in slidable or spaced relation with the closure top 210. Each arm 272 further includes a partially cylindrical outer surface 280 sized and shaped to fit within the receiver 207 at the guide and advancement structure 242 run-out relief 253. The cylindrical surfaces 280 are disposed substantially perpendicular to the respective adjacent top surfaces 278. In some embodiments of the invention recesses are formed near and/or at the top surfaces 278 and the surfaces that form the channel 274 to provide relief for material flow of the longitudinal connecting member, when, for example, the connector is made from a deformable plastic. For example, a recessed surface or groove may be directed downwardly and inwardly toward the channel 274. Each of the outer surfaces 280 further includes a recess 282 sized and shaped to receive holding tabs or crimped material from the receiver 207. For example, the thin walls 245 of the receiver 207 are pressed into the recesses 282 to prevent counter-clockwise rotation of the insert 209 about the axis B' with respect to the receiver 207. In other embodiments of the invention, the receiver 207 may be equipped with spring tabs that snap into the recesses 282 to hold the insert 209 in place with respect to counter-clockwise rotation. The recesses 282 are preferably oval or elongate such that some desirable upward and downward movement of the insert 209 along the axis B' of the receiver 207 is not prohibited. As previously described herein the compression insert 209 arms each include the protruding structure 294 located on opposite sides of the arms such that when the insert 209 is dropped down into the receiver 207 as shown by the arrow M in FIG. 35 and then rotated into place in a clockwise direction as shown by the arrow N in FIG. 36, the structure 294 abuts the wall 255 of the recessed area 254 when the insert is in a desired centered location with the apertures 282 in alignment with the apertures 244.

The compression insert 209 further includes an inner cylindrical surface 284 that forms a through bore sized and shaped to receive a driving tool (not shown) therethrough that engages the shank drive feature 231 when the shank body 215 is driven into bone. The inner surface 284 runs between the seating surface 276 and an inner curved, annular, radiused or semi-spherical surface 286. The surface 286 is sized and shaped to slidingly and pivotally mate with and ultimately fix against the annular domed surface 229 of the shank upper portion 214. Thus, a radius of the surface 286 is the same or substantially similar to the radius of the surface 229. The surface 286 may include a roughening or surface finish to aid in frictional contact between the surface 286 and the surface 229, once a desired angle of articulation of the shank 206 with respect to the receiver 207 is reached. Adjacent to the inner surface 286 is a bottom rim or edge 288. Adjacent to the outer cylindrical surface 280 of the arms 272 is a substantially frusto-conical surface 290 that extends inwardly toward the lower rim 88. The surface 290 includes portions of the arms 272 as well as partially defining the pressure insert body 270.

Figure 35:
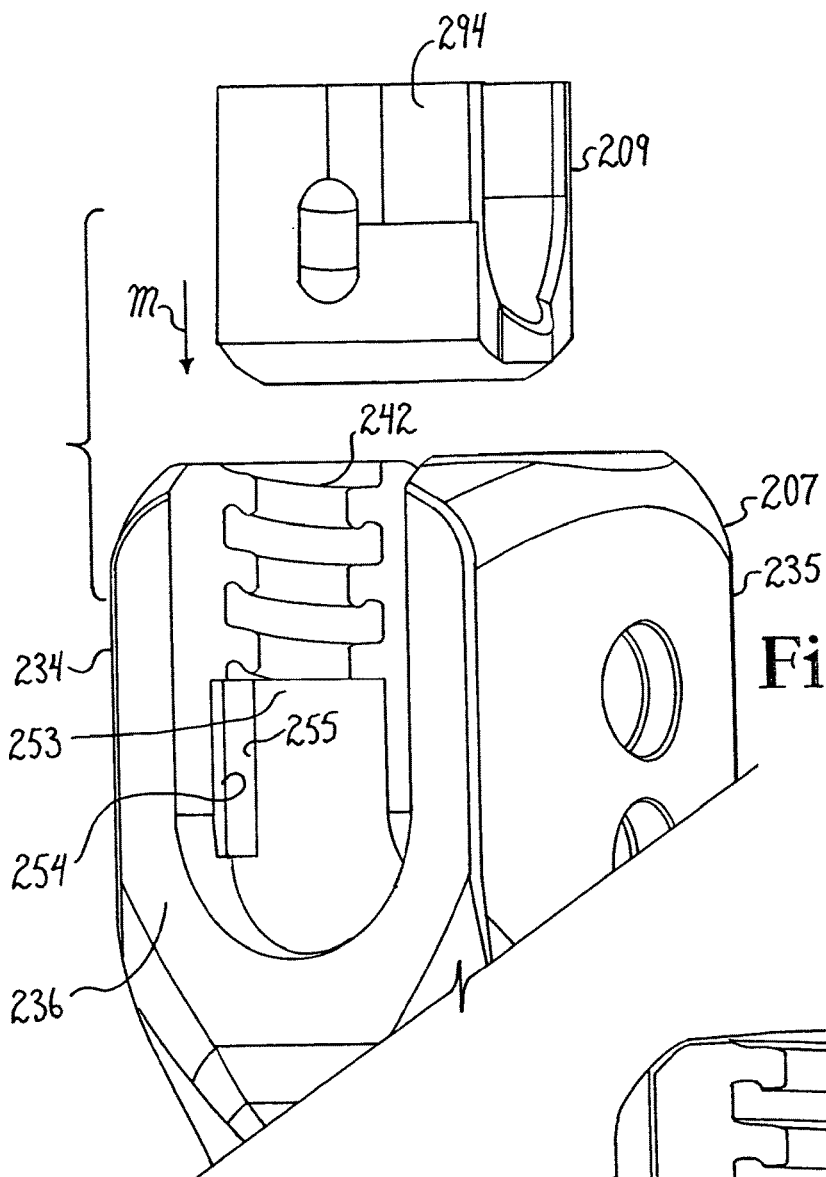
FIG. 35 is an enlarged and partial perspective exploded view of the receiver and compression insert of the first bone screw of FIG. 31, shown in an initial stage of assembly.

The pressure inset body 270 located between the arms 272 has an outer diameter slightly smaller than a diameter between crests of the guide and advancement structure 242 of the receiver 207 allowing for top loading of the compression insert 209 into the receiver 207 through the U-shaped channel 238, with the arms 272 being located between the arms 234 and 235 during insertion of the insert 209 into the receiver 207 (see FIG. 35). As explained above, once located between the guide and advancement structure 242 and the shank upper portion 214, the insert 209 is rotated into place about the axis B' until the arms 272 are directly below the guide and advancement structure 242 at or near the run-out 253 and the structure 294 abuts against the wall 255 of the recess 254. After the insert 209 is rotated into such position, a tool (not shown) may be inserted into the receiver apertures 244 to press the thin receiver walls 245 into the insert recesses 282. The lower compression insert 209 is sized such that the insert 209 is ultimately received within the cylindrical surface 252 of the receiver 207 below the guide and advancement structure 242. The receiver 207 fully receives the lower compression insert 209 and blocks the structure 209 from spreading or splaying in any direction. It is noted that assembly of the shank 206 with the retainer 208 within the receiver 207, followed by insertion of the lower compression insert 209 into the receiver 207 are assembly steps typically performed at the factory, advantageously providing a surgeon with a polyaxial bone screw with the lower insert 209 already held in alignment with the receiver 207 and thus ready for insertion into a vertebra.

The compression or pressure insert 209 ultimately seats on the shank upper portion 214 and is disposed substantially in the upper cylindrical portion 252 of the cavity 247, with the receiver deformable walls 245 engaging the insert 209 at the recesses 282, thereby cooperating with the walls 255 of the recesses 254 to hold the insert 207 in desired alignment.

The closure structure or closure top 210 can be any of a variety of different types of closure structures for use in conjunction with the present invention with suitable mating structure on the upstanding arms 234 and 235. In the embodiment shown, the closure top 210 is rotatably received between the spaced arms 234 and 235 of the receiver 207. The illustrated closure structure 210 is substantially cylindrical and includes an outer helically wound guide and advancement structure 295 in the form of a flange form that operably joins with the guide and advancement structure 242 of the receiver 207. The flange form utilized in accordance with the present invention may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 210 downward between the arms 234 and 235 and having such a nature as to resist splaying of the arms 234 and 235 when the closure structure 210 is advanced into the channel 238. The illustrated closure structure 210 also includes a top surface 296 with an internal drive 297 in the form of an aperture that is illustrated as a star-shaped internal drive, but may be, for example, a hex-shaped drive or other internal drives, including, but not limited to slotted, tri-wing, spanner, two or more apertures of various shapes, and the like. A driving tool (not shown) sized and shaped for engagement with the internal drive 297 is used for both rotatable engagement and, if needed, disengagement of the closure 210 from the receiver arms 234 and 235. It is also foreseen that the closure structure 210 may alternatively include a break-off head designed to allow such a head to break from a base of the closure at a preselected torque, for example, 70 to 140 inch pounds. Such a closure structure would also include a base having an internal drive to be used for closure removal. A bottom surface 298 of the closure top 210 is planar and is sized and shaped to mate with the sleeve 5 or the sleeve 7 at respective planar surfaces 38 and 108.

The closure top 210 may further include a cannulation through bore extending along a central axis thereof and through a surface of the drive 297 and the bottom surface 298. Such a through bore provides a passage through the closure 210 interior for a length of wire (not shown) inserted therein to provide a guide for insertion of the closure top into the receiver arms 234 and 235.

When the polyaxial bone screw assembly 201 is placed in use in accordance with the invention the retainer 208 is normally first slid through the receiver U-shaped channel 238 and into and seated in the receiver cavity 247. Thereafter, the retainer 208 is rotated 90 degrees so as to be coaxial with the receiver 207 and so that the retainer outer surface 265 snugly, but slidably mates with the receiver interior spherical shaped surface 248. The retainer 208 in the receiver 207 is then slid over the shank upper portion 214 so that the splines 224 slide upwardly through and above respective channels 260 so that the splines 224 are then located, at least partially, in the U-shaped channel 238 and chamber 247 above the retainer ring 208. The shank 206 is then rotated 60 degrees relative to the receiver about the axis A' and the translational direction of the shank 206 is reversed so that it goes downwardly or axially with respect to the receiver 207, and the splines 224 enter the recesses 262. At this point there is no substantial outward or downward pressure on the retainer 208 and so the retainer 208 is easily rotatable along with the shank 206 within the chamber 247 and such rotation is of a ball and socket type wherein the angle of rotation is only restricted by engagement of the neck 220 with the neck 250 of the receiver 207.

Then, the insert 209 is inserted into the channel 238 with the arms 272 aligned in the channel 238 between the guide and advancement structures 242. The insert 209 is then moved downwardly in the channel 238 and toward the cavity 247. With reference to FIGS. 35-36, once the arms 272 are located generally below the guide and advancement structure 242 and adjacent the run-out relief 253, the insert 209 is rotated 90 degrees in a clockwise direction about the axis B' of the receiver 207. The arms 272 fit within the cylindrical walls 252 above the cavity 247. Once the structures 294 abut against the walls 255, the arms 272 are desirably located directly below the guide and advancement structures 242, rotation is ceased and a tool (not shown) is used to press the thin walls 245 of the receiver 207 into the recesses 282 of the insert 209. The insert 209 is now locked into place inside the receiver 207 with the guide and advancement structures 242 prohibiting upward movement of the insert out of the channel 238.

Figure 32:
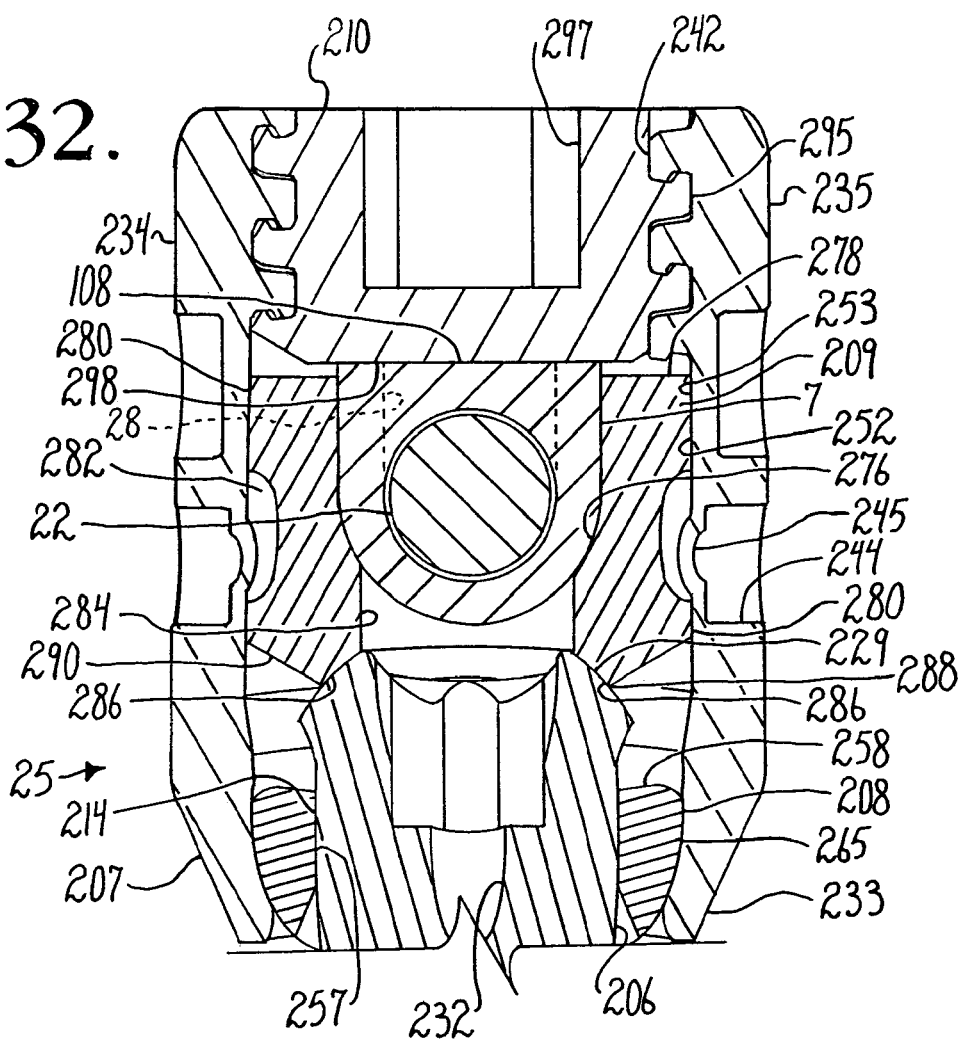
FIG. 32 is an enlarged and partial cross-sectional view taken along the line 32-32 of FIG. 31.
Figure 33:
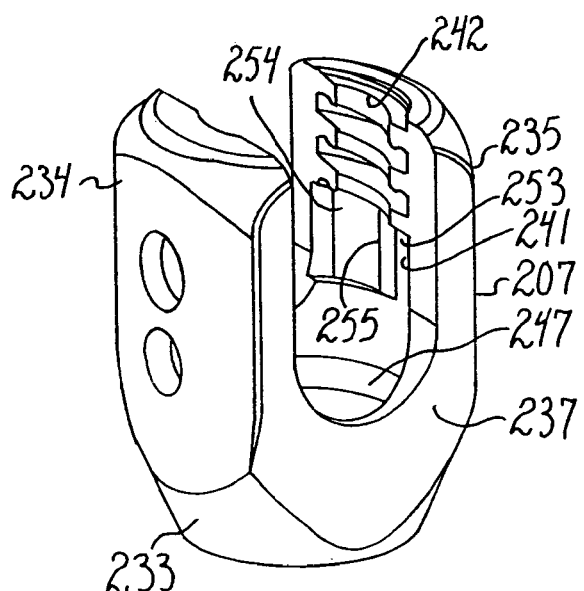
FIG. 33 is an enlarged perspective view of the receiver of the first bone screw of FIG. 31.
Figure 34:
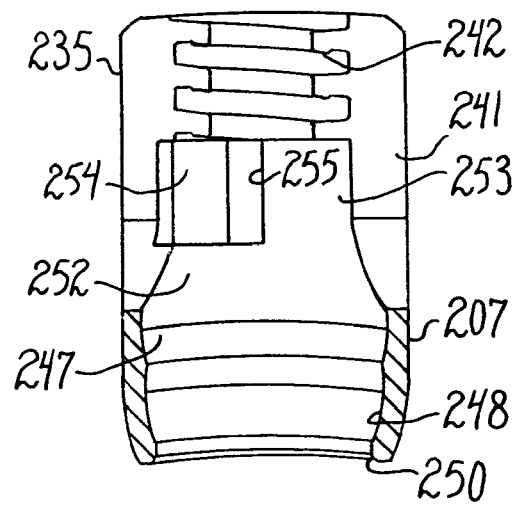
FIG. 34 is an enlarged side elevational view of the receiver of FIG. 33 with portions broken away to show the detail thereof.

As illustrated in FIGS. 32 and 37, the insert 209 seats on the shank upper portion 214 with the surface 286 in sliding engagement with the surface 229. The run-out or relief 253 is sized and shaped to allow for some upward and downward movement of the insert 209 toward and away from the shank upper portion 214 such that the shank 206 is freely pivotable with respect to the receiver 207 until the closure structure 210 presses on the sleeve 5 or the sleeve 7 that in turn presses on the insert 209 that in turn presses upon the upper portion 214 into locking frictional engagement with the receiver 207 at the surface 248.

The resulting assembly is then normally screwed into a bone, such as vertebra, by rotation of the shank 206 using a suitable driving tool (not shown) that operably drives and rotates the shank 206 by engagement thereof at the internal drive 231. Normally, the receiver 207, retainer 208 and insert 209 are assembled on the shank 206 before placing the shank 206 in the vertebra, but in certain circumstances, the shank 206 can be first implanted with the capture structure 214 extending proud to allow assembly and then the shank 206 can be further driven into the vertebra.

The assembly 1 may be assembled as follows: First, after the two bone screws 25 are implanted, the distance between the screws is measured. Thereafter, the spacer/liner combination 10 is cut to a desired length based upon the measurement made between the bone screws. As described above, the spacer 12 and the liner 13 that form the spacer/liner combination 10 are typically assembled at the factory, with the liner 13 being fixed to the spacer 12 along the spacer inner cylindrical surface 72. The spacer/liner combination 10 is cut at the spacer end 76 (that is also the liner end 96) that is opposite the graduated end of the spacer 12. A tool (not shown), similar to a pipe cutter is usually used to rotate and cut the spacer/liner combination 10 to the desired length. Also at this time, in view of the resulting spacer/liner 10 length, a sleeve 7 of a desired size is chosen. Because the sleeve 7 is made from a hard material, typically a metal or metal alloy, it is not practical to cut the tube portion 100 of the sleeve 7 to a desired length during the surgical procedure. Therefore, a variety of sleeves 7 are typically provided to end users having at least three different tube portion 100 lengths.

Figure 2:
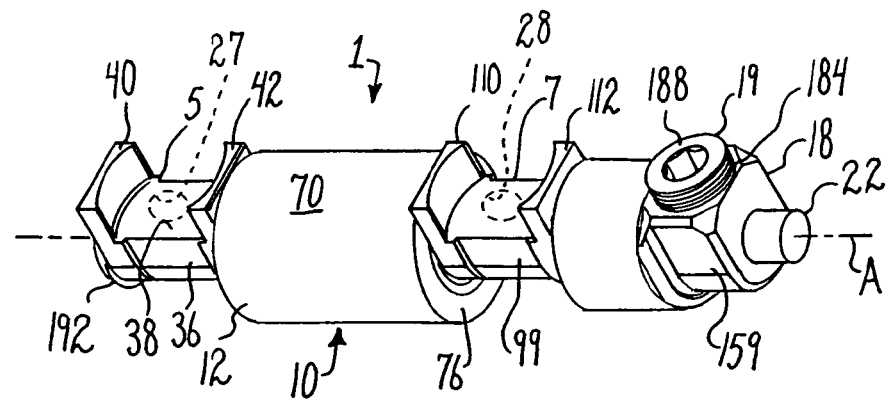
FIG. 2 is a perspective view of the connecting member of FIG. 1 shown without the polyaxial bone screws, the connecting member including an inner cord, first and second sleeves, a spacer/liner combination, an elastic bumper and a cord blocker with set screw, all shown prior to tensioning.
Figure 3:
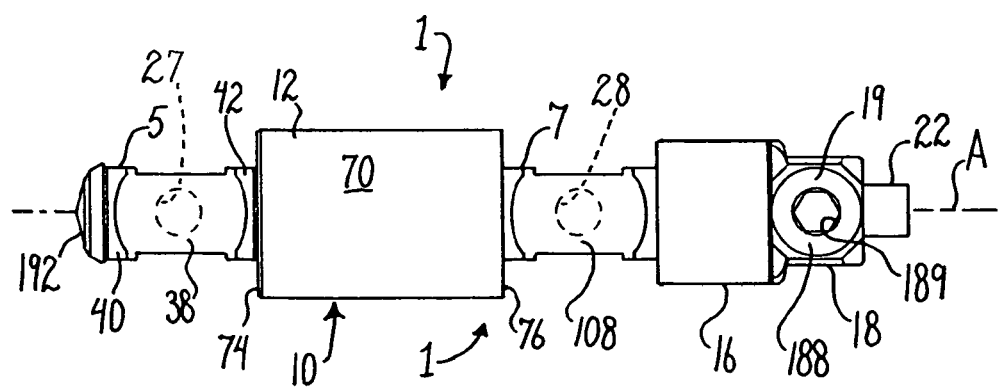
FIG. 3 is a top plan view of the connecting member of FIG. 2.
Figure 30:
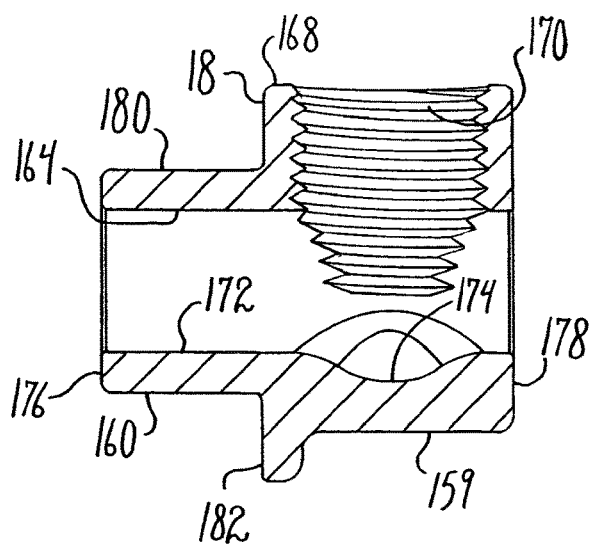
FIG. 30 is an enlarged cross-sectional view taken along the line 30-30 of FIG. 28.
Figure 30A:
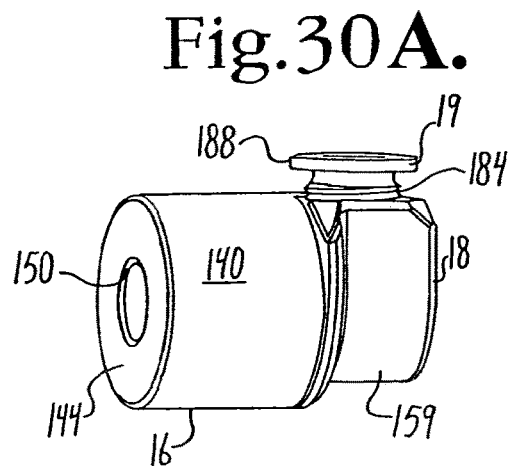
FIG. 30A is an enlarged perspective view of the blocker and set screw of FIG. 27 shown pre-assembled with the bumper of FIG. 23.

With particular reference to FIG. 4, the sleeve 5 is then slid onto the cord 22 at the cord end 194, with the end 194 being inserted into the through bore 34 at the sleeve end 52 and out the sleeve end 64. The sleeve 5 is then fed along the cord 22 until the sleeve end 52 is adjacent the enlarged cord end 192. It is noted that the cord 22 is typically much longer than shown in the drawing figures and then cut to length near the end 194 after being fully assembled with the remaining elements of the assembly 1, tensioned and fixed to the blocker 18. After the sleeve 5 is in place on the cord 22, the spacer/liner combination 10 (or optionally, the spacer without a liner) is loaded with the cord end 194 being inserted into the flared opening 80 at the end 74, the inner cylindrical surface 82, the inner cylindrical surface 84 and thereafter, the liner bore 92 and out the liner end 96 and spacer end 76. The spacer/liner combination 10 is slid along the cord 22 until the end 74 contacts the tubular extension 32 of the sleeve 5. A tensioning device (not shown) is typically needed to push and/or pull the spacer 12 against and over portions of the tubular extension 32 of the sleeve 5 until the inner cylindrical surface 82 of the spacer 12 fully engages the outer cylindrical surface 56 of the tubular extension 32 and the inner cylindrical surface 84 of the spacer 12 fully engages the outer cylindrical surface 60 of the tubular extension 32. At this time the sleeve end 64 is abutting against the spacer end surface 74 and in fixed relation thereto. However, both the spacer/liner combination 10 and the now attached sleeve 5 are in sliding relationship with the cord 22. It may be necessary to warm the spacer 12 prior to assembly with the tubular extension 32 to allow for stretching and expansion of the spacer 12 graduated inner surface (surfaces 80, 82, 84, and 86) to fit about the knob defined by the tubular extension annular wall 58 and cylindrical surface 60. The sleeve 7 is then loaded with the cord end 194 being inserted into the through bore 104 at the opening surface 131 near the end 128 and out the opening 125 at the end surface 124. The sleeve 7 is then slid along the cord 22 with the tubular extension 100 sliding into the liner bore 92. Thereafter, the blocker 18 with pre-attached bumper 16 and loosely mated set screw 19 (as shown in FIG. 30*a*) is loaded onto the cord 22 with the cord end 194 being inserted into the bumper bore 152 at the opening 150 located near the bumper end 144 and exiting the blocker bore opening near the end surface 178. The bumper 16 and attached blocker 18 are slid along the cord 22 until the bumper end 144 abuts against the sleeve 7 end surface 124. The resulting assembly, similar to what is shown in FIGS. 2 and 3 is now ready for placement in and between the implanted bone screws 25, with the set screw 19 engaged with the cord 22 enough to prevent the elements from slipping off of the cord 22. Unlike the illustrations of FIGS. 2 and 3, the cord 22 is not yet tensioned and thus the individual elements would most likely be more spread apart along the cord more than is illustrated in the drawings figures. Also, the cord 22 is much longer at this time so that the cord may be grasped and tensioned after the assembly is fixed to the bone screws 25.

The assembly 1 is implanted by inserting the sleeve 5 in to one of the bone screws 25 and the sleeve 7 into another of the bone screws 25. Closure tops 210 are then inserted into and advanced between the arms 234 and 235 of each of the receivers 207 so as to bias or push against the sleeve 5 and the sleeve 7 at respective planar surfaces 38 and 108. A driving tool (not shown) is inserted into each drive 297 to rotate and drive the respective closure top 210 into the receiver 207. Each shank dome 229 is engaged by the cooperating insert 209 and pushed downwardly when the closure top 210 pushes downwardly on the sleeve 5 or sleeve 7. The downward pressure on the shank 206 in turn urges the splines 224 downwardly which exerts both a downward and outward thrust on the retainer ring 208. Two polyaxial bone screws 25, including the dynamic connecting member assembly 1, are shown in FIGS. 1 and 37, illustrating various shank 206 to receiver 207 angular configurations.

A tensioning tool (not shown) known in the art is then used to pull upon and put tension on the cord 22 near the end 194. The cord 22 is preferably tensioned until the bumper compresses as shown in FIGS. 1 and 37 and then the set screw 19 is rotated and driven into the blocker 18 and up against the cord 22 using a driving tool (not shown) engaged with the inner drive 189. The blocker 18 advantageously includes opposed planar sides allowing for the placement of a counter-torque tool for holding the blocker 18 during tensioning and fixing of the cord 22 within the blocker. As explained above, the set screw 19 and blocker 18 combination include a limited travel feature such that the set screw 19 is locked into place at a location that firmly holds but does not damage the cord 22. The cord 22 is then trimmed to a desired length near the blocker end 178.

The assembly 1 is thus substantially dynamically loaded and oriented relative to the cooperating vertebra, providing relief (e.g., shock absorption) and protected movement with respect to flexion, extension, distraction and compressive forces placed on the assembly 1 and the two connected bone screws 25. The outer surfaces of the arms of the sleeves 5 and 7, in particular the surface 52 of the sleeve 5 and the surfaces 122 and 124 of the sleeve 7 are in fixed, flush relationship with the planar side surface 236 or 237 of an engaged bone screw receiver 207, thus better supporting compression between the spacer 12 or the bumper 16 during flexion and extension than that provided by current open implants that are not equipped with flush sleeves 5 or 7. It is also noted that a problem encountered with dynamic spinal implant systems is the need to provide adequate support with respect to bending sheer. Most spinal movements are not purely bending movements, e.g., flexion and extension. Most movements include both bending and tension, extension or compression. Such bending shear is not well resisted by a cord and spacer alone that performs well in tension, but not when the tension includes a vector force. The present invention advantageously provides a hard, non-elastic extension 100 of a rigid sliding sleeve body 99, the extension 100 further located within a non-elastic liner 13 of the spacer 12. Such features protect against vector forces while still allowing for advantageous tension of the cord 22 as well as improved compression provided by the outer bumper 16. The cord 22 and the sleeve 7 allow for some twisting or turning, providing some relief for torsional stresses. Furthermore, the compressed bumper 16 and the fixed contact between the sleeve 4 and the spacer 12 as well as the fixed contact between the bumper 16 and the blocker 18 places some limits on torsional movement as well as bending movement, to provide spinal support. The cord 22 (in tension) and bumper 16 (in compression) allow for compression and some extension of the assembly 1 located between the two bone screws 25, e.g., shock absorption. Another advantage of embodiments of the present invention is that because of the inelastic sleeve extension that slides within the typically elastic spacer located between two bone screws, the resulting assembly 1 is more stable than a cord and spacer alone, therefore strength of the assembly does not rely upon the amount of tension placed upon the cord. Therefore, in embodiments according to the invention, it is not necessary to place as much tension on the cord 22 as would be required for a more traditional cord and spacer arrangement, thus protecting the cord from damage of over stressing.

It is also noted that in other embodiments of a connecting member 1 according to the invention, the sleeve 5 may be extended at the end 52 to provide a hard, non-elastic elongate portion for attachment to an additional bone screw or screws, if needed, to provide a connecting member with both dynamic, elastic segments as well as a longer rigid inelastic segment.

If removal of the assembly 1 from any of the bone screw assemblies 25 is necessary, or if it is desired to release the assembly 1 at a particular location, disassembly is accomplished by using the driving tool (not shown) with a driving formation cooperating with the closure structure 210 internal drive 297 to rotate and remove the closure structure 210 from the receiver 207. Disassembly is then accomplished in reverse order to the procedure described previously herein for assembly.

Eventually, if the spine requires more rigid support, the connecting member assembly 1 according to the invention may be removed and replaced with another longitudinal connecting member, such as a solid rod or bar, having the same width or diameter as body portions of the sleeves 5 and 7, utilizing the same receivers 207 and the same or similar closure structures 210. Alternatively, if less support is eventually required, a less rigid, more flexible assembly, for example, an assembly 1 having a spacer 12 and bumper 16 made of a softer more compressible material than the spacer and bumper being replaced thereby, also utilizing the same bone screws 25.

With reference to FIG. 1*a*, an alternative longitudinal connecting member assembly according to the invention, generally 1*a*, for use with a polyaxial screw 25 and a monoaxial or fixed screw, 25*a* is shown. The screw 25*a* cooperates with a closure top 210*a* to fix a tensioned cord 22*a* between the screw 25*a* and a blocker 18 and cooperating set screw 19 of the invention previously described herein. The fixed screw 25*a* and cooperating closure 210*a* are the same or similar to the respective screw 12 and closure top 14 shown and described in U.S. patent application Ser. No. 12/661,042, filed Mar. 10, 2010, the disclosure of which is incorporated by reference herein. In the illustrated embodiment, the polyaxial screw 25 engages the sleeve 7 that allows the cord 22a to slide with respect thereto, the cord 22a being tensioned between the screw 25a and the blocker 18. The spacer 12 of the invention is compressible and directly engages the monoaxial screw 25a at one end thereof and the polyaxial screw 25 at the other end thereof. Furthermore, the spacer 12 engages the sleeve 7 that is flush with the screw 25. The blocker 18 directly engages the surface 237 of the polyaxial screw 25. Although the use of a bumper 16 is preferred according to the invention, as shown in FIG. 1a, a bumper is not necessary in some embodiments. It is also foreseen that in some embodiments of the invention, the sleeves 5 and 7 may be sized to fit entirely within a cooperating bone anchor, such that, for example, the bumper and spacer may directly engage the surfaces 237 of the bone screw 25, but not engage any surface of the sleeve that is fully contained within the bone screw receiver. In such embodiments, the sleeve may include a rim or nub (with cooperating structure on the receiver) for keeping such sleeve within the confines of the cooperating bone screw receiver. Such a nub or rim may also keep such a recessed sleeve in alignment with the receiver arms and in a position that an aperture in such a sleeve may receive a portion of a closure top for gripping a cord that is slidingly received within such a sleeve.

With reference to FIGS. 38-43, an alternative longitudinal connecting member assembly according to the invention, generally 301, for use with three bone screws 25 includes a first sleeve 305, a second sleeve 307, a third sleeve 308, a first spacer/liner combination 310 and a second spacer/liner combination 311. The first spacer/liner combination 310 includes an outer spacer 312 and an inner liner 313 and the second spacer/liner combination 311 includes an outer spacer 314 and an inner liner 315. The illustrated spacer/liner combination 311 is identical to the spacer/liner combination 310 with the exception of a length thereof along a central axis A". The assembly 301 further includes a bumper 316, a cord blocker 318 and mating set screw 319 and a cord 322. The assembly 301 is substantially similar to the assembly 1 with the exception of the addition of the third sleeve 308 and the second spacer/liner combination 311. Thus, the first sleeve 305, the second sleeve 307, the first spacer/liner combination 310, the bumper 316, the cord blocker 318, the set screw 319 and the cord 322 are the same or substantially similar to the respective first sleeve 5, second sleeve 7, spacer/liner combination 10, bumper 16, cord blocker 18, set screw 19 and cord 22 of the assembly 1 previously discussed above and thus shall not be discussed further herein. Although only one additional sleeve 309 (and attached bone screw 25) and cooperating spacer/liner 311 are illustrated in the drawings, it is noted that the assembly 301 of the invention may be lengthened further and adapted for use with additional bone screws by simply adding more sleeves 309 and cooperating spacer/liners 311 between the sleeve 305 and the sleeve 307.

With particular reference to FIGS. 40-43, the sleeve 309 includes a body portion 330 generally sized and shaped for being received within the polyaxial bone screw 25 and a first tubular extension 332 sized and shaped to engage and hold the spacer 312 in fixed engagement with the sleeve 309. The sleeve also includes a second opposed tubular extension 333 sized and shaped to be slidingly received by the spacer/liner combination 311. The illustrated body portion 330 and tubular extensions 332 and 333 are integral or otherwise fixed to one another. A through bore 334 extends through a lower portion of the body portion 330 and centrally through both the tubular extensions 332 and 333. The bore 334 is sized and shaped to slidingly receive the cord 322 and when assembled with a remainder of the assembly 301 extends along the axis A". The body portion 330 includes an outer side and lower surface 336 that is substantially U-shaped in cross-section, being sized and shaped to fit within a U-shaped opening of the bone screw 25. A substantial portion of the surface 336 terminates at an upper planar surface 338, with the U-shaped surface extending on either side of the planar surface 338 into upwardly extending arms or flanges 340 and 342. An optional opening 329 (shown in phantom) may be formed in the planar surface 338, the opening 329 sized and shaped for receiving a portion of an alternative closure top (not shown) that is sized and shaped to extend through the opening 329 and press against and/or penetrate the cord portion located within the sleeve 309, locking the cord with respect to the sleeve 309 as will be described in greater detail herein with respect to other embodiments of the invention (see, e.g., FIGS. 44 and 116). Inner surfaces 344 and 346 of the respective arms 340 and 342 form a discontinuous cylindrical wall sized and shaped to receive a closure top of the bone screw 25. The planar surface 338 is also a seating surface for the bone screw closure top. The arms 340 and 342 and the U-shaped body 336 are sized and shaped to fit within the receiver of the bone screw 25 and resist rotation and other forces placed on the sleeve 309. However, it is noted that in some embodiments, the sleeve 309 may be substantially cylindrical in outer form and thus receivable within a variety of fixed or polyaxial screw heads. In the illustrated embodiment, the arms 340 and 342 that are received within the polyaxial screw 25 terminate at respective upper planar surfaces 348 and 350. The arms 340 and 342 further include respective substantially planar outer or end surfaces 352 and 354, such surfaces being operatively flush with the side surfaces 236 or 237 of the bone screw 25. The outer surface 354 is adjacent to a tapered surface 355 that extends toward and terminates at a first cylindrical surface 356 of the tubular extension 332. The outer cylindrical surface 356 terminates at a radially extending annular wall 358 that is perpendicular thereto. The wall 358 terminates at a second substantially cylindrical surface 360 of greater outer diameter than the cylindrical surface 356. The surface 360 terminates at an annular inwardly tapering beveled surface 362. The bevel 362 is adjacent to a planar annular end surface 364 that is disposed perpendicular to the cylindrical surface 360. The surface 364 is adjacent to a flared or beveled surface 365 that defines an opening of the bore 334. The surfaces 356, 358 and 360 provide a push-on connective element for attachment to inner surfaces of the spacer 312. The sleeves 305, 307, 309, the liners 313 and 315 and the cord blocker 318 with set screw 319 may be made from a variety of inelastic materials, including, but not limited to metals, metal alloys, including cobalt chromium, and inelastic plastics including, but not limited to plastic polymers such as polyetheretherketone (PEEK), ultra-high-molecular weight-polyethylene (UHMWP), polyurethanes and composites, including composites containing carbon fiber and layers of different materials.

The tubular structure 333 includes a end surface 364 located adjacent to a flared or beveled surface 365 that defines an opposite opening the bore 334. At an opposite end of the tubular structure 333, the arm outer planar surface 352 is adjacent to a tapered surface 366 that extends toward and terminates at a cylindrical surface 367 of the tubular extension 333. The outer cylindrical surface 367 extends toward an annular planar end surface 368 that is perpendicular thereto. A beveled surface 370 spans between the cylindrical surface 367 and the end surface 368. The end surface 368 terminates at an inner flared surface 371, the surface 371 defining an opening of the bore 334. Upon assembly with the spacer 314/liner 315 combination, the cylindrical surface 367 is in slidable relationship with the inner surface of the liner 315. A desirable material for both the liner 315 and the tubular extension 333 is cobalt chromium. Furthermore, in some embodiments of the invention, in order to have low or no wear debris, the liner 315 inner surface and the outer surface 367 of the tubular extension 333 may be coated with an ultra thin, ultra hard, ultra slick and ultra smooth coating, such as may be obtained from ion bonding techniques and/or other gas or chemical treatments.

Figure 38:
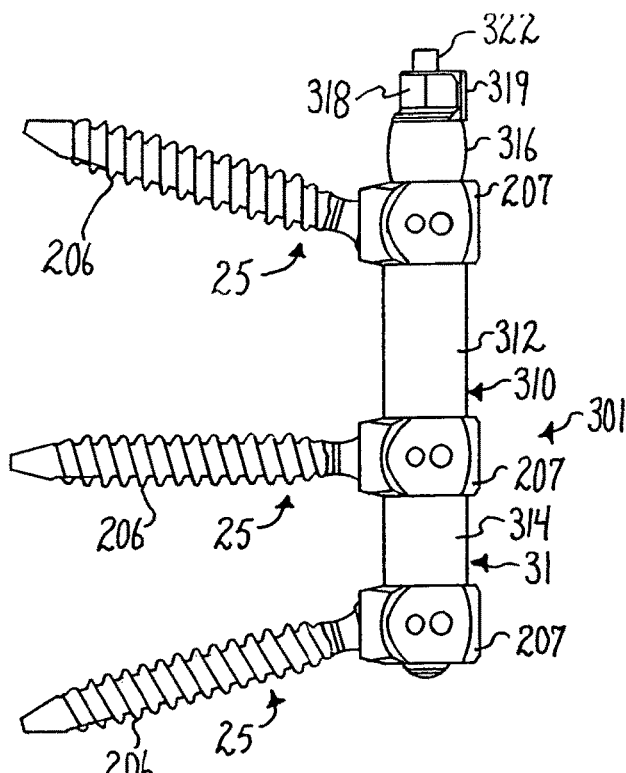
FIG. 38 is an enlarged perspective view of another embodiment of a dynamic fixation longitudinal connecting member according to the invention shown attached to three polyaxial bone screws.
Figure 39:
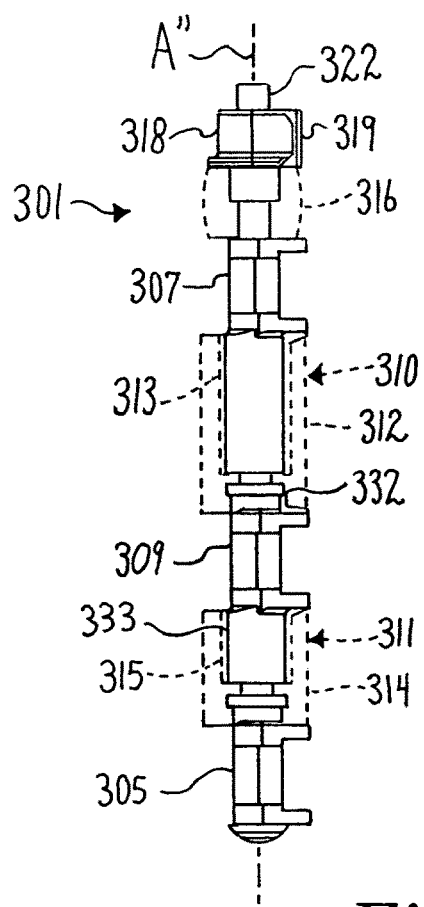
FIG. 39 is a side elevational view of the connecting member of FIG. 38 shown without the polyaxial bone screws, the connecting member including an inner cord, three sleeves, two spacer/liner combinations (shown in phantom), an elastic bumper (shown in phantom) and a cord blocker with set screw.
Figure 40:
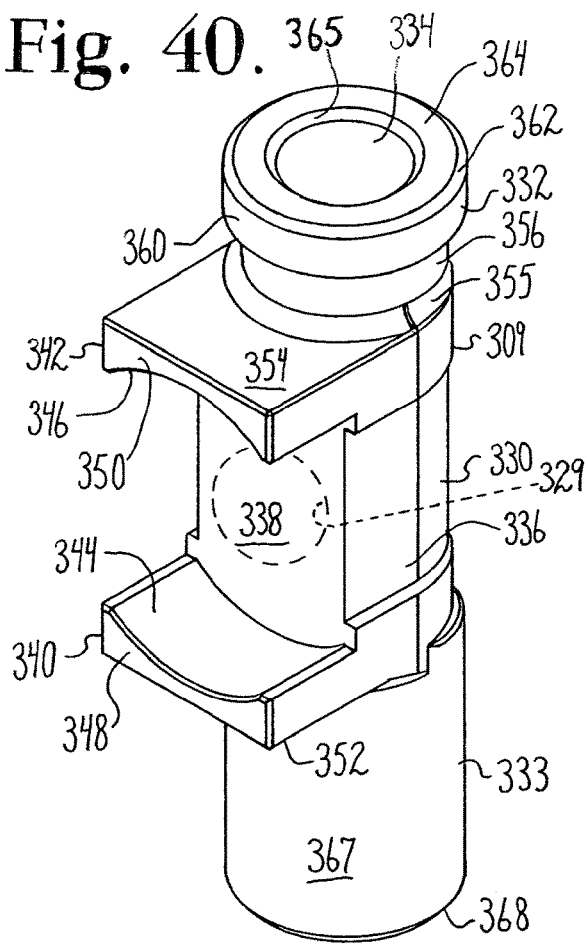
FIG. 40 is an enlarged perspective view of one of the sleeves of FIG. 39.
Figure 43:
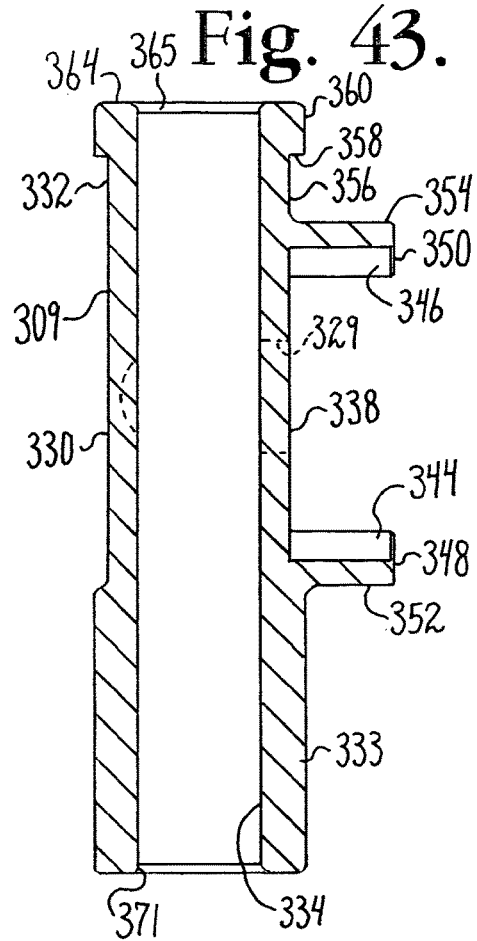
FIG. 43 is an enlarged cross-sectional view taken along the line 43-43 of FIG. 41.
Figure 41:
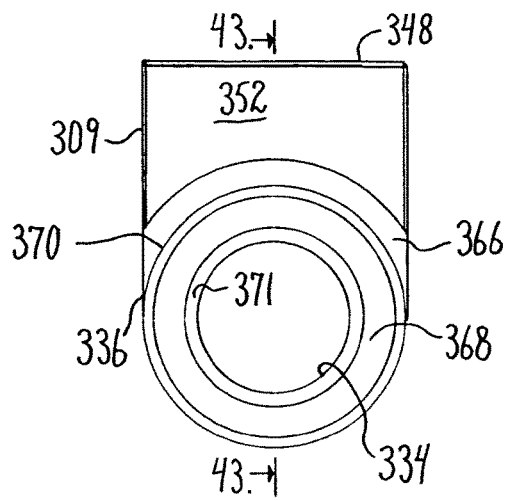
FIG. 41 is an enlarged rear elevational view of the sleeve of FIG. 40.
Figure 42:
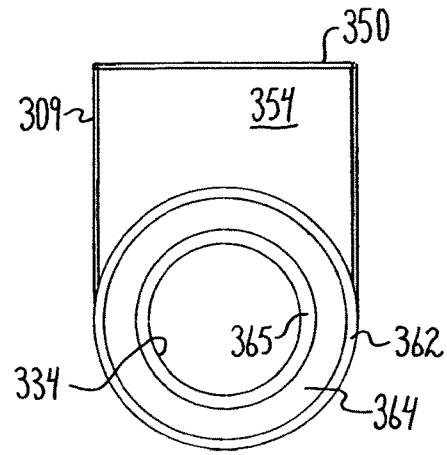
FIG. 42 is an enlarged front elevational view of the sleeve of FIG. 40.

As stated above, the spacer/liner combination 311 is identical to the spacer/liner combination 310 with the exception of length along the axis A". Thus, the spacer/liner combination 311 is identical or substantially similar to the spacer/liner combination 10 previously described herein. With reference to FIG. 39, during assembly, the spacer 312 is press-fitted over the tubular extension 332 of the sleeve 309 while the spacer 314 is press fitted over the tubular extension of the sleeve 305. Thus, the elements are loaded onto the cord 322 as follows: the sleeve 305, followed by the spacer/liner combination 311, followed by the sleeve 309, followed by the spacer/liner combination 312 followed by the sleeve 307, followed by the bumper 316 and attached blocker 318 with set screw 319. The assembly 301 is implanted with each of the sleeves 305, 307 and 309 being attached to a bone screw 25 as shown in FIG. 38. After the sleeves are attached to the bone screws 25, the cord 322 is tensioned. Thus, the fully assembled and dynamically loaded assembly 301 allows for translation of the receivers or heads 207 of all three of the bone screws 25 along the tensioned cord 322 while at the same time all three sleeves 305, 307 and 309 are fixedly coupled to a respective screw receiver 207. Furthermore, the tubular extension 333 of the sleeve 309 as well as the tubular extension of the sleeve 307 glide within spacer/liner combinations 310 and 311, protecting the assembly from bending shear forces while allowing for the desired movement of all three screws 25 with respect to the tensioned cord 322.

Figure 45:
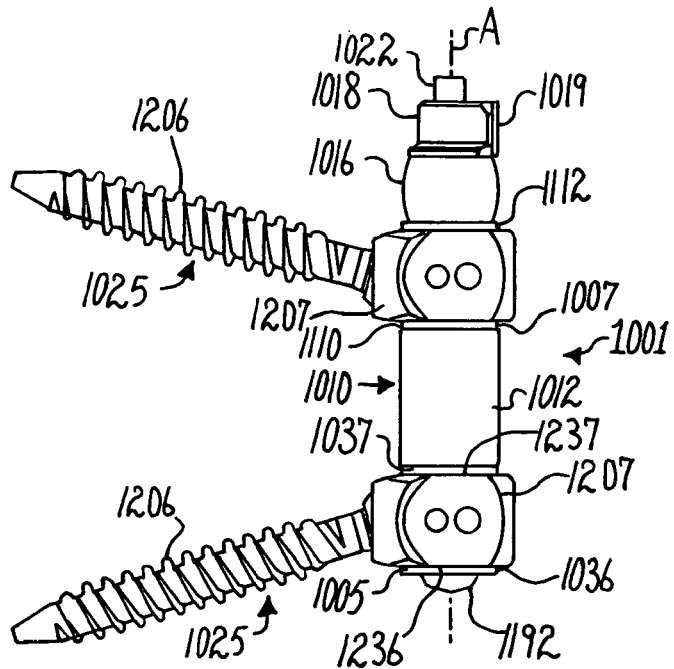
FIG. 45 is an enlarged front elevational view of another alternative longitudinal connecting member according to the invention shown attached to a pair of polyaxial bone screws.
Figure 72:
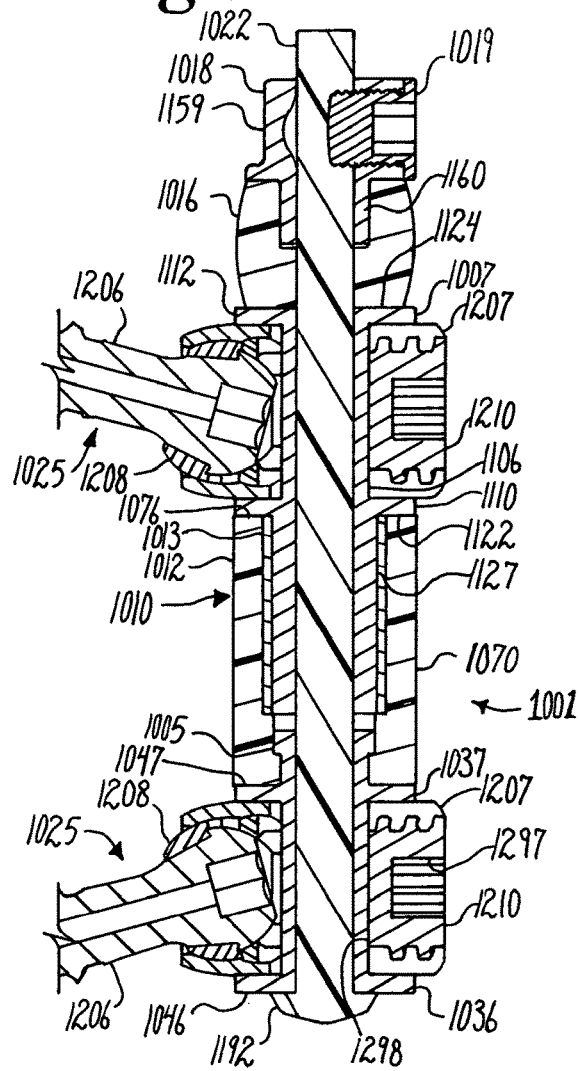
FIG. 72 is an enlarged and partial front elevational view of the assembly of FIG. 45 with portions broken away to show the detail thereof.
Figure 75:
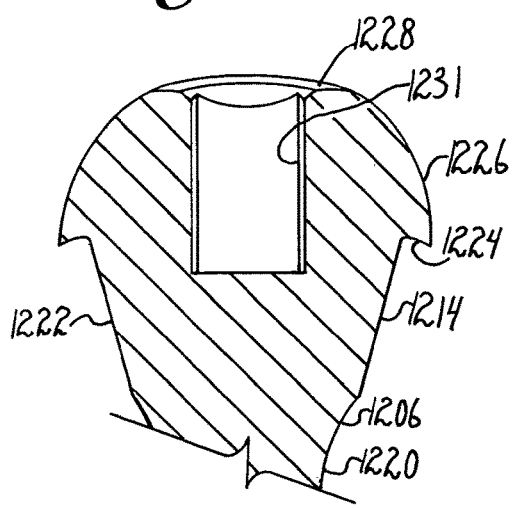
FIG. 75 is an enlarged and partial side elevational view of the shank of FIG. 73 with portions broken away to show the detail thereof.
Figure 74:
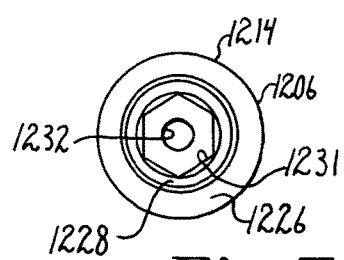
FIG. 74 is an enlarged top plan view of the shank of FIG. 73.
Figure 73:
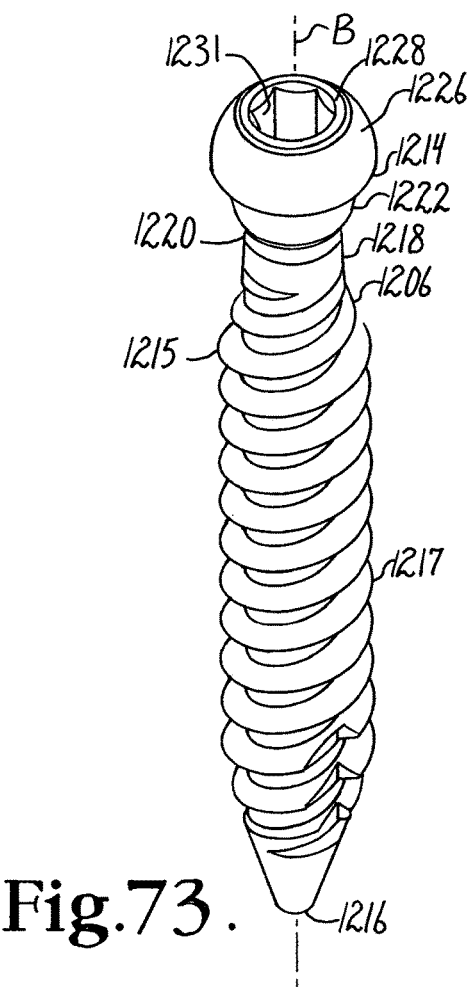
FIG. 73 is an enlarged perspective view of the bone screw shank of FIG. 69.

With particular reference to FIGS. 45-95, the reference numeral 1001 generally designates a non-fusion dynamic stabilization longitudinal connecting member assembly according to the present invention. The connecting member assembly 1001 is elongate, having a substantially central axis A. With particular reference to FIGS. 45-48, the illustrated connecting member assembly 1001 generally includes at least first and second hard, inelastic flanged sleeves 1005 and 1007 with a spacer/liner combination, generally 1010, located therebetween. In particular, the spacer/liner combination 1010 includes an outer spacer 1012 and an inner optional liner 1013. The assembly 1001 further includes an elastic bumper 1016, a cord blocker 1018 with cooperating set screw 1019 and an inner core that in the present embodiment is a cord 1022. The cord 1022 extends along the axis A and successively through and within the sleeve 1005, the spacer 1012, the sleeve 1007 (and spacer/liner 1010), the bumper 1016 and the cord blocker 1018 as shown, for example, in FIG. 72. In FIGS. 45 and 72, the assembly 1001 is shown attached to two polyaxial bone screws, generally 1025 at the sleeves 1005 and 1007. A portion of the sleeve 1007 extends into and through the spacer/liner 1010 and is in slidable relationship therewith. A portion of the cord blocker 1018 extends into a bore of the bumper 1016. As will be described and explained in greater detail below, the bumper 1016 is typically made from an elastomer while the outer spacer 1012 is also elastomeric, but typically made from a material with a different durometer, being tougher and less compressible than the material of the bumper 1016. Furthermore, the sleeves 1005 and 1007 and the spacer liner 1013 are made from a hard, non-elastic material, such as a metal or metal alloy, like cobalt chromium. The hard and stiff sliding sleeve 1007 includes an extension that slides into the liner 1013, providing a dynamic no- or low-wear, sliding relationship between the sleeve 1007 and the liner 1013 that is non-binding, and provides excellent shear resistance while at the same time, the thin liner 1013 cooperating with the elastomeric spacer 1012 as well as the tensioned cord 1022 provide controlled bending, with the tensioned cord 1022 and compressed bumper 1016, performing well under tension and compression. Flanged portions of the sleeves 1005 and 1007 are located on either side of the bone screws 1025, the flanges abutting against the spacer 1012 or the bumper 1016, the flanges extending radially outwardly to an extent to fully engage ends of the spacer 1012 or the bumper 1016, resulting in a stable, secure, substantially full contact between the individual elements of the assembly 1001. Furthermore, the flanges allow for assembly and dynamic setting of the assembly prior to implantation, if desired, with the cord 1022 being placed in tension and at least the bumper 1016 being placed in compression. In some embodiments of the invention, tensioning of the cord 1022 and compression of the bumper 1016 and optionally the spacer 1012 may be performed after the assembly 1001 is attached to the bone screws 1025.

With particular reference to FIGS. 49-53, the sleeve 1005 further includes a body portion 1030 generally sized and shaped for being received within the polyaxial bone screw 1025 and a tubular extension 1032 sized and shaped to engage and hold the spacer 1012 in fixed engagement with the sleeve 1005. The illustrated body portion 1030 and tubular extension 1032 are integral or otherwise fixed to one another. A through bore 1034 extends centrally through the body portion 1030 and centrally through the tubular extension 1032. The bore 1034 is sized and shaped to slidingly receive the cord 1022 and when assembled with a remainder of the assembly 1001 extends along the axis A. The body portion 1030 further includes a pair of spaced radially extending flanges 1036 and 1037 with a cylindrical body surface 1038 being located therebetween. The flanges 1036 and 1037 are spaced for closely receiving the bone screw 1025 therebetween as will be described in greater detail below. The flange 1036 also defines an end of the sleeve 1005 while the flange 1037 is located at a juncture of the body portion 1030 and the tubular extension 1032. The cylindrical surface 1038 is sized and shaped to be receivable within and frictionally fixed to a variety of monoaxial or polyaxial screw heads. In the illustrated embodiment, the flanges 1036 and 1037 further include respective substantially planar inner surfaces 1042 and 1043, respective outer planar surfaces 1046 and 1047 and respective outer cylindrical surfaces 1048 and 1049. The surfaces 1046 and 1047 may include ridges or other protruding structure for resisting rotation about the axis A. The planar surface 1046 also defines an end surface of the sleeve 1005. The surface 1046 is adjacent to a flared or beveled surface 1053 that defines an opening of the bore 1034. The outer surface 1047 is adjacent to a tapered surface 1055 that extends toward and terminates at a first cylindrical surface 1056 of the tubular extension 1032. The outer cylindrical surface 1056 terminates at a radially extending annular wall 1058 that is substantially perpendicular thereto and may be curved or flat. The wall 1058 terminates at a second substantially cylindrical surface 1060 of greater outer diameter than the cylindrical surface 1056. The surface 1060 terminates at an annular inwardly tapering beveled surface 1062. The bevel 1062 is adjacent to a planar annular end surface 1064 that is disposed perpendicular to the cylindrical surface 1060. The surface 1064 is adjacent to a flared or beveled surface 1065 that defines an opening of the bore 1034. The surfaces 1056, 1058 and 1060 provide a push-on connective element for attachment to inner surfaces of the spacer 1012 as will be described in greater detail below. The sleeve 1005, as well as the sleeve 1007, the optional liner 1013 and the cord blocker 1018 with set screw 1019 may be made from a variety of inelastic materials, including, but not limited to metals, metal alloys, including cobalt chromium, and inelastic plastics including, but not limited to plastic polymers such as polyetheretherketone (PEEK), ultra-high-molecular weight-polyethylene (UHMWP), polyurethanes and composites, including composites containing carbon fiber and layers of different materials.

With particular reference to FIGS. 45-48 and 54-57, the spacer 1012 is substantially cylindrical and tubular in form, having an outer cylindrical surface 1070 and an inner, graduated through bore, generally 1072. The spacer 1012 has opposed substantially planar annular end surfaces 1074 and 1076. The bore 1072 is defined in part by a first inner cylindrical surface 1078 that begins at the surface 1076 and extends substantially along a length of the spacer 1012. The surface 1078 closely receives the inner liner 1013 thereon. In fact, the spacer 1012/liner 1013 combination is typically assembled or manufactured with the optional liner 1013 being fixed to the surface 1078 such that a surgeon receives the spacer 1012/liner 1013 combination already assembled and ready for the surgeon to cut the spacer 1012/liner 1013 combination to a desired length near the end 1076 as will be described in greater detail below. Adjacent the end 1074, the spacer 1012 includes a flared or beveled opening surface 1080 extending to an inner cylindrical surface 1082 having an inner diameter smaller than the cylindrical surface 1078. A third inner cylindrical surface 1084 is located between the surface 1082 and the surface 1078, the surface 1084 having a diameter larger than the surface 1082 and smaller than the surface 1078. A curved transition surface 1086 spans between the cylindrical surfaces 1082 and 1084 and a curved transition surface 1088 spans between the cylindrical surfaces 1084 and 1078. Portions of the transition surfaces 1086 and 1088 are substantially perpendicular to the cylindrical surfaces 1078, 1082 and 1084. As will be described in greater detail below, when the spacer 1012/liner 1013 combination (or in some embodiments, a spacer 1012 only) is pushed onto the tubular extension 1032 of the sleeve 1005 during assembly, the end surface 1074 of the spacer 1012 engages the planar surface 1047 of the sleeve 1005, the flared surface 1080 of the spacer engages the tapered surface 1055 of the sleeve, the inner cylindrical surface 1082 engages the outer cylindrical surface 1056 of the sleeve, the surface 1086 of the spacer engages the surface 1058 of the sleeve, and the inner cylindrical surface 1084 of the spacer engages the outer cylindrical surface 1060 of the tubular extension 1032. As best shown in FIG. 72, the close fit between the spacer inner cylindrical surfaces 1082 and 1084 and the tubular extension 1032 of the sleeve 1005, provide a secure, fixed positioning of the spacer 1012 with respect to the sleeve 1005 along the axis A, prohibiting the spacer 1012 from being pulled away from the sleeve surface 1054 during spinal movement. However, some relative rotational movement between the spacer 1012 and the sleeve 1005 about the axis A is possible, allowing for some twist or turn, providing some relief for torsional stresses. The spacer 1012 is typically elastic and made from a plastic, for example, a thermoplastic elastomer made from a polyurethane or polyurethane blend, such as a polycarbonate urethane.

Figure 57:
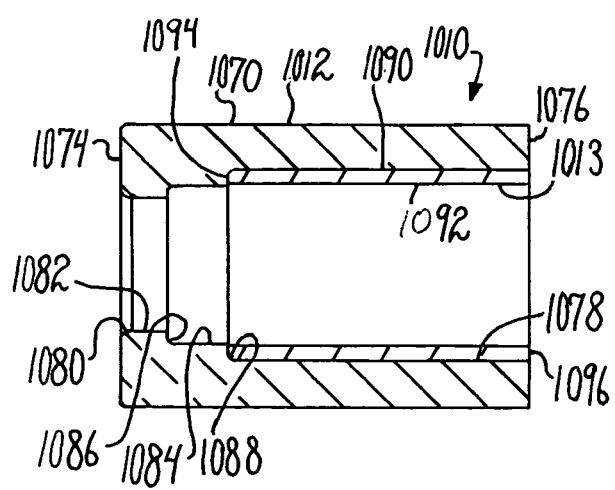
FIG. 57 is an enlarged cross-sectional view taken along the line 57-57 of FIG. 55.

Also with particular reference to FIGS. 54-57, the optional inelastic liner 1013 is substantially cylindrical and tubular in form, having an outer cylindrical surface 1090 and an inner cylindrical through bore 1092. The liner 1013 has opposed annular end surfaces 1094 and 1096. As best shown in FIG. 57, the end surface 1094 abuts against the annular surface 1088 of the spacer 1012 and the outer cylindrical surface 1090 is adhered or otherwise fixed to the inner cylindrical surface 1078 of the spacer 1012. The end surface 1096 is disposed flush to the end surface 1076 of the spacer 1012, these surfaces being the cut-to-length side of the spacer 1012/liner 1013 combination as will be described in greater detail below. Although shown as a separate part or element in some of the drawings, when used, the optional liner 1013 is typically provided pre-assembled within the spacer 1012. The liner 1013 may be made from a variety of non-elastic materials, including metals, metal alloys and some plastics, with cobalt chromium being a preferred material. The inner cylindrical surface 1092 is sized and shaped to slidingly receive a tubular extension of the inelastic sleeve 1007 as will be described in greater detail below.

Figure 95:
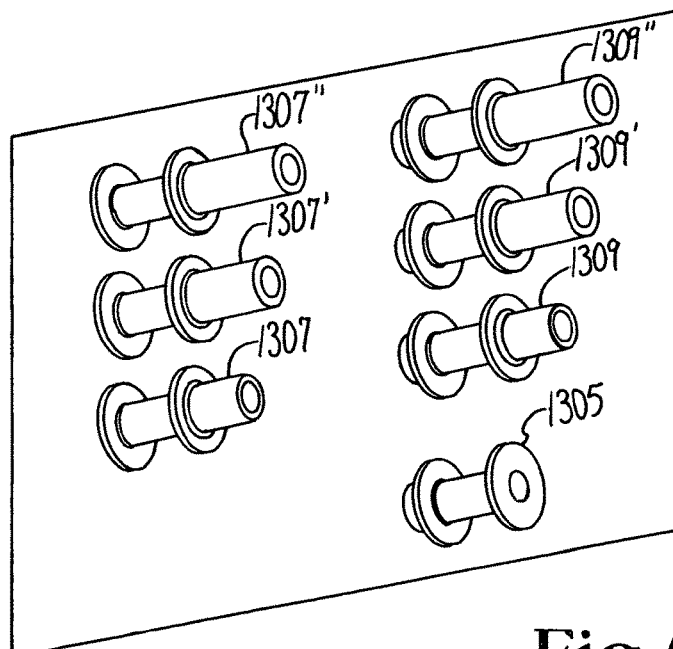
FIG. 95 is a reduced perspective view of a kit showing various lengths and configurations of sleeves according to the invention.

With particular reference to FIGS. 58-61, the sleeve 1007 includes a body portion 1099 generally sized and shaped for being received within the polyaxial bone screw 1025 and a tubular extension 1100 sized and shaped to be slidingly received in the spacer 1012/liner 1013 combination. The illustrated body portion 1099 and tubular extension 1100 are integral or otherwise fixed to one another. With particular reference to FIG. 95, more than one size of sleeve 1007 is typically provided to the surgeon, the sleeves 1007 differing only in the length of the tubular extension 1100, so as to appropriately match the size of the patient's spine. A through bore 1104 extends centrally through the body portion 1099 and the tubular extension 1100. The bore 1104 is sized and shaped to slidingly receive the cord 1022 and when assembled with a remainder of the assembly 1001 extends along the axis A. The body portion 1099 includes an outer cylindrical surface 1106 disposed between two radially extending flanges 1110 and 1112. The body portion 1099 and flanges 1110 and 1112 of the sleeve 1007 are substantially similar in form and function to the respective cylindrical body surface 1038 and flanges 1036 and 1037 of the sleeve 1005, with a polyaxial bone screw receiver being received between the flanges 1110 and 1112. The flanges 1110 and 1112 further include respective substantially planar inner walls 1114 and 1116, outer cylindrical surfaces 1118 and 1120 and outer walls or end surfaces 1122 and 1124. The surfaces 1122 and 1124 may include ridges or other protrusions. The outer surface 1124 is also an end surface of the sleeve 1007. The surface 1124 is adjacent to a flared or beveled surface 1125 that defines an opening of the bore 1104. The outer surface 1122 is adjacent to a tapered surface 1126 that extends toward and terminates at a cylindrical surface 1127 of the tubular extension 1100. The outer cylindrical surface 1127 extends toward an annular planar end surface 1128 that is perpendicular thereto. A beveled surface 1130 spans between the cylindrical surface 1127 and the end surface 1128. The end surface 1128 terminates at an inner flared surface 1131, the surface 1131 defining an opening of the bore 1104. Upon assembly with the spacer 1012/liner 1013 combination, the cylindrical surface 1127 is in slidable relationship with the inner surface of the liner 1013 defining the through-bore 1092. As stated above, a desirable material for both the liner 1013 and the tubular extension 1100 is cobalt chromium. Furthermore, in some embodiments of the invention, in order to have low or no wear debris, the liner 1013 inner surface and the outer surface 1127 of the tubular extension 1100 may be coated with an ultra thin, ultra hard, ultra slick and ultra smooth coating, such as may be obtained from ion bonding techniques and/or other gas or chemical treatments. It is further noted that inner surfaces of the sleeves 1005 and 1007 that receive the cord 1022 may also be likewise coated to provide a slick, low to no wear debris interface with the cord 1022.

With particular reference to FIGS. 62-68, the bumper 1016 is substantially cylindrical and tubular in form, having an outer cylindrical surface 1140 and an inner, graduated through bore, generally 1142. The bumper 1016 has opposed substantially planar annular end surfaces 1144 and 1146. The bore 1142 is defined in part by a first inner cylindrical surface 1148 that begins at the surface 1146. The surface 1148 closely receives a tubular extension of the cord blocker 1018 as will be described in greater detail below. Adjacent the end 1144, the bumper 1016 may include a flared or beveled opening surface extending to an inner cylindrical surface 1152 having an inner diameter smaller than a diameter of the inner cylindrical surface 1148. A curved transition surface 1156 spans between the cylindrical surfaces 1152 and 1148. A substantial portion of the surface 1156 is disposed perpendicular to the cylindrical surfaces 1152 and 1148. The bumper 1016 is elastic and may be made from a variety of compressible and stretchable materials, including, but not limited to natural or synthetic elastomers such as polyisoprene (natural rubber), and synthetic polymers, copolymers, and thermoplastic elastomers, for example, polyurethane elastomers such as polycarbonate-urethane elastomers. In order to have low or no wear debris, the bumper 1016 inner surface may also be coated with an ultra thin, ultra hard, ultra slick and ultra smooth coating, such as may be obtained from ion bonding techniques and/or other gas or chemical treatments.

Also with reference to FIGS. 62-68, the cord blocker 1018 and cooperating set screw 1019 are shown. The blocker 1018 includes a body portion 1159 and a tubular extension 1160 sized and shaped to be slidingly received in the bumper 1016 at the inner cylindrical surface 1148. The illustrated body portion 1159 and tubular extension 1160 are integral or otherwise fixed to one another. A through bore 1164 extends through a lower portion of the body portion 1159 and centrally through the tubular extension 1160. The bore 1164 is sized and shaped to receive the cord 1022 and when assembled with a remainder of the assembly 1001 extends along the axis A. The body portion 1159 includes an outer side and lower surface 1166 that is substantially U-shaped in cross-section, however, the surface 1166 may have a variety of outer geometries, including cylindrical or of other curved or polygonal cross-sections. The surface 1166 terminates at an upper planar surface 1168. Formed in the surface 1168 is a threaded bore 1170 sized and shaped to receive and threadably mate with the set screw 1019. The threaded bore 1170 communicates with the through bore 1164 and is substantially perpendicular thereto. Near the intersection of the bore 164 and the threaded bore 1170, a surface 1172 partially defining the bore 1164 includes a depression 1174, sized and shaped for receiving the cord 1022 therein when the set screw 1019 engages the cord 1022 as will be described in greater detail below. The blocker 1018 further includes opposed substantially planar end surfaces 1176 and 1178. The end surface 1176 is also the end surface of the tubular extension 1160 that has an outer cylindrical surface 1180. The end surface 1178 is also the end surface of the body 1159. The body further includes a substantially annular planar end surface 1182 adjacent the tubular extension 1160. In operation, the end surface 1146 of the bumper 1016 abuts against the end surface 1182.

The set screw 1019 includes a threaded body 1184 having a concave or domed bottom surface 1186 and a substantially cylindrical head 1188. Formed in the cylindrical head 1188 is an inner drive 1189 sized and shaped to receive a driving tool for rotating and advancing the set screw 1019 into the blocker 1018 at the threaded bore 1170. Specifically, the threaded body 1184 mates under rotation with the threaded bore 1170. The set screw 1019 and blocker 1018 are sized and shaped to have a limited travel or stop such that when the set screw 1019 is rotated into the bore 1170 and extends into the bore 1164, the set screw 1019 locks and cannot be advanced any further at a desired location wherein the cord 1022 is frictionally held firmly and snugly in place between the domed bottom 1186 and the concave or depressed surface 1174 without damaging or destroying the cord 1022.

It is noted that the blocker 1018 and set screw 1019 combination is typically provided with the bumper 1016 pre-attached thereto and handled as a unit assembly. Thus, prior to being received by the surgeon, the bumper 1016 is wedged and in some cases adhered or otherwise fixed onto the tubular extension 1160 at the factory, with the surface 1148 of the bumper frictionally engaging the surface 1180 of the blocker 1018 and the surface 1146 of the bumper 1016 abutting against and fixed to the surface 1182 of the blocker 1018.

With particular reference to FIGS. 47 and 48, the illustrated cord 1022 includes an elongate body 1190 with an enlarged end 1192 and an opposed cut-to-length end 1194. The enlarged end 1192 may be created by heating the cord 1022 to melt the cord and create the enlarged end 1192 that abuts against the surface 1046 of the sleeve 1005 and is too large to enter the bore 1034. Alternatively an outer pin or knob (not shown) may be fixed to the cord 1022. In other embodiments of the invention a blocker and set screw combination, similar to the blocker 1018 and set screw 1019 may be used to fix the cord 1022 outside of the sleeve 1005 and thus allow the cord 1022 to be in slidable relationship with the sleeve 1005. The cord 1022 may be made from a variety of materials, including polyester or other plastic fibers, strands or threads, such as polyethylene-terephthalate. A cord according to the invention typically does not illustrate elastic properties, such as any significant additional axial distraction and lengthening after the assembly 1001 is operatively assembled and the cord is tensioned. However, it is foreseen that in some embodiments, the cord 1022 may be made of an elastic or semi-elastic material, such as a plastic or rubber (natural or synthetic) having at least some elastic properties, allowing for some further distraction of the assembly 1001 during operation thereof. The core can also be a cable-like structure made of metal.

With particular reference to FIGS. 69-89 the reference number 1025 generally represents a polyaxial bone screw apparatus or assembly in accordance with the present invention operably utilized by implantation into a vertebra (not shown) and in conjunction with the connecting member assembly 1001 of the invention. The bone anchor assembly 1025 generally includes a shank 1206, a receiver 1207, a retainer structure or ring 1208, a lower pressure insert 1209 and a closure structure or top 1210.

The shank 1206 is elongate and has an upper body portion 1214 integral with a lower body portion 1215, ending in a tip 1216. The shank body 1215 has a helically wound bone implantable thread 1217 extending from near a tip 1216 to near a top area 1218 of the lower body 1215 and extending radially outward therefrom. During use, the body 1215 utilizing the thread 1217 is implanted into a vertebra. The shank 1206 has an elongated axis of rotation generally identified by the reference letter B.

Axially extending outward and upward from the shank body 1215 is a neck 1220 that in some embodiments is of reduced radius as compared to the adjacent top area 1218 of the body 1215. Further extending axially and outwardly from the neck 1220 is the shank upper portion 1214 operably providing a connective or capture structure free from the bone or vertebra for joining with the receiver 1207. The shank upper portion or capture structure 1214 has a frusto-conical surface 1222 located adjacent to the neck 1220 and extending outwardly to an undercut surface 1224 of a substantially spherical or domed shaped surface 1226 that is centrally radiused. The undercut surface 1224 forms an oblique angle with respect to the substantially conical surface 1222 as well as to the axis B. In some embodiments of the invention, the surface 1224 may be substantially perpendicular to the frusto-conical surface 1224 or in other embodiments, the surface 1224 may be substantially perpendicular to the axis B. However, it has been found that providing an undercut or oblique relationship between the domed surface 1226 and the frusto-conical surface 1222 results in better fixation of the retainer 1208 to the bone screw shank upper body portion 1214 as will be described in greater detail below. Also formed in the shank upper portion 1214 within an annular rim 1228 of the surface 1226 is a tool engagement aperture 1231 for engagement by a tool driving head (not shown) that is sized and shaped to fit into the aperture for both driving and rotating the shank 1206 into a vertebra. In the illustrated embodiment, the aperture 1231 is hex-shaped and runs parallel to the axis B. It is foreseen that various sizes, shapes and numbers of apertures, slots or the like may be utilized in accordance with the invention for engaging a driving tool of suitable and similar mating shape. The illustrated shank 1206 is cannulated, having a through bore 1232 extending an entire length of the shank 1206 along the axis B. The bore 1232 is defined by an inner cylindrical wall of the shank 1206 and has a circular opening at the shank tip 1206 and an upper opening communicating with the internal drive feature 1231. The bore 1232 provides a passage through the shank 1206 interior for a length of wire (not shown) inserted into the vertebra (not shown) prior to the insertion of the shank body 1215, the wire providing a guide for insertion of the shank body 1215 into the vertebra (not shown).

To provide a biologically active interface with the bone, the threaded shank body 1215 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bioceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

The receiver 1207 has a generally squared-off U-shaped appearance with a partially cylindrical inner profile and a substantially faceted outer profile; however, the outer profile could also include other geometrical configurations. Side surfaces of the receiver 1207 that are closely received by the flanges 1036 and 1037 of the sleeve 1005 or the flanges 1110 and 1112 of the sleeve 1007 are preferably planar. A receiver axis of rotation C is aligned with the axis of rotation B of the shank 1206 during assembly of the receiver 1207 with the shank 1206 and the retainer 1208. After the receiver 1207 is pivotally connected to the shank 1206, and such assembly is implanted in a vertebra (not shown), the axis C is typically disposed at an angle with respect to the axis B of the shank 1206.

With reference to FIGS. 69-88, the receiver 1207 has a base 1233 with a pair of upstanding arms 1234 and 1235 forming a U-shaped channel 1238 between the arms 1234 and 1235 having a lower seat 1239. Opposed planar side surfaces 1236 and 1237 also define the channel 1238 and extend upwardly from the base 1233 and to top surfaces 1240 of the arms. The insert 1209 that is disposed within the receiver 1207 is sized and shaped to closely receive the sleeve 1005 body surface 1038 or the sleeve 1007 body surface 1106. Each of the arms 1234 and 1235 has an interior surface 1241 that includes a partial helically wound guide and advancement structure 1242. In the illustrated embodiment, the guide and advancement structure 1242 is a partial helically wound flangeform that mates under rotation with a similar structure on the closure top 1210, as described below. However, it is foreseen that the guide and advancement structure 1242 could alternatively be a buttress thread, a reverse angle thread or other thread like or non-thread like helically wound advancement structures for operably guiding under rotation and advancing the closure top between the arms 1234 and 1235. Also, non-helically wound closure tops or caps are foreseen. Tool engaging apertures 1244 are formed on the outsides of the arms 1234 and 1235 for holding the receiver 1207 during certain assembly steps and/or implantation of the assembly and also for access to a thin deformable wall 1245 during assembly with the pressure insert 1209.

A chamber or cavity 1247 is located within the receiver base 1233 that opens upwardly into the U-shaped channel 1238. The cavity 1247 includes a partial spherical shaped surface 1248, at least a portion of which forms a partial internal hemispherical seat for the retainer 1208, as is described further below. A lower neck 1250 defining a lower bore further communicates between the cavity 1247 and the bottom exterior of the base 1233 and is coaxial with the rotational axis C of the receiver 1207. The neck 1250 at least partially defines a restriction having a radius which is smaller than the radius of the retainer 1208 when the retainer is fully engaged with the frusto-conical surface 1222 of the shank 1206, so as to form a restrictive constriction at the location of the neck 1250 relative to the retainer 1208 to prevent the retainer 1208 from passing between the cavity 1247 and the lower exterior of the receiver 1207.

In an upper portion of the cavity 1247, a substantially cylindrical surface 1252 includes a run-out surface 1253 located directly beneath the guide and advancement structure 1242. With particular reference to FIGS. 82-83 and 87-88, formed in the surface 1253 under the structure 1242 of both of the arms 1234 and 1235 is a recess 1254 partially defined by a stop or abutment wall 1255. As will be described in greater detail below, the cooperating compression insert 1209 includes a protruding structure 1294 on each arm thereof that abuts against the respective wall 1255 of each of the receiver arms, providing a centering stop when the insert 1209 is rotated into place as will be described below.

With particular reference to FIGS. 76-81, the retainer 1208 is an open and substantially ring-shaped and has an operational central axis which is the same as the elongate axis B associated with the shank 1206, but when the retainer 1208 is separated from the shank 1206, the axis of rotation is identified as axis D. The retainer 1208 has a central bore 1256 that passes entirely through the retainer 1208 from a top surface 1258 to a bottom surface 1259 thereof. The bore 1256 is substantially formed by a frusto-conical surface 1257, sized and shaped to fit snugly over the shank capture structure frusto-conical surface 1222 in such a manner as to allow sliding axial movement therebetween during assembly and substantially full contact between the surface 1257 and the surface 1222 during operation, as described below.

As stated above, the retainer 1208 is open, having a through-gap running from the top surface 1258 through the bottom surface 1259, the gap formed by facing surfaces 1260 and 1261. The illustrated surfaces 1260 and 1261 are substantially parallel, both running substantially perpendicular to the top and bottom surfaces 1258 and 1259. It is foreseen that in other embodiments of the invention, the surfaces 1260 and 1261 may form and oblique angle with the top and bottom surfaces 1258 and 1259. With particular reference to FIGS. 70 and 80, the gap between the surfaces 1260 and 1261 is sized such that the surfaces 1260 and 1261 may be moved toward one another, squeezing the retainer 1208 about the shank neck 1220 during assembly such that the retainer 1208 and shank upper portion 1214 may be inserted into and through the neck 1250 of the receiver 1207 and into the receiver cavity 1247 wherein the retainer 1208 may be released and allowed to expand to a natural state thereof, capturing both the retainer 1208 and the shank upper portion 1214 within the receiver cavity 1247.

The retainer top surface 1258 includes a cut or notch, generally 1262 that appears substantially v-shaped in cross-section. Specifically, the cut 1262 is defined by a substantially curved or spherical surface 1263 and a contiguous partially conical or sloping surface 1264. The notch 1262 is located near the frusto-conical surface 1257, with the sloping surface 1262 extending to or near the surface 1257. In the illustrated embodiment, the surface 1262 extends to a rounded or beveled annular surface 1266 that opens to the surface 1257 that defines the inner bore 1256. The curved surface 1263 has a radius that is the same or substantially similar to the radius of the domed surface 1226 of the shank upper body portion 1214. The conical surface 1264 is sized and shaped to be closely received by the undercut surface 1224 of the shank upper body portion 1214. Thus, when the surface 1257 engages the shank surface 1222 and is slid axially toward the domed surface 1226 during assembly, the shank undercut 1224 engages the surface 1264 and the spherical surface 1263 of the notch 1262 engages a portion of the domed surface 1226, advantageously providing a stop and a secure fit between the retainer 1208 and the shank upper body portion 1214 within the receiver 1207.

The retainer 1208 has a radially outer partial hemispherical shaped surface 1265 sized and shaped to mate with the partial spherical shaped surface 1248 of the receiver 1207 and having a radius approximately equal to a radius associated with the surface 1248. The retainer 1208 radius (when in an operational non-squeezed orientation) is larger than the radius associated with the annular curved surface 1229 of the shank upper portion 1214 and also substantially larger than the radius of the receiver neck 1250.

With particular reference to FIGS. 84-88, the lower compression or pressure insert 1209 includes a substantially cylindrical body 1270 integral with a pair of upstanding arms 1272. The body 1270 and arms 1272 form a generally U-shaped, open, through-channel 1274 having a lower seat 1276 sized and shaped to closely, snugly engage the sleeve 1005 or the sleeve 1007. The arms 1272 disposed on either side of the channel 1274 extend outwardly from the body 1270. The arms 1272 are sized and configured for placement near the run-out 1253 below the guide and advancement structure 1242 at the receiver inner arms 1234 and 1235. Each of the arms 1272 includes a top surface 1278 ultimately located directly beneath the guide and advancement structure 1242, but are not directly engaged by the closure top 1210. However, in some embodiments of the bone screw for use with other longitudinal connecting members, the closure top may directly engage the top surfaces 278 for locking the polyaxial mechanism of the assembly 1025. Therefore, the assembly 1 may be used with a wide variety of longitudinal connecting members, including the sleeves 1005 and 1007 or inelastic or deformable rods or other connecting members that engage the closure top 1210 and are locked into position by such closure top 1210 as well as rods of smaller diameter or, for example cords that are captured by the closure top 1210, but are otherwise movable within the receiver 1207 and are thus in slidable or spaced relation with the closure top 1210. Each arm 1272 further includes a partially cylindrical outer surface 1280 sized and shaped to fit within the receiver 1207 at the guide and advancement structure 1242 run-out relief 1253. The cylindrical surfaces 1280 are disposed substantially perpendicular to the respective adjacent top surfaces 1278. In some embodiments of the invention recesses are formed near and/or at the top surfaces 1278 and the surfaces that form the channel 1274 to provide relief for material flow of the longitudinal connecting member, when, for example, the connector is made from a deformable plastic. For example, a recessed surface or groove may be directed downwardly and inwardly toward the channel 1274. Each of the outer surfaces 1280 further includes a recess 1282 sized and shaped to receive holding tabs or crimped material from the receiver 1207. For example, as shown in FIG. 71, the thin walls 1245 of the receiver 1207 are pressed into the recesses 1282 to prevent counter-clockwise rotation of the insert 1209 about the axis C with respect to the receiver 1207. In other embodiments of the invention, the receiver 1207 may be equipped with spring tabs that snap into the recesses 1282 to hold the insert 1209 in place with respect to counter-clockwise rotation. The recesses 1282 are preferably oval or elongate such that some desirable upward and downward movement of the insert 1209 along the axis C of the receiver 1207 is not prohibited. As previously described herein the compression insert 1209 arms each include the protruding structure 1294 located on opposite sides of the arms such that when the insert 1209 is dropped down into the receiver 1207 as shown by the arrow M in FIG. 87 and then rotated into place in a clockwise direction as shown by the arrow N in FIG. 88, the structure 1294 abuts the wall 1255 of the recessed area 2154 when the insert is in a desired centered location with the apertures 1282 in alignment with the apertures 1244.

The compression insert 1209 further includes an inner cylindrical surface 1284 that forms a through bore sized and shaped to receive a driving tool (not shown) therethrough that engages the shank drive feature 1231 when the shank body 1215 is driven into bone. The inner surface 1284 runs between the seating surface 1276 and an inner curved, annular, radiused or semi-spherical surface 1286. The surface 1286 is sized and shaped to slidingly and pivotally mate with and ultimately fix against the annular domed surface 1226 of the shank upper portion 1214. Thus, a radius of the surface 1286 is the same or substantially similar to the radius of the surface 1226. The surface 1286 may include a roughening or surface finish to aid in frictional contact between the surface 1286 and the surface 1226, once a desired angle of articulation of the shank 1206 with respect to the receiver 1207 is reached. Adjacent to the inner surface 1286 is a bottom rim or edge 1288. Adjacent to the outer cylindrical surface 1280 of the arms 1272 is a substantially frusto-conical surface 1290 that extends inwardly toward the lower rim 1288. The surface 1290 includes portions of the arms 1272 as well as partially defining the pressure insert body 1270.

Figure 87:
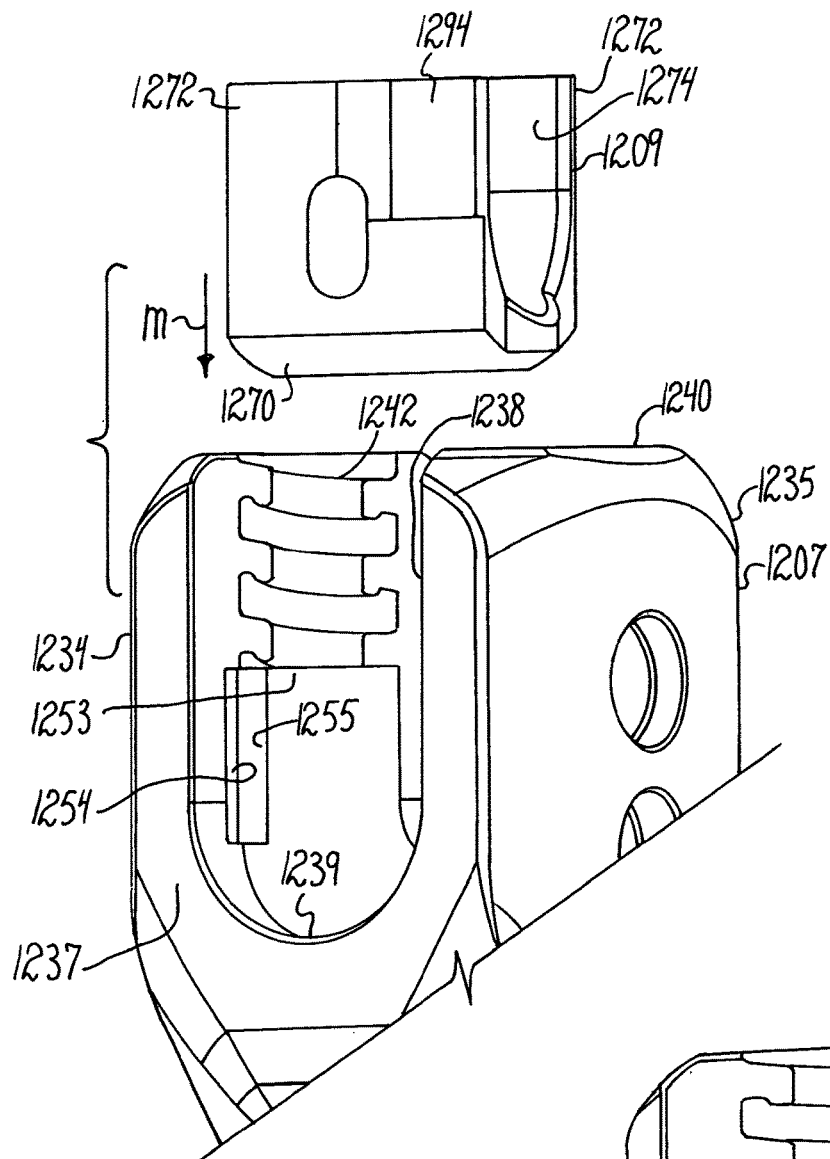
FIG. 87 is an enlarged and partial perspective view of the receiver and compression insert of FIG. 69 shown in an early stage of assembly.

The pressure inset body 1270 located between the arms 1272 has an outer diameter slightly smaller than a diameter between crests of the guide and advancement structure 1242 of the receiver 1207 allowing for top loading of the compression insert 1209 into the receiver 1207 through the U-shaped channel 1238, with the arms 1272 being located between the arms 1234 and 1235 during insertion of the insert 1209 into the receiver 1207 (see FIG. 87). As explained above, once located between the guide and advancement structure 1242 and the shank upper portion 1214, the insert 1209 is rotated into place about the axis C until the arms 1272 are directly below the guide and advancement structure 1242 at or near the run-out 1253 and the structure 1294 abuts against the wall 1255 of the recess 1254. After the insert 1209 is rotated into such position, a tool (not shown) may be inserted into the receiver apertures 1244 to press the thin receiver walls 1245 into the insert recesses 1282. The lower compression insert 1209 is sized such that the insert 1209 is ultimately received within the cylindrical surface 1252 of the receiver 1207 below the guide and advancement structure 1242. The receiver 1207 fully receives the lower compression insert 1209 and blocks the structure 1209 from spreading or splaying in any direction. It is noted that assembly of the shank 1206 with the retainer 1208 within the receiver 1207, followed by insertion of the lower compression insert 1209 into the receiver 1207 are assembly steps typically performed at the factory, advantageously providing a surgeon with a polyaxial bone screw with the lower insert 1209 already held in alignment with the receiver 1207 and thus ready for insertion into a vertebra.

The compression or pressure insert 1209 ultimately seats on the surface 1226 of the shank upper portion 1214 and is disposed substantially in the upper cylindrical portion 1252 of the cavity 1247, with the receiver deformable walls 1245 engaging the insert 1209 at the recesses 1282, thereby cooperating with the walls 1255 of the recesses 1254 to hold the insert 1207 in desired alignment.

Figure 69:
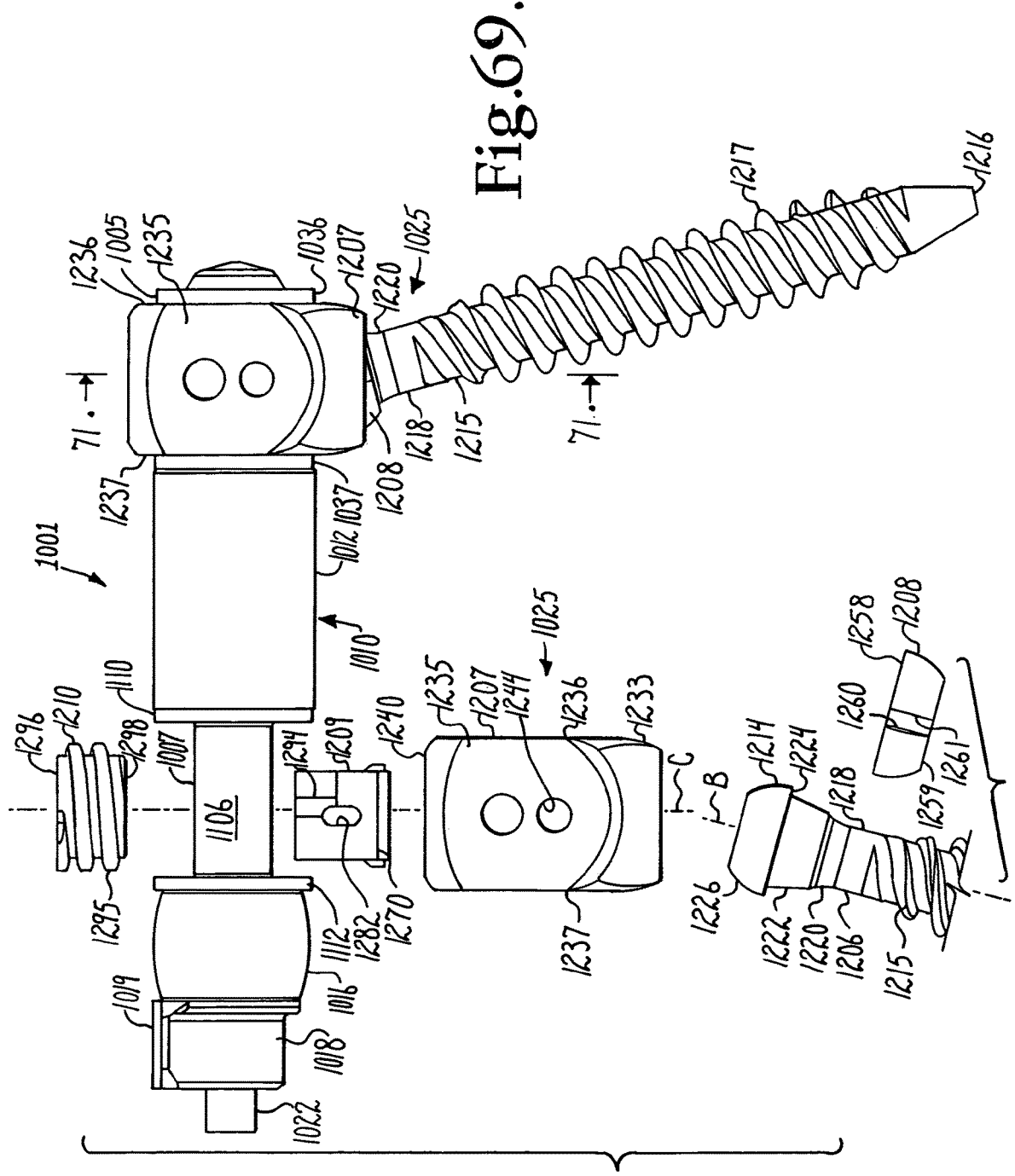
FIG. 69 is an enlarged and partial perspective view of the connector and bone screws of FIG. 45 further showing a bone screw in exploded view, the bone screw including a bone screw shank, retainer, receiver, compression insert and closure top.

With particular reference to FIGS. 69-71, the closure structure or closure top 1210 can be any of a variety of different types of closure structures for use in conjunction with the present invention with suitable mating structure on the upstanding arms 1234 and 1235. In the embodiment shown, the closure top 1210 is rotatably received between the spaced arms 1234 and 1235 of the receiver 1207. The illustrated closure structure 1210 is substantially cylindrical and includes an outer helically wound guide and advancement structure 1295 in the form of a flange form that operably joins with the guide and advancement structure 1242 of the receiver 1207. The flange form utilized in accordance with the present invention may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 1210 downward between the arms 1234 and 1235 and having such a nature as to resist splaying of the arms 1234 and 1235 when the closure structure 1210 is advanced into the channel 1238. The illustrated closure structure 1210 also includes a top surface 1296 with an internal drive 1297 in the form of an aperture that is illustrated as a star-shaped internal drive, but may be, for example, a hex-shaped drive or other internal drives, including, but not limited to slotted, tri-wing, spanner, two or more apertures of various shapes, and the like. A driving tool (not shown) sized and shaped for engagement with the internal drive 1297 is used for both rotatable engagement and, if needed, disengagement of the closure 210 from the receiver arms 1234 and 1235. It is also foreseen that the closure structure 1210 may alternatively include a break-off head designed to allow such a head to break from a base of the closure at a preselected torque, for example, 70 to 140 inch pounds. Such a closure structure would also include a base having an internal drive to be used for closure removal. A bottom surface 1298 of the closure top 1210 is planar and is sized and shaped to engage the sleeve 1005 or the sleeve 1007 at respective surfaces 1038 and 1106.

The closure top 1210 may further include a cannulation through bore extending along a central axis thereof and through a surface of the drive 1297 and the bottom surface 1298. Such a through bore provides a passage through the closure 1210 interior for a length of wire (not shown) inserted therein to provide a guide for insertion of the closure top into the receiver arms 1234 and 1235.

When the polyaxial bone screw assembly 1201 is placed in use in accordance with the invention the retainer 1208 is normally inserted about the shank at or near the neck 1220 by spreading the retainer 1208, moving the surfaces 1260 and 1261 away from one another and enlarging the gap therebetween so that the retainer surfaces 1260 and 1261 clear the area of the neck 1220 until the retainer 1208 substantially surrounds the shank 1206 at or near the neck 1220. Thereafter, the retainer is squeezed or pressed, bringing the surfaces 1260 and 1261 into contact or close proximity as shown in FIG. 80. Thereafter, the shank 1206 and compressed retainer 1208 are inserted into the receiver 1208 at the receiver neck 1250 and up into the receiver cavity 1247 where the retainer 1208 is released and allowed to return to an original shape with a gap between the surfaces 1260 and 1261. The shank upper portion 1214 is then pulled axially downwardly toward the receiver neck 1250 with the surface 1257 of the retainer 1208 sliding along the frusto-conical surface 1222 of the shank upper portion 1214 until the retainer notch 1262 engages the shank upper portion undercut 1224 with the retainer spherical surface 1263 surrounding a portion of the domed surface 1226 of the shank upper portion 1214 as shown, for example, in FIG. 81. At this point there is no substantial outward or downward pressure on the retainer 1208 and so the retainer 1208 is easily rotatable along with the now attached shank 1206 within the chamber 1247 and such rotation is of a ball and socket type wherein the angle of rotation is only restricted by engagement of the shank neck 1220 with the neck 1250 of the receiver 1207.

Figure 88:
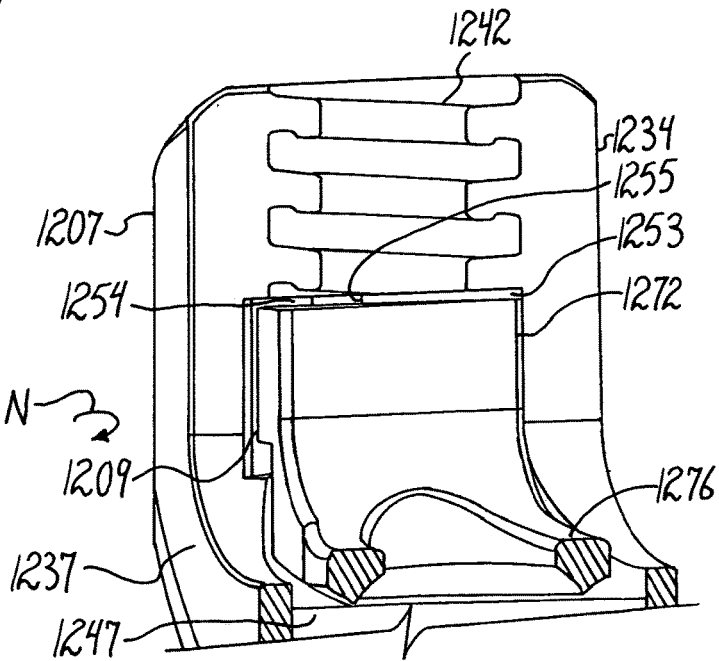
FIG. 88 is an enlarged and partial perspective view of the receiver and compression insert of FIG. 87 shown in a later stage of assembly and with portions broken away to show the detail thereof.
Figure 89:
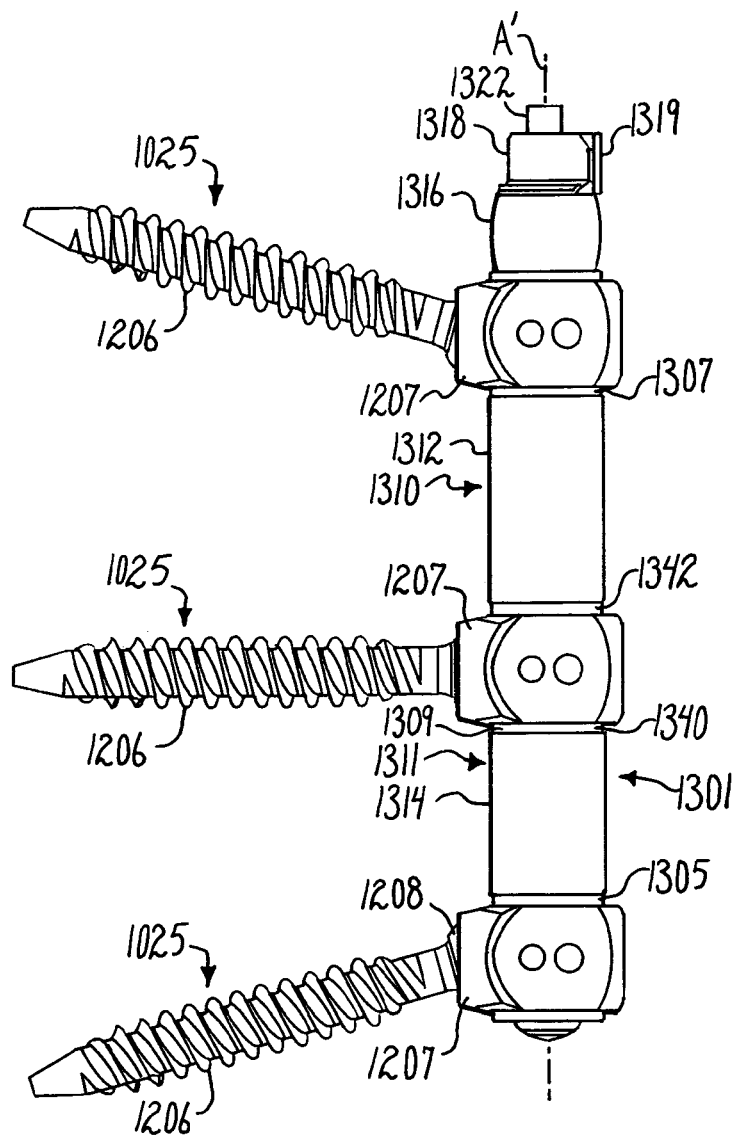
FIG. 89 is an enlarged front elevational view of another embodiment of a longitudinal connecting member according to the invention shown attached to three polyaxial bone screws.

Then, the insert 1209 is inserted into the channel 1238 with the arms 1272 aligned in the channel 1238 between the guide and advancement structures 1242. The insert 1209 is then moved downwardly in the channel 1238 and toward the cavity 1247. With reference to FIGS. 87-88, once the arms 1272 are located generally below the guide and advancement structure 1242 and adjacent the run-out relief 1253, the insert 1209 is rotated 90 degrees in a clockwise direction about the axis C of the receiver 1207. The arms 1272 fit within the cylindrical walls 1252 above the cavity 1247. Once the structures 1294 abut against the walls 1255, the arms 1272 are desirably located directly below the guide and advancement structures 1242, rotation is ceased and a tool (not shown) is used to press the thin walls 1245 of the receiver 1207 into the recesses 1282 of the insert 1209. The insert 1209 is now locked into place inside the receiver 1207 with the guide and advancement structures 1242 prohibiting upward movement of the insert out of the channel 238.

As illustrated in FIG. 71, the insert 1209 seats on the shank upper portion 1214 with the surface 1286 in sliding engagement with the surface 1226. The run-out or relief 1253 is sized and shaped to allow for some upward and downward movement of the insert 1209 toward and away from the shank upper portion 1214 such that the shank 1206 is freely pivotable with respect to the receiver 1207 until the closure structure 1210 presses on the sleeve 1005 or the sleeve 1007 that in turn presses on the insert 1209 that in turn presses upon the upper portion 1214 into locking frictional engagement with the receiver 1207 at the surface 1248.

The resulting assembly is then normally screwed into a bone, such as vertebra, by rotation of the shank 1206 using a suitable driving tool (not shown) that operably drives and rotates the shank 1206 by engagement thereof at the internal drive 1231.

The assembly 1001 may be assembled as follows: First, after the two bone screws 1025 are implanted, the distance between the screws is measured. Thereafter, the spacer/liner combination 1010 (or in some embodiments a spacer without the liner) is cut to a desired length based upon the measurement made between the bone screws. As described above, the spacer 1012 and the optional liner 1013 that form the spacer/liner combination 1010 are typically assembled at the factory, with the liner 1013 being fixed to the spacer 1012 along the spacer inner cylindrical surface 1072. The spacer/liner combination 1010 is cut at the spacer end 1076 (that is also the liner end 1096) that is opposite the graduated end of the spacer 1012. A tool (not shown), similar to a pipe cutter is usually used to rotate and cut the spacer/liner combination 1010 to the desired length. Also at this time, in view of the resulting spacer/liner 1010 length, a sleeve 1007 of a desired size is chosen. Because the sleeve 1007 is made from a hard material, typically a metal or metal alloy, it is not practical to cut the tube portion 1100 of the sleeve 1007 to a desired length during the surgical procedure. Therefore, a variety of sleeves 1007 are typically provided to end users having at least three different tube portion 1100 lengths. See, for example, FIG. 95 that shows three different sizes of a sleeve 1307, 1307' and 1307" of the assembly 1301 which are sleeves identical in form and function to the sleeve 1007 and differing only in their length.

Figure 46:
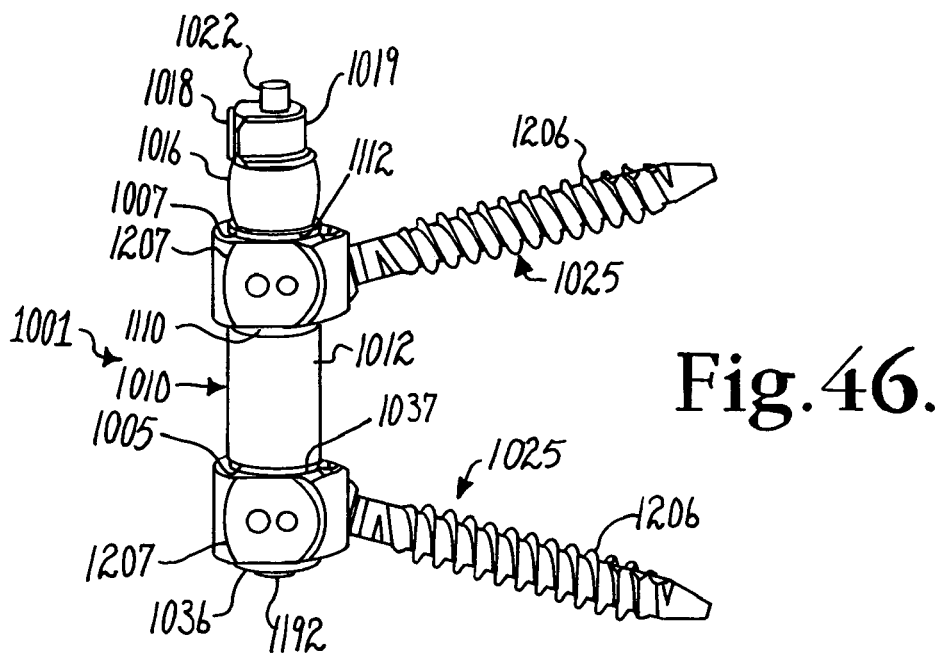
FIG. 46 is an enlarged perspective view of the connecting member of FIG. 45.
Figure 54:
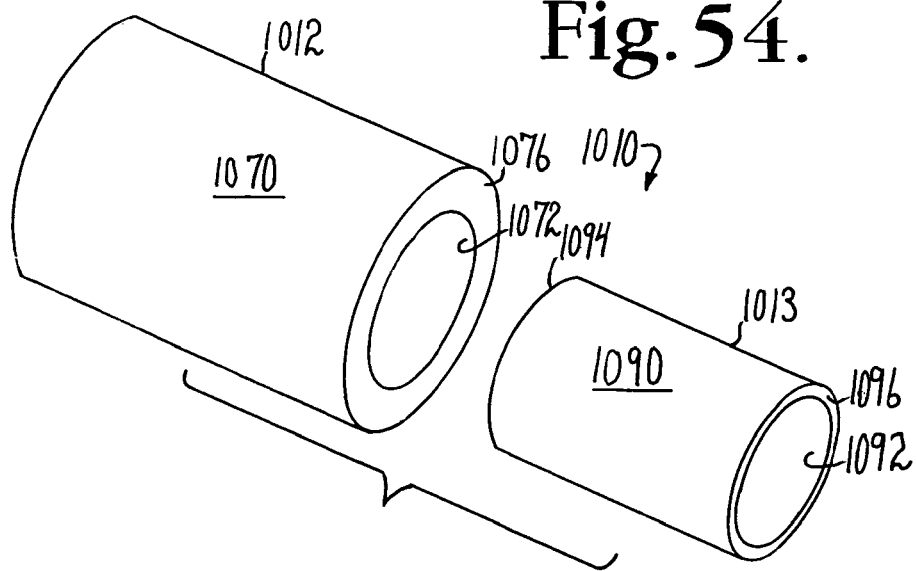
FIG. 54 is an enlarged exploded perspective view of the spacer/liner combination of FIG. 47.
Figure 55:
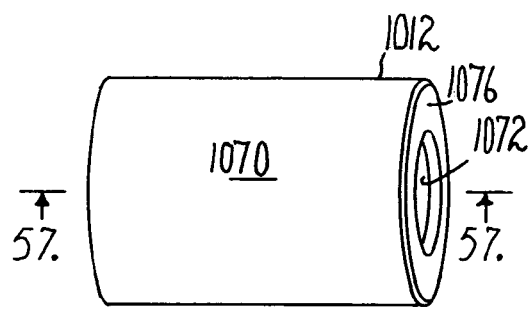
FIG. 55 is an enlarged perspective view of the spacer/liner combination of FIG. 54 shown assembled.
Figure 56:
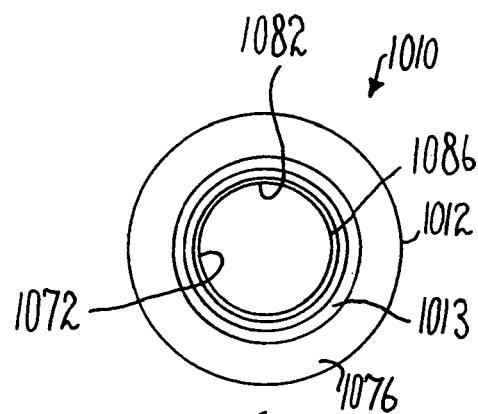
FIG. 56 is an enlarged front elevational view of the spacer/liner combination of FIG. 55.

With particular reference to FIGS. 47 and 48, the sleeve 1005 is then slid onto the cord 1022 at the cord end 1194, with the end 1194 being inserted into the through bore 1034 at the sleeve end 1046 and out the sleeve end 1064. The sleeve 1005 is then fed along the cord 1022 until the sleeve end 1052 is adjacent the enlarged cord end 1192. It is noted that the cord 1022 is typically much longer than shown in the drawing figures and then cut to length near the end 1194 after being fully assembled with the remaining elements of the assembly 1001, tensioned and fixed to the blocker 1018. After the sleeve 1005 is in place on the cord 1022, the spacer/liner combination 1010 is loaded with the cord end 1194 being inserted into the flared opening 1080 at the end 1074, the inner cylindrical surface 1082, the inner cylindrical surface 1084 and thereafter, the liner bore 1092 and out the liner end 1096 and spacer end 1076. The spacer/liner combination 1010 is slid along the cord 1022 until the end 1074 contacts the tubular extension 1032 of the sleeve 1005. A tensioning device (not shown) is typically needed to push and/or pull the spacer 1012 against and over portions of the tubular extension 1032 of the sleeve 1005 until the surface 1074 of the spacer abuts the surface 1047 of the sleeve flange 1037, the inner cylindrical surface 1082 of the spacer 1012 fully engages the outer cylindrical surface 1056 of the tubular extension 1032 and the inner cylindrical surface 1084 of the spacer 1012 fully engages the outer cylindrical surface 1060 of the tubular extension 1032. At this time, the sleeve 1005 is fixed against the spacer 1012 and both the spacer/liner combination 1010 and the sleeve 1005 are in sliding relationship with the cord 1022. It may be necessary to warm the spacer 1012 prior to assembly with the tubular extension 1032 to allow for stretching and expansion of the spacer 1012 graduated inner surface (surfaces 1080, 1082, 1084, and 1086) to fit about the knob defined by the tubular extension annular wall 1058 and cylindrical surface 1060. The sleeve 1007 is then loaded with the cord end 1194 being inserted into the through bore 1104 at the opening surface 1131 near the end 1128 and out the opening 1125 at the end surface 1124. The sleeve 1007 is then slid along the cord 1022 with the tubular extension 1100 sliding into the liner bore 1092. Thereafter, the blocker 1018 with pre-attached bumper 1016 and loosely mated set screw 1019 (as shown in FIGS. 65-67) is loaded onto the cord 1022 with the cord end 1194 being inserted into the bumper bore 1152 at the opening located near the bumper end 1144 and exiting the blocker bore opening near the end surface 1178. The bumper 1016 and attached blocker 1018 are slid along the cord 1022 until the bumper end 1144 abuts against the sleeve 1007 flange 1112 end surface 1124. The resulting loosely held together assembly as shown, for example, in FIG. 48, is now ready for pre-tensioning or for placement in and between the implanted bone screws 1025, followed by tensioning, with the set screw 1019 engaged with the cord 1022 enough to prevent the elements from slipping off of the cord 1022. It is noted that the cord 1022 is typically much longer at this time (than shown in FIG. 48) so that the cord may be grasped and tensioned either before or after the assembly is fixed to the bone screws 1025. If pre-tensioning is desired, at this time, prior to implanting the assembly, a tensioning tool (not shown) known in the art is used to pull upon and put tension on the cord 1022 near the end 1194. The cord 1022 is preferably tensioned until the bumper compresses as shown in FIGS. 45, 46 and 72 and then the set screw 1019 is rotated and driven into the blocker 1018 and up against the cord 1022 using a driving tool (not shown) engaged with the inner drive 1189.

The assembly 1001 (either pre-tensioned or in a loosely attached orientation) is implanted by inserting the sleeve 1005 body portion 1038 into one of the bone screws 1025 with the receiver 1207 being received between the two flanges 1036 and 1037 and placing the sleeve 1007 body portion 1106 into another of the bone screws 1025 with the respective receiver 1207 being received between the two flanges 1110 and 1112. Closure tops 1210 are then inserted into and advanced between the arms 1234 and 1235 of each of the receivers 1207 so as to bias or push against the sleeve 1005 and the sleeve 1007 at respective surfaces 1038 and 1106. A driving tool (not shown) is inserted into each drive 1297 to rotate and drive the respective closure top 1210 into the cooperating receiver 1207. Each shank dome 1226 is engaged by the cooperating insert 1209 and pushed downwardly when the closure top 1210 pushes downwardly on the sleeve 1005 or sleeve 1007. The downward pressure on the shank 1206 in turn urges the retainer 1208 downwardly which exerts both a downward and outward thrust on the retainer 1208 until the retainer surface 1265 fully frictionally engages the receiver inner seating surface 1248. Two polyaxial bone screws 1025, including the dynamic connecting member assembly 1001, are shown in FIGS. 45 and 72, illustrating various shank 1206 to receiver 1207 angular configurations.

If the assembly 1001 has not been pre-tensioned, or if further tensioning is desired, a tensioning tool (not shown) known in the art is then used to pull upon and put tension on the cord 1022 near the end 1194. The cord 1022 is preferably tensioned until the bumper compresses as shown in FIGS. 45 and 72 and then the set screw 1019 is rotated and driven into the blocker 1018 and up against the cord 1022 using a driving tool (not shown) engaged with the inner drive 1189. The blocker 1018 advantageously includes opposed planar sides allowing for the placement of a counter-torque tool for holding the blocker 1018 during tensioning and fixing of the cord 1022 within the blocker. As explained above, the set screw 1019 and blocker 1018 combination include a limited travel feature such that the set screw 1019 is locked into place at a location that firmly holds but does not damage the cord 1022. The cord 1022 is then trimmed to a desired length near the blocker end 1178.

The assembly 1001 is thus substantially dynamically loaded and oriented relative to the cooperating vertebra, providing relief (e.g., shock absorption) and protected movement with respect to flexion, extension, distraction and compressive forces placed on the assembly 1001 and the two connected bone screws 1025. The flanges of the sleeves 1005 and 1007, now located outside of the bone screw receivers 1207 are fully abuttingly engaged with the spacer/liner combination 1010 and/or the bumper 1016, thus fully supporting compression between the spacer 1012 or the bumper 1016 during flexion and extension. Furthermore, during complex spinal movements, the spacer 1012 and 1016 are able to move or flex away from and towards the flanges 1036, 1037 and 1110, 1112 without compromising the strength and integrity of the assembly 1001. It is noted that a problem encountered with dynamic spinal implant systems is the need to provide adequate support with respect to bending sheer. Most spinal movements are not purely bending movements, e.g., flexion and extension. Most movements include both bending and tension, extension or compression. Such bending shear is not well resisted by a cord and spacer alone that performs well in tension, but not when the tension includes a vector force. The present invention advantageously provides a hard, non-elastic extension 1100 of a rigid sliding sleeve body 1099, the extension 1100 further located within a non-elastic liner 1013 of the spacer 1012. Such features protect against vector forces while still allowing for advantageous tension of the cord 1022 as well as improved compression provided by the outer bumper 1016. The cord 1022 and the sleeve 1007 allow for some twisting or turning, providing some relief for torsional stresses. Furthermore, the compressed bumper 1016 and the fixed contact between the sleeve 1005 and the spacer 1012 as well as the fixed contact between the bumper 1016 and the blocker 1018 places some limits on torsional movement as well as bending movement, to provide spinal support. The cord 1022 (in tension) and bumper 1016 (in compression) allow for compression and some extension of the assembly 1001 located between the two bone screws 1025, e.g., shock absorption. Another advantage of some of the embodiments of the present invention is that because of the inelastic sleeve extension that slides within the typically elastic spacer located between two bone screws, the resulting assembly 1001 is more stable than a cord and spacer alone, therefore strength of the assembly does not rely upon the amount of tension placed upon the cord. Therefore, in certain embodiments according to the invention, it is not necessary to place as much tension on the cord 1022 as would be required for a more traditional cord and spacer arrangement, thus protecting the cord from damage of over stressing.

It is also noted that in other embodiments of a connecting member 1001 according to the invention, the sleeve 1005 may be extended at the end 1046 to provide a hard, non-elastic elongate portion for attachment to an additional bone screw or screws, if needed, to provide a connecting member with both dynamic, elastic segments as well as a longer rigid inelastic segment.

If removal of the assembly 1001 from any of the bone screw assemblies 1025 is necessary, or if it is desired to release the assembly 1001 at a particular location, disassembly is accomplished by using the driving tool (not shown) with a driving formation cooperating with the closure structure 1210 internal drive 1297 to rotate and remove the closure structure 1210 from the receiver 1207. Disassembly is then accomplished in reverse order to the procedure described previously herein for assembly.

Eventually, if the spine requires more rigid support, the connecting member assembly 1001 according to the invention may be removed and replaced with another longitudinal connecting member, such as a solid rod or bar, having the same width or diameter as body portions of the sleeves 1005 and 1007, utilizing the same receivers 1207 and the same or similar closure structures 1210. Alternatively, if less support is eventually required, a less rigid, more flexible assembly, for example, an assembly 1001 having a spacer 1012 and bumper 1016 made of a softer more compressible material than the spacer and bumper being replaced thereby, also utilizing the same bone screws 1025.

With reference to FIGS. 89-95, an alternative longitudinal connecting member assembly according to the invention, generally 1301, for use with three bone screws 1025 includes a first sleeve 1305, a second sleeve 1307, a third sleeve 1309, a first spacer/liner combination 1310 and a second spacer/liner combination 1311. The first spacer/liner combination 1310 includes an outer spacer 1312 and an inner liner 1313 and the second spacer/liner combination 1311 includes an outer spacer 1314 and an inner liner 1315. The illustrated spacer/liner combination 1311 is identical to the spacer/liner combination 1310 with the exception of a length thereof along a central axis A'. The assembly 1301 further includes a bumper 1316, a cord blocker 1318 and mating set screw 1319 and a cord 1322. The assembly 1301 is substantially similar to the assembly 1001 with the exception of the addition of the third sleeve 1309 and the second spacer/liner combination 1311. Thus, the first sleeve 1305, the second sleeve 1307, the first spacer/liner combination 1310, the bumper 1316, the cord blocker 1318, the set screw 1319 and the cord 1322 are the same or substantially similar to the respective first sleeve 1005, second sleeve 1007, spacer/liner combination 1010, bumper 1016, cord blocker 1018, set screw 1019 and cord 1022 of the assembly 1001 previously discussed above and thus shall not be discussed further herein. Although only one additional sleeve 3109 (and attached bone screw 1025) and cooperating spacer/liner 1311 are illustrated in the drawings, it is noted that the assembly 1301 of the invention may be lengthened further and adapted for use with additional bone screws by simply adding more sleeves 1309 and cooperating spacer/liners 1311 (or optionally spacers without liners) between the sleeve 1305 and the sleeve 1307.

With particular reference to FIGS. 91-94, the sleeve 1309 includes a body portion 1330 generally sized and shaped for being received within the polyaxial bone screw 1025 and a first tubular extension 1332 sized and shaped to engage and hold the spacer 1312 in fixed engagement with the sleeve 1309. The sleeve also includes a second opposed tubular extension 1333 sized and shaped to be slidingly received by the spacer/liner combination 1311. The illustrated body portion 1330 and tubular extensions 1332 and 1333 are integral or otherwise fixed to one another. A through bore 1334 extends centrally through the body portion 1330 and centrally through both the tubular extensions 1332 and 1333 along the axis A'. The bore 1334 is sized and shaped to slidingly receive the cord 1322 and when assembled with a remainder of the assembly 1301, also extending along the axis A'. The body portion 1330 further includes a cylindrical body surface 1338 located between radially extending flanges 1340 and 1342, the flanges also being cylindrical in shape. The flanges 1340 and 1342 further include respective inner planar surfaces 1344 and 1346, respective outer cylindrical surfaces 1348 and 1350 and respective outer planar surfaces 1352 and 1354. The flanges 1340 and 1342 are spaced from one another a desired distance so as to closely receive a bone screw receiver 1207 therebetween. The flanges 1340 and 1342 are thus identical or substantially similar in form and function to the flanges 1036 and 1037 of the sleeve 1005 and the flanges 1110 and 1112 of the sleeve 1007 previously described herein with respect to the assembly 1001.

The outer planar surface 1354 is adjacent to a tapered surface 1355 that extends toward and terminates at a first cylindrical surface 1356 of the tubular extension 1332. The outer cylindrical surface 1356 terminates at a radially extending annular wall 1358 that is perpendicular thereto. The wall 1358 terminates at a second substantially cylindrical surface 1360 of greater outer diameter than the cylindrical surface 1356. The surface 1360 terminates at an annular inwardly tapering beveled surface 1362. The bevel 1362 is adjacent to a planar annular end surface 1364 that is disposed perpendicular to the cylindrical surface 1360. The surface 1364 is adjacent to a flared or beveled surface 1365 that defines an opening of the bore 1334. The surfaces 1356, 1358 and 1360 provide a push-on connective element for attachment to inner surfaces of the spacer 1312. The sleeves 1305, 1307, 1309, the liners 1313 and 1315 and the cord blocker 1318 with set screw 1319 may be made from a variety of inelastic materials, including, but not limited to metals, metal alloys, including cobalt chromium, and inelastic plastics including, but not limited to plastic polymers such as polyetheretherketone (PEEK), ultra-high-molecular weight-polyethylene (UHMWP), polyurethanes and composites, including composites containing carbon fiber and layers of different materials.

Near the tubular structure 1333, the flange 1340 outer planar surface 1352 is adjacent to a tapered surface 1366 that extends toward and terminates at a cylindrical surface 1367 of the tubular extension 1333. The outer cylindrical surface 1367 extends toward an annular planar end surface 1368 that is perpendicular thereto. A beveled surface 1370 spans between the cylindrical surface 1367 and the end surface 1368. The end surface 1368 terminates at a inner flared surface 1371, the surface 1371 defining an opening of the bore 1334. Upon assembly with the spacer 1314/liner 1315 combination, the cylindrical surface 1367 is in slidable relationship with the inner surface of the liner 1315. A desirable material for both the liner 1315 and the tubular extension 1333 is cobalt chromium. Furthermore, in some embodiments of the invention, in order to have low or no wear debris, the liner 1315 inner surface and the outer surface 1367 of the tubular extension 1333 may be coated with an ultra thin, ultra hard, ultra slick and ultra smooth coating, such as may be obtained from ion bonding techniques and/or other gas or chemical treatments.

Figure 90:
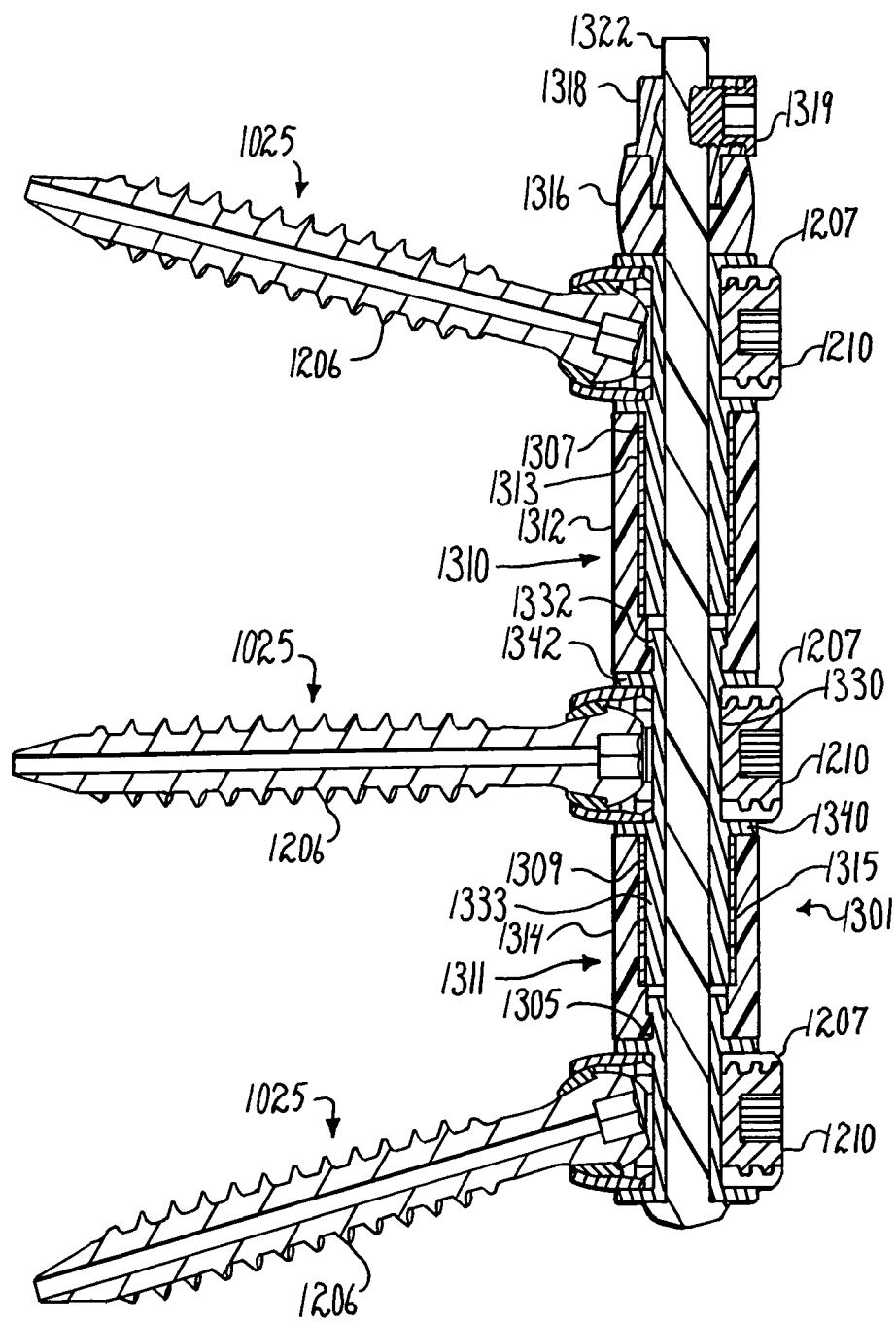
FIG. 90 is a side elevational view of the connecting member of FIG. 89 with portions broken away to show the detail thereof, including an inner cord, three sleeves, two spacer/liner combinations, an elastic bumper and a cord blocker with set screw.
Figure 91:
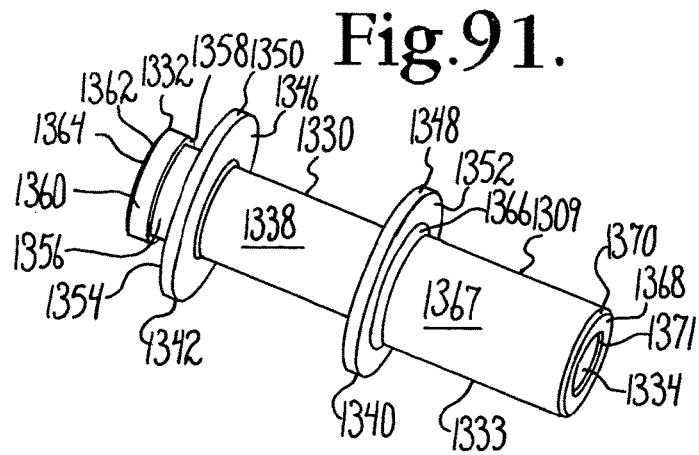
FIG. 91 is an enlarged perspective view of one of the sleeves of FIG. 90.
Figure 92:
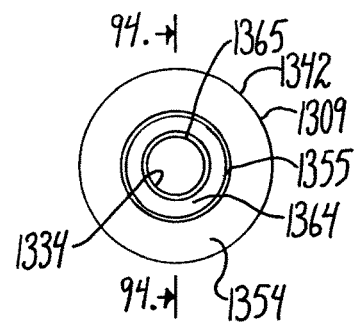
FIG. 92 is an enlarged rear elevational view of the sleeve of FIG. 91.
Figure 94:
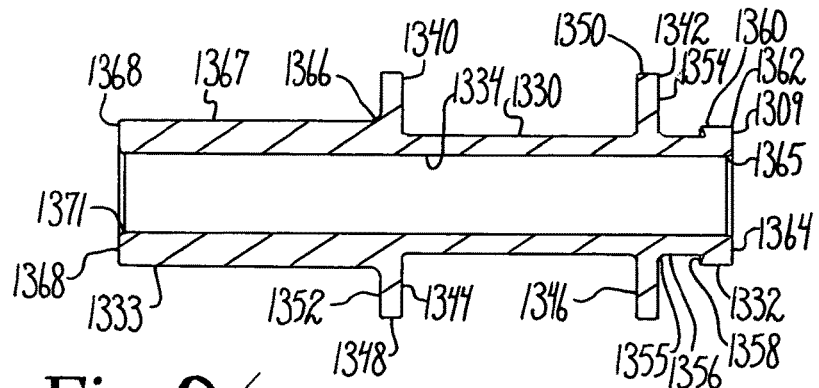
FIG. 94 is an enlarged cross-sectional view taken along the line 94-94 of FIG. 92.
Figure 93:
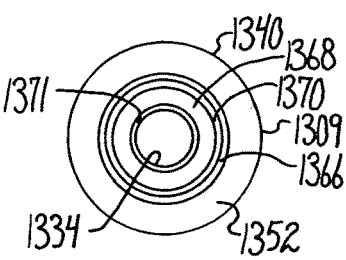
FIG. 93 is an enlarged front elevational view of the sleeve of FIG. 91.

As stated above, the spacer/liner combination 1311 is identical to the spacer/liner combination 1310 with the exception of length along the axis A'. Thus, the spacer/liner combination 1311 is identical or substantially similar to the spacer/liner combination 1010 previously described herein. With reference to FIG. 90, during assembly, the spacer 1312 is press-fitted over the tubular extension 1332 of the sleeve 1309 while the spacer 1314 is press fitted over the tubular extension of the sleeve 1305. Thus, the elements are loaded onto the cord 1322 as follows: the sleeve 1305, followed by the spacer/liner combination 1311, followed by the sleeve 1309, followed by the spacer/liner combination 1312 followed by the sleeve 1307, followed by the bumper 1316 and attached blocker 1318 with set screw 1319. The assembly 1301 is implanted with each of the sleeves 1305, 1307 and 1309 being attached to a bone screw 1025 as shown in FIG. 90. Either before or after the sleeves are attached to the bone screws 1025, the cord 1322 is tensioned as previously described with respect to the assembly 1001. Thus, the fully assembled and dynamically loaded assembly 1301 allows for translation of the receivers 1207 of all three of the bone screws 1025 along the tensioned cord 1322 while at the same time all three sleeves 1305, 1307 and 1309 are fixedly coupled to a respective bone screw receiver 1207. Furthermore, the tubular extension 1333 of the sleeve 1309 as well as the tubular extension of the sleeve 1307 glide within spacer/liner combinations 1310 and 1311, protecting the assembly from bending shear forces while allowing for the desired movement of all three screws 1025 with respect to the tensioned cord 1322.

With reference to FIG. 95, a portion of a kit according to the invention is shown showing three different sized sleeves 1307, the shortest being identified as 1307, a mid-length sleeve as 1307' and a longer sleeve as 1307". The kit also illustrates three different sized sleeves 1309 with the shortest being identified as 1309, the mid-length sleeve as 1309' and the longest sleeve 1309". One size sleeve 1305 is illustrated. Thus, as described previously with respect to the assembly 1001, when utilizing the assembly 1301 a surgeon may choose various lengths of sleeves 1307 and 1309 that best match the measurements made of distances between a patient's vertebrae.

Figure 96:
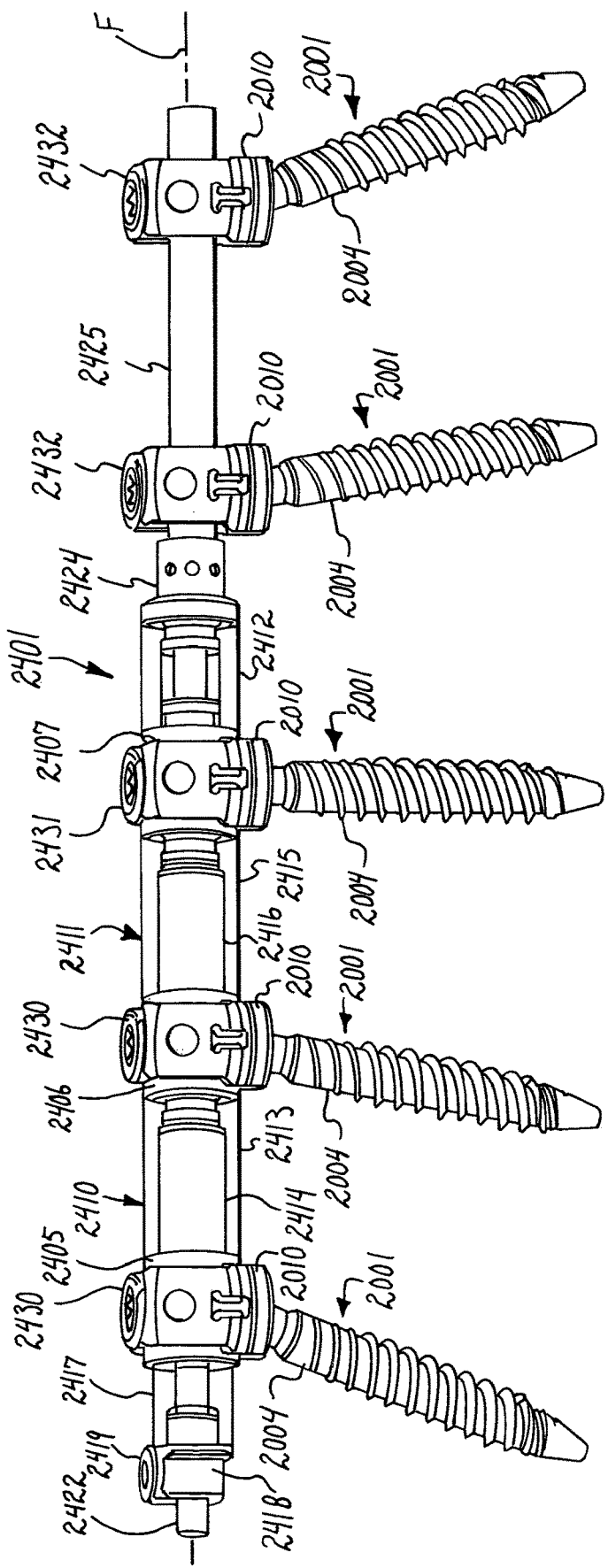
FIG. 96 is a perspective view of another longitudinal connecting member according to the invention shown attached to five polyaxial bone screws.
Figure 98:
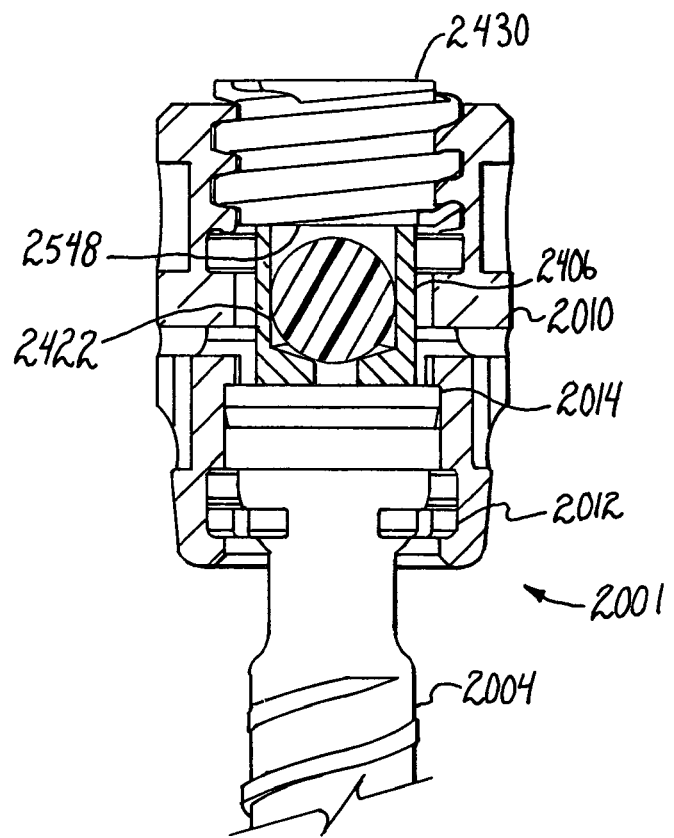
FIG. 98 is a front elevational view of one of the bone screws shown in FIG. 96 with portions broken away to show cooperation with the connecting member of FIG. 96, also with portions broken away.
Figure 99:
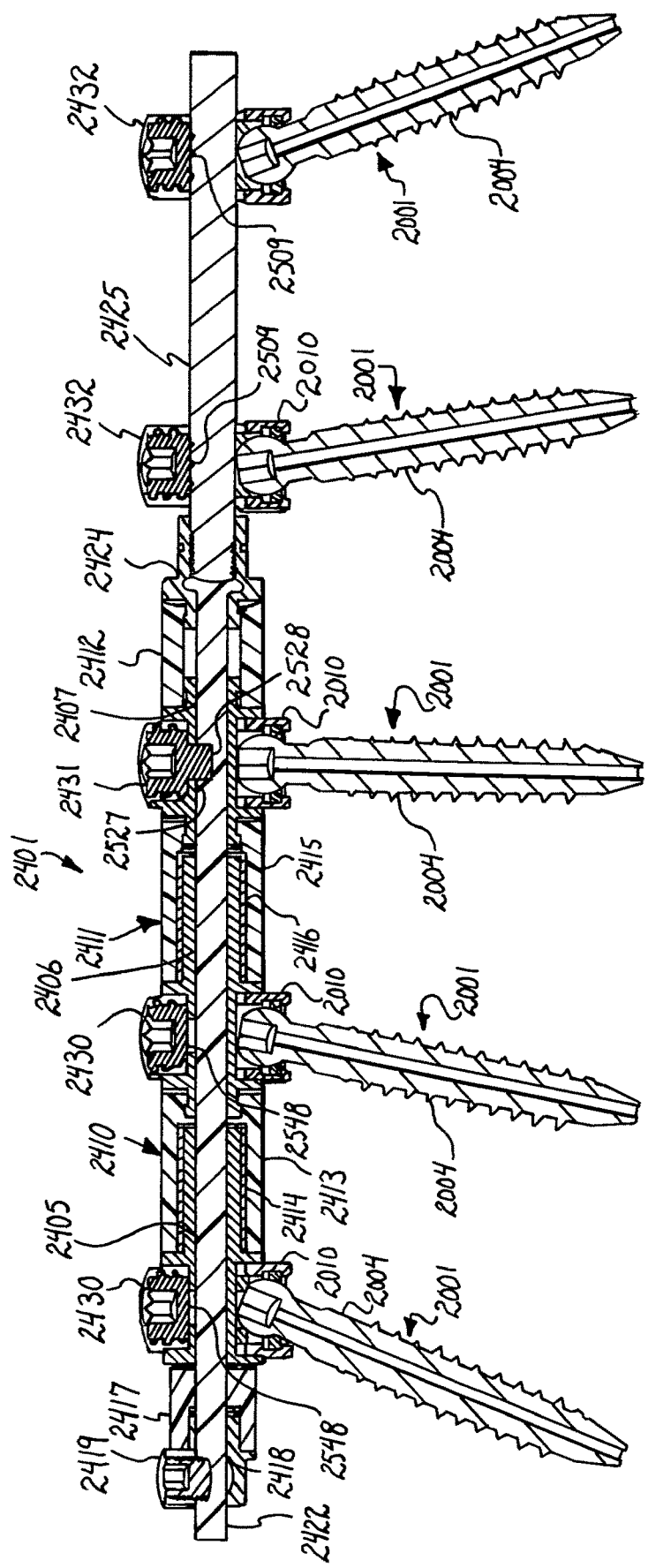
FIG. 99 is a front elevational view of the connector and bone screws of FIG. 96 with portions broken away to show the detail thereof and showing three different types of closure tops.
Figure 100:
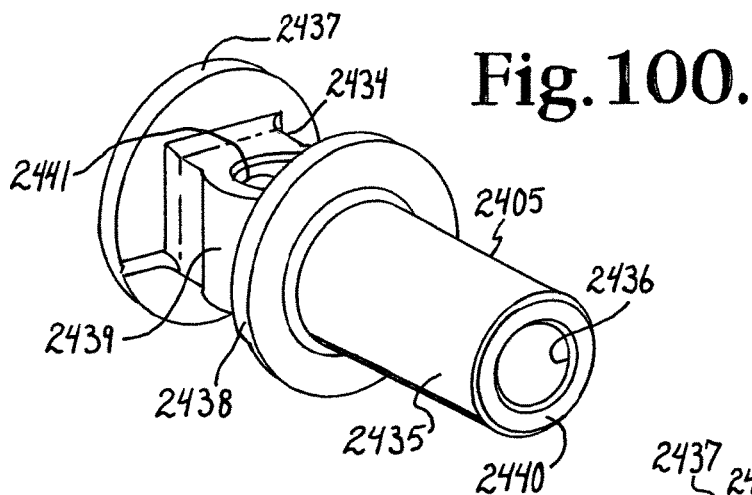
FIG. 100 is an enlarged perspective view of the first sleeve shown in FIG. 97.
Figure 102:
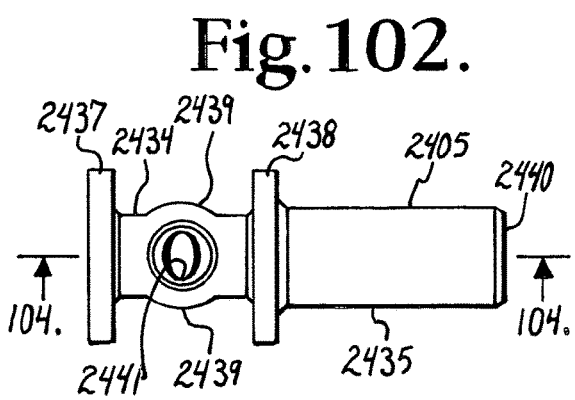
FIG. 102 is a reduced top plan view of the sleeve of FIG. 100.
Figure 101:
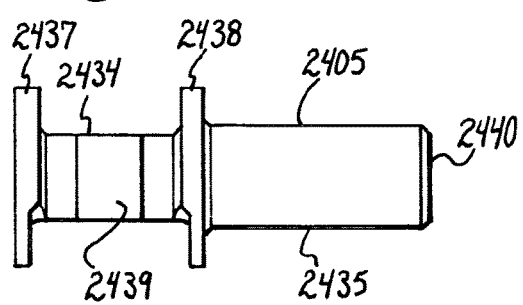
FIG. 101 is a reduced side elevational view of the sleeve of FIG. 100.
Figure 103:
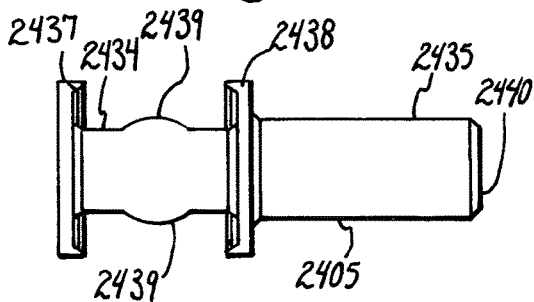
FIG. 103 is a reduced bottom plan view of the sleeve of FIG. 100.
Figure 104:
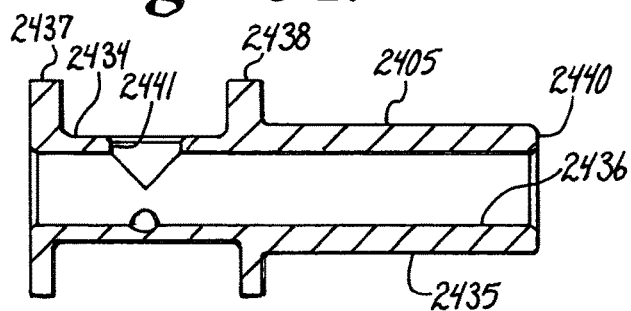
FIG. 104 is a cross-sectional view taken along the line 60-60 of FIG. 100.

With reference to FIGS. 96-122 another longitudinal connecting member assembly according to the present invention, generally 2401 is shown attached to five polyaxial bone screws 2001. Generally, each bone screw includes a shank 2004, a receiver 2010, an open retainer 2012 for holding the shank 2004 upper portion 2008 within the receiver 2010 and an insert 2014 having a substantially planar top surface for engagement with sleeves of the assembly 2401. The connecting member assembly 2401 is elongate, having a substantially central axis F. With particular reference to FIGS. 96-99, the illustrated connecting member assembly 2401 generally includes at least first, second and third hard, inelastic flanged sleeves 2405, 2406 and 2407 with a first spacer/liner combination, generally 2410, a second spacer/liner combination, generally 2411 and a third spacer 2412 located therebetween. It is noted that the spacer/liner combinations may be replaced by a spacer alone in other embodiments of the invention. The illustrated first spacer/liner combination 2410 includes an outer spacer 2413 and an inner liner 2414 and the second spacer/line combination 2411 includes an outer spacer 2415 and an inner liner 2416. The assembly 2401 further includes an elastic bumper 2417, a cord blocker 2418 with cooperating set screw 2419 and an inner core that in the present embodiment is a cord 2422. The assembly 2401 further includes a cord/rod coupler 2424 and a threaded rod 2425. The cord 2422 extends from the cord/rod coupler 2424 along the axis F and successively through and within the spacer 2412, the sleeve 2407, the spacer 2415, the sleeve 2406 (and spacer/liner 2411), the spacer 2413, the sleeve 2405 (and spacer/liner 2410), the bumper 2417 and the cord blocker 2418 as shown, for example, in FIG. 99. In FIGS. 96 and 99, the assembly 2401 is shown attached to three polyaxial bone screws, generally 2001, described more fully below at the sleeves 2405, 2406 and 2407. As best shown in FIG. 99, two of the bone screws 2001 are attached to the sleeves 2405 and 2406 with a slide or slipping closure top 2430 and one of the bone screws is attached to the sleeve 2407 with a gripping closure top 2431. As will be discussed in greater detail below, the slide or slip closure top 2430 engages a respective sleeve but not the cord 2422, allowing the cord to slip or slide within the polyaxial screw 2001. The grip closure top 2431 extends through the sleeve and grips and fixes the cord 2422 against a surface of the sleeve and thus fixes the cord in relation to the polyaxial screw 2001. Finally, two of the illustrated bone screws 2001 are attached to the rod 2425 with a point and rim closure top 2432. The closure tops 2430, 2431 and 2432 are shown in greater detail in FIGS. 117-122.

A portion of the sleeve 2405 extends into and through the spacer/liner 2410 and is in slidable relationship therewith. Likewise, a portion of the sleeve 2406 extends into and through the spacer/liner 2411. Such spacer overlap with respect to the sleeves 2405 and 2406 provides advantageous anti-shear support for the connector 2401. A portion of the cord blocker 2418 also extends into a bore of the bumper 2417. The bumper 2417 is typically made from an elastomer while the outer spacers 2412, 2413 and 2415, although typically elastomeric, may be made from a material with a different durometer, typically (but not always) being tougher and less compressible than the material of the bumper 2417. The sleeves 2405, 2406 and 2407 and the spacer liners 2414 and 2416 are made from a hard, non-elastic material, such as a metal or metal alloy, like cobalt chromium. The hard and stiff sliding sleeves 2405 and 2406 each include an extension that slides into the respective liner 2414 and 2416, providing a dynamic no- or low-wear, sliding relationship between the sleeves and respective cooperating liners that is non-binding, and provides excellent shear resistance while at the same time, the optional thin liners 2414 and 2416 cooperating with the respective elastomeric spacers 2412, 2413 and 2415 as well as the tensioned cord 2422 provide controlled bending, with the tensioned cord 2422 and compressed bumper 2417, performing well under tension and compression. Flanged portions of the sleeves 2405, 2406 and 2407 are located on either side of the bone screw receivers 2010, the flanges abutting against the spacers 2412, 2413, 2415 or the bumper 2417, the flanges extending radially outwardly to an extent to fully engage ends of adjacent spacers or the bumper 2417, resulting in a stable, secure, substantially full contact between the individual elements of the assembly 2401. Furthermore, the flanges allow for assembly and dynamic setting of the assembly prior to implantation, if desired, with the cord 2422 being placed in tension and at least the bumper 2417 being placed in compression. In some embodiments of the invention, tensioning of the cord 2422 and compression of the bumper 2417 and optionally the spacers 2412, 2413 and 2415 may be performed after the assembly 2401 is attached to the bone screws 2001. It is noted that in some embodiments of the invention, the bumper 2417 and cooperating blocker 2418 may be eliminated and a gripping closure top 2431 may be inserted at an end or terminal bone screw 2001 for gripping and fixing the cord in tension.

With particular reference to FIGS. 100-104, the sleeve 2405 further includes a body portion 2434 generally sized and shaped for being received within the polyaxial bone screw 2001 receiver 2010 and a tubular extension 2435 sized and shaped to be slidingly received in the spacer/liner combination 2410. The illustrated body portion 2434 and tubular extension 2435 are integral or otherwise fixed to one another. A through bore 2436 extends centrally through the body portion 2434 and centrally through the tubular extension 2435. The bore 2436 is sized and shaped to slidingly receive the cord 2422 and when assembled with a remainder of the assembly 2401, extends along the axis F. The body portion 2434 further includes a pair of spaced radially extending flanges 2437 and 2438 with a partially cylindrical and partially planar body portion being located therebetween, the body portion having an enlarged or protruding portion or portions illustrated as opposed substantially cylindrical extensions 2439, sized and shaped to closely fit within a cylindrical surface portion of the bone screw receiver 2010. The portions 2439 function to center the sleeve within the bone screw receiver 2010 and also advantageously strengthen the sleeve, resulting in better load transfer. It is foreseen that in some embodiments of the invention, the body 2434 with centering structure 2439 may be configured to also extend down into the receiver and abut the bone screw shank upper portion 2008 and thus eliminate the compression insert 2014. Furthermore, in some embodiments, the flanges 2437 and 2438 may be reduced or eliminated as the centering of the sleeve with respect to the bone screw receiver 2010 is performed by the portion or portions 2439.

In the illustrated embodiment, the flanges 2437 and 2438 are substantially cylindrical having opposed planar and annular side surfaces spaced for closely receiving the bone screw 2001 receiver 2010. The flange 2437 also defines an end of the sleeve while the flange 2438 is located at a juncture of the body 2434 and the tubular extension 2435. The body portion 2439 is sized and shaped to be receivable within and frictionally fixed to a variety of monoaxial or polyaxial screw heads or receivers, including the receiver 2010. At an end 2440, the sleeve 2405 (and optional liner) may be cut to length. A bore 2441 is formed in the body 2434 between the flanges 2437 and 2438, the bore 2441 communicating with the through bore 2436. The bore 2439 is sized and shaped to receive the closure top 2431 therein for frictionally gripping the cord 2422 against an internal surface defining the through bore 2436, and thus placing the cord 2422 in fixed relation with the bone screw receiver 2010, if desired.

The sleeve 2405, as well as the sleeves 2406 and 2407, the liners 2414 and 2416, the cord blocker 2418 with set screw 2419 and the cord/rod coupler 2424 may be made from a variety of inelastic materials, including, but not limited to metals, metal alloys, including cobalt chromium, and inelastic plastics including, but not limited to plastic polymers such as polyetheretherketone (PEEK), ultra-high-molecular weight-polyethylene (UHMWP), polyurethanes and composites, including composites containing carbon fiber and layers of different materials.

The spacers 2412, 2413 and 2415 are each substantially cylindrical in form, having outer cylindrical surfaces and inner through bores of a substantially constant inner diameter for receiving a sleeve portion and/or liner 2414 or 2416 and having graduated or various inner diameters at an end thereof for overlapping and fixing to a sleeve or the cord/rod coupler. The optional liner 2414 closely fits within the through bore of the spacer 2413 and the liner optional 2416 closely fits within the through bore of the spacer 2415. In fact, the spacer/liner combination 2410 and the spacer/liner combination 2411 are typically assembled or manufactured with the respective liner being fixed to the inner surface defining the bore of the spacer such that a surgeon receives such a spacer/liner combination already assembled and ready for the surgeon to cut the spacer/liner combination to a desired length at a non-graduated end thereof that is adhered or otherwise fixed the liner, as will be described in greater detail below. The spacers 2412, 2413 and 2415 are typically elastic and made from a plastic, for example, a thermoplastic elastomer made from a polyurethane or polyurethane blend, such as a polycarbonate urethane. The spacers 2413 and 2415 include respective various and graduated inner end surfaces 2442 and 2443 that are sized and shaped to be press fit over a knobbed feature of an adjacent sleeve or cord/rod coupler as will be described in greater detail below. The spacer 2412 also includes such a knob receiving feature on one or both ends thereof.

The optional inelastic liners 2414 and 2416 are substantially cylindrical and tubular in form, having a constant outer cylindrical surface and a constant inner cylindrical through bore. An end surface of each liner is disposed flush to the respective overlapping spacer, such surfaces being the cut-to-length side of the spacer/liner combination. The liners 2414 and 2416 may be made from a variety of non-elastic materials, including metals, metal alloys and some plastics, with cobalt chromium being a preferred material. As stated above, the inner cylindrical surfaces of the liners are sized and shaped to slidingly receive a tubular extension of the inelastic sleeves 2405 or 2406.

Figure 105:
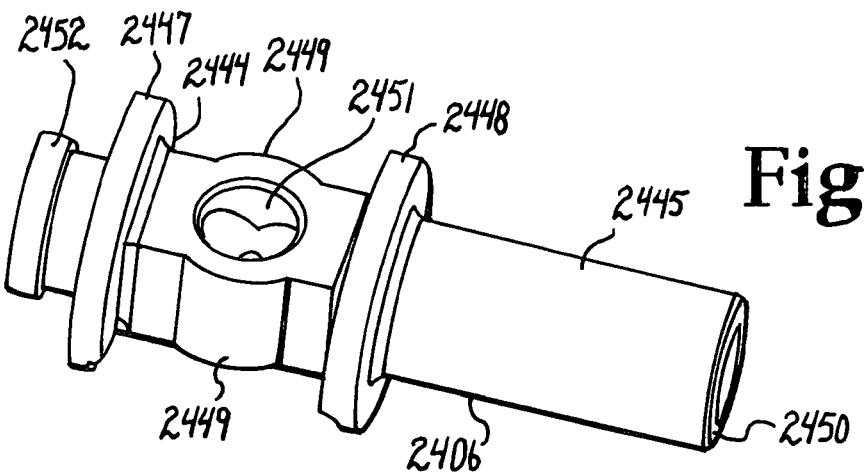
FIG. 105 is an enlarged perspective view of the second sleeve shown in FIG. 97.
Figure 106:
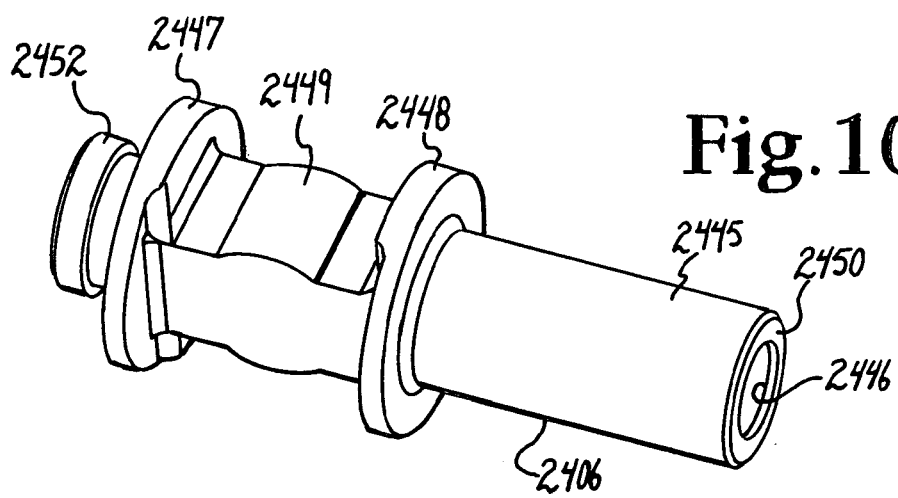
FIG. 106 is an alternative perspective view of the sleeve of FIG. 105.
Figure 107:
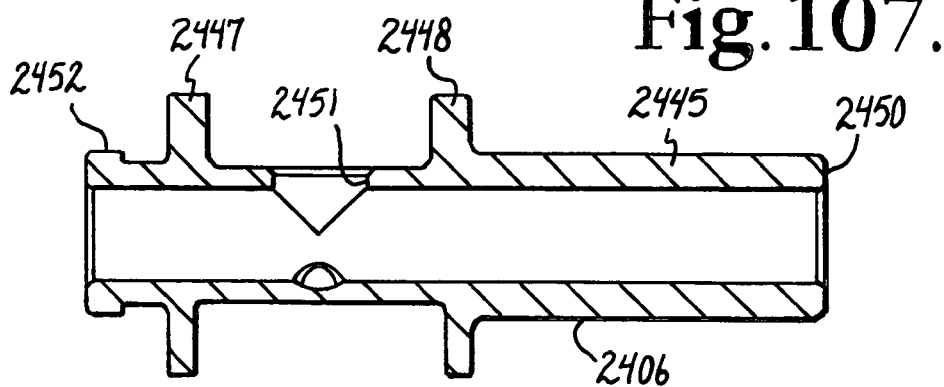
FIG. 107 is a side elevational view of the sleeve of FIG. 105 with portions broken away to show the detail thereof.

With particular reference to FIGS. 105-107, the sleeve 2406 includes a body 2444, a tubular extension 2445, a through bore 2446, flanges 2447 and 2448 with a centering body portion 2449 therebetween, an end 2450 and a closure top receiving bore 2451 that are substantially the same or similar in form and function to the respective body 2434, tubular extension 2435, through bore 2436, flanges 2437 and 2438, body portion 2439, end 2440 and closure top receiving bore 2441 previously described herein with respect to the sleeve 2405. Unlike the sleeve 2405 wherein the flange 2437 defines one end of the sleeve, the sleeve 2406 includes a knobbed structure 2452 disposed near the flange 2447 and opposite the end 2450. The knobbed structure 2452 provides a push-on connective element for attachment to inner graduated surfaces 2442 of the spacer 2413. It is noted that more than one size of sleeve 2405 and/or 2406 is typically provided to the surgeon, the sleeves differing only in the length of the tubular extension 2435 or 2445, so as to appropriately match the size of the patient's spine. Also, a desirable material for both the liners and the sleeve tubular extensions is cobalt chromium. Furthermore, in some embodiments of the invention, in order to have low or no wear debris, the liner inner surface and the outer surfaces of the sleeve tubular extensions may be coated with an ultra thin, ultra hard, ultra slick and ultra smooth coating, such as may be obtained from ion bonding techniques and/or other gas or chemical treatments. It is further noted that inner surfaces of the sleeves that receive the cord 2422 may also be likewise coated to provide a slick, low to no wear debris interface with the cord 2422.

Figure 108:
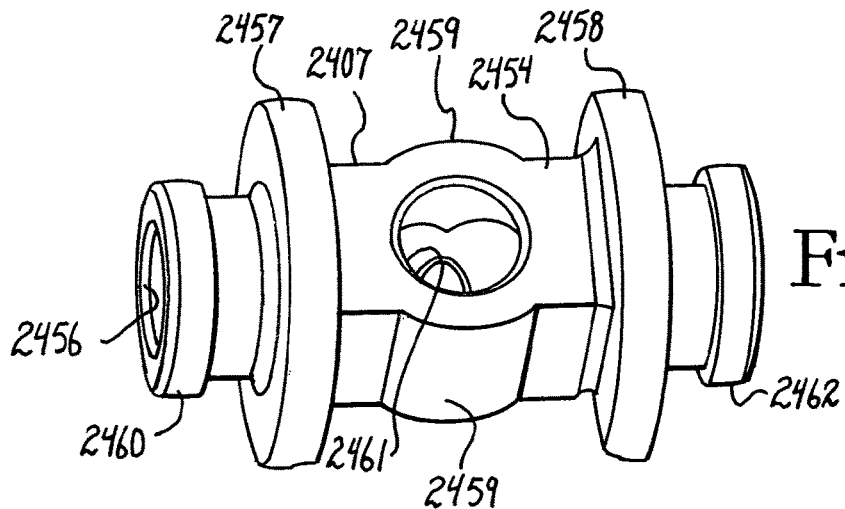
FIG. 108 is an enlarged perspective view of the third sleeve shown in FIG. 97.
Figure 109:
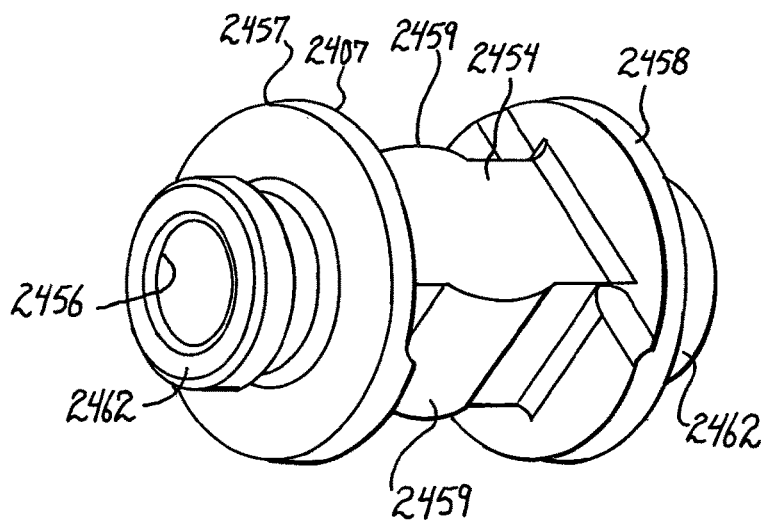
FIG. 109 is an alternative perspective view of the sleeve of FIG. 108.
Figure 110:
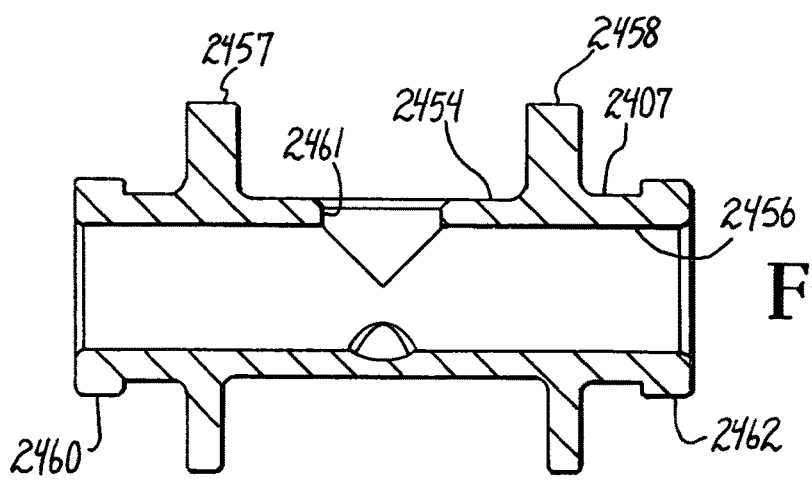
FIG. 110 is a side elevational view of the sleeve of FIG. 108 with portions broken away to show the detail thereof.

With particular reference to FIGS. 108-110, the sleeve 2407 includes a body 2454, a through bore 2456, flanges 2457 and 2458 with a centering body portion 2459 therebetween, and a closure top receiving bore 2461 that are substantially the same or similar in form and function to the respective body 2434, through bore 2436, flanges 2437 and 2438, body portion 2439, and closure top receiving bore 2441 previously described herein with respect to the sleeve 2405. Unlike the sleeves 2405 or 2406, the sleeve 2407 includes knobbed structures 2460 and 2462 disposed at either end thereof. The knobbed structures 2460 and 2462 are the same or similar to the knobbed structure 2452 described above with respect to the sleeve 2406, providing a push-on connective element for attachment to inner graduated surfaces 2443 of the spacer 2415 and slidable connection to an inner surface of the spacer 2412. It is foreseen that the spacer 2412 may include graduated surfaces to provide for a fixed or press fit connection between the sleeve 2407 and the spacer 2412.

The bumper 2417 is substantially cylindrical and tubular in form, having an outer cylindrical surface and an inner, graduated through bore. The bumper 2417 has opposed substantially planar annular end surfaces. An inner cylindrical surface of the bore is sized and shaped to closely receive a tubular extension of the cord blocker 2418. The bumper 2417 is elastic and may be made from a variety of compressible and stretchable materials, including, but not limited to natural or synthetic elastomers such as polyisoprene (natural rubber), and synthetic polymers, copolymers, and thermoplastic elastomers, for example, polyurethane elastomers such as polycarbonate-urethane elastomers. In order to have low or no wear debris, the bumper inner surface may also be coated with an ultra thin, ultra hard, ultra slick and ultra smooth coating, such as may be obtained from ion bonding techniques and/or other gas or chemical treatments.

Figure 97:
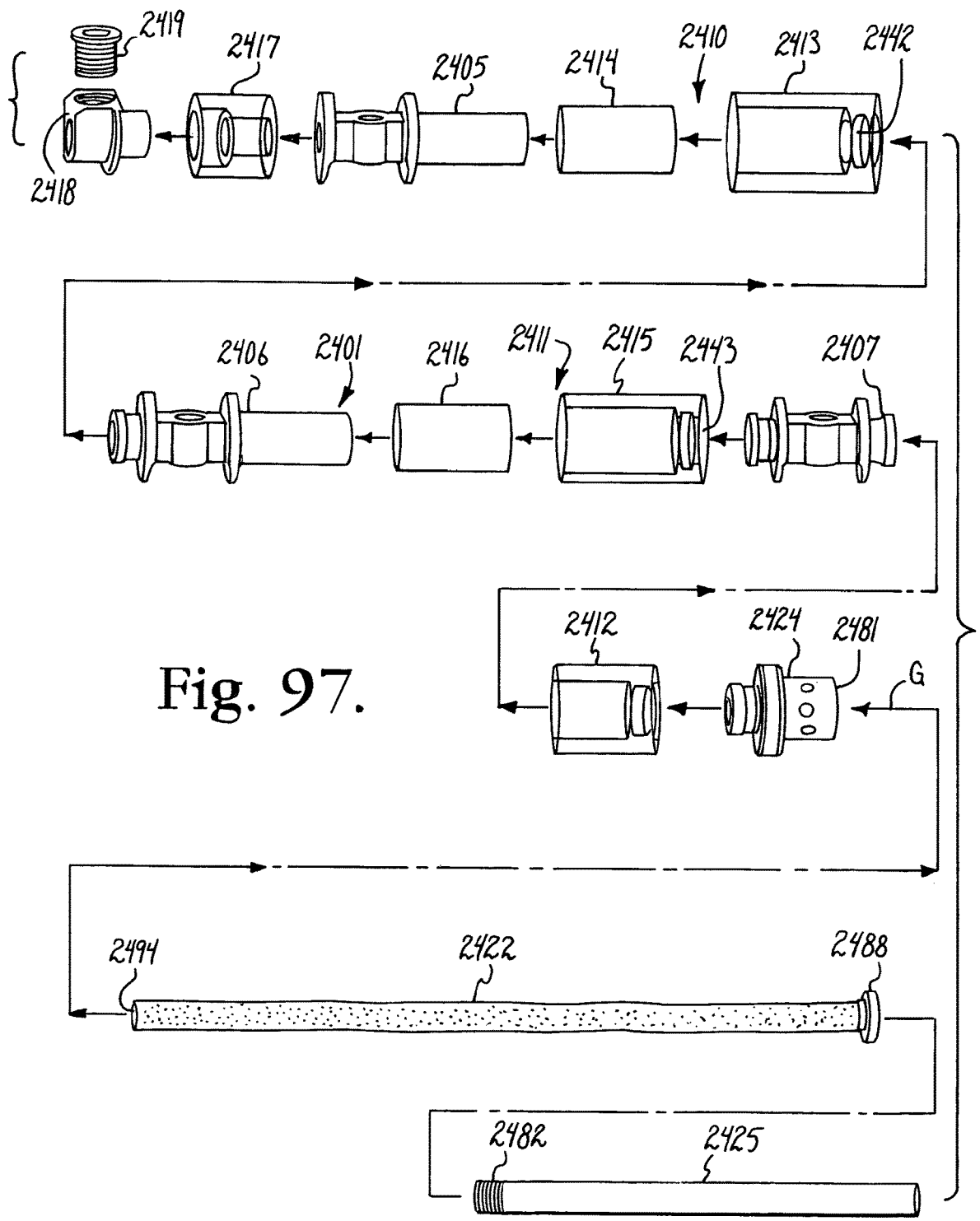
FIG. 97 is an exploded perspective view of the connecting member of FIG. 96 shown without the polyaxial bone screws, the connecting member including an inner cord, first, second and third sleeves, first and second spacer/liner combinations, a third spacer, an elastic bumper, a cord blocker with set screw, a rod/cord coupler and a threaded rod.

With reference to FIGS. 97, 113 and 114, the cord blocker 2418 and cooperating set screw 2419 are shown. The blocker 2418 includes a body portion 2469 and a tubular extension 2470 sized and shaped to be slidingly received in the bumper 2417. The illustrated body portion 2469 and tubular extension 2470 are integral or otherwise fixed to one another. A through bore 2474 extends through a lower portion of the body portion 2469 and centrally through the tubular extension 2470. The bore 2474 is sized and shaped to receive the cord 2422 and when assembled with a remainder of the assembly 2401 extends along the axis F. Formed in the body portion 2469 is a threaded bore 2475 sized and shaped to receive and threadably mate with a thread of the set screw 2419. The threaded bore 2475 communicates with the through bore 2474 and is substantially perpendicular thereto. A surface 2476 partially defining the bore 2474 includes a depression 2477, sized and shaped for receiving the cord 2422 therein when the set screw 2419 engages the cord 2422. The sleeves 2405, 2406 and 2407 also include such a depression for receiving the cord 2422 within bores thereof when the grip closure top 2431 is used to clamp the cord 2422 within the sleeve without damaging or destroying the cord 2422.

It is noted that the blocker 2418 and set screw 2419 combination is typically provided with the bumper 2417 pre-attached thereto and handled as a unit assembly. Thus, prior to being received by the surgeon, the bumper 2417 is wedged and in some cases adhered or otherwise fixed onto the tubular extension at the factory, with the inner surface of the bumper frictionally engaging the surface 2470 of the blocker 2418 and the bumper 2417 abutting against and fixed to the blocker body 2469.

With reference to FIGS. 97, 111 and 112, the cord/rod coupler 2424 is shown. The coupler 2424 includes a centrally located cylindrical body portion 2479 a tubular extension 2480 having an inner thread 2481 for mating with a thread 2482 of a hard surfaced rod 2425 and a knob feature 2483 sized and shaped for press fit engagement with the spacer 2412. A central bore 2485 extends through the knob, body and tubular extension, the thread 2481 partially defining the bore 2485. The bore 2485 is sized and shaped to receive the cord 2422 and when assembled with a remainder of the assembly 2401 extends along the axis F. Formed in the body portion 2479 is a recess 2486 sized and shaped to hold an end knot or knob 2488 of the cord 2422 therein, the bore 2485 located at the knobbed coupler end 2483 being of smaller diameter than a remainder of the bore 2485 and thus forming a restriction, prohibiting movement of the cord knot or knob 2488 from passing into the bore 2485 at the knobbed end 2483.

With particular reference to FIG. 97, the illustrated cord 2422 includes an elongate body 2490 with an enlargement shown in the form of a knot or knob 2488 at one end thereof and an opposed cut-to-length end 2494. The enlarged end 2488 may be created by heating the cord 2422 to melt the cord and create such feature that is slidable through the threaded portion 2481 of the cord/rod coupler 2424 but is otherwise captured within the recess 2486 of the coupler 2424 and is too large to enter the bore 2485 at the knobbed portion 2483 of the coupler 2424. Alternatively a pin may be fixed to the cord 2422. In other embodiments of the invention that do not include a rod/cord coupler 2424, a blocker and set screw combination, similar to the blocker 2418 and set screw 2419 may be used to fix the cord 2422 outside of the sleeve 2407 and/or spacer 2412. The cord 2422 may be made from a variety of materials, including polyester or other plastic fibers, strands or threads, such as polyethyleneterephthalate. A cord according to the invention typically does not illustrate elastic properties, such as any significant additional axial distraction and lengthening after the assembly 2401 is operatively assembled and the cord is tensioned. However, it is foreseen that in some embodiments, the cord 2422 may be made of an elastic or semi-elastic material, such as a plastic or rubber (natural or synthetic) having at least some elastic properties, allowing for some further distraction of the assembly 2401 during operation thereof. The core can also be a cable-like structure made of metal.

With reference to FIGS. 117-122, various closure tops for use with the bone screw assemblies 2001 and the connecting assembly 2401 are shown. The bone screw 2432 shown in FIGS. 121 and 122 includes a break-off head designed to allow such a head to break from a base of the closure at a preselected torque, for example, 70 to 140 inch pounds. The closure structure 2432 includes an outer helically wound guide and advancement structure 2502, a top surface 2504 of the guide and advancement structure, an internal drive 2506, a bottom surface 2508, a point 2509 and a rim 2510. Other than the break-off head, the closure 2432 is substantially the same as, for example, the closure top 210 described above with respect to the assembly 1 and bone screw 25. Located above the guide and advancement structure top surface is a break-off head 2512. As shown in FIG. 99, the closure tops 2432 engage and penetrate the hard rod portion 2425 of the connector 2401.

Figure 117:
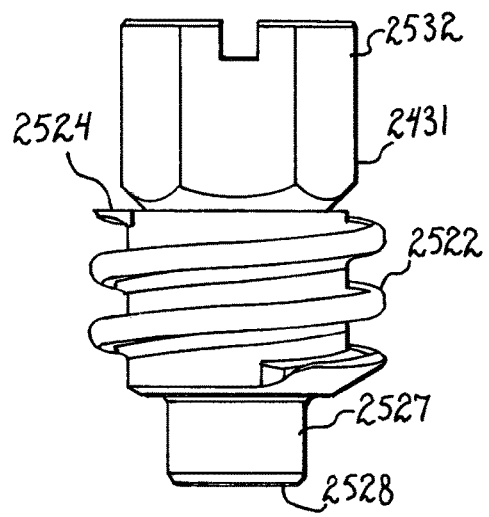
FIG. 117 is an enlarged front elevational view of one of the closure tops shown in FIG. 99.
Figure 118:
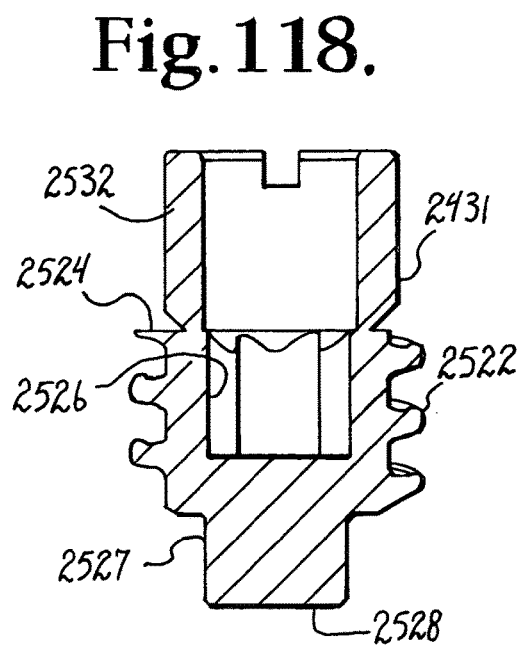

With reference to FIGS. 99 and 117 and 118, also cooperating with the bone anchors 2001 is the closure top 2431 having an outer helically wound guide and advancement structure 2522, a top surface 2524 of the guide and advancement structure, an internal drive 2526 and a break-off head 2532, the same or similar to the respective guide and advancement structure 2502, top surface 2504, internal drive 2506 and break-off head 2512 previously discussed herein with respect to the closure top 2432. In lieu of the point and rim of the closure top 2432, the closure top 2431 has a lower cylindrical portion 2527 having a substantially planar bottom surface 2528. The portion 2527 is sized and shaped to be received by the bore 2441, 2451 or 2461 of respective sleeves 2405, 2406 and 2407, the bottom surface 2528 pressing the cord 2422 into fixed engagement with the sleeve.

Figure 119:
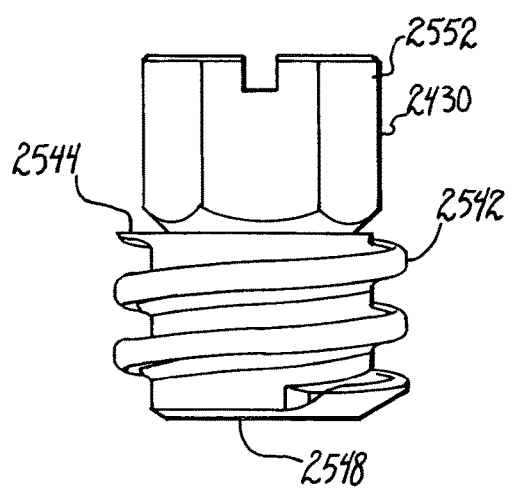
Figure 120:
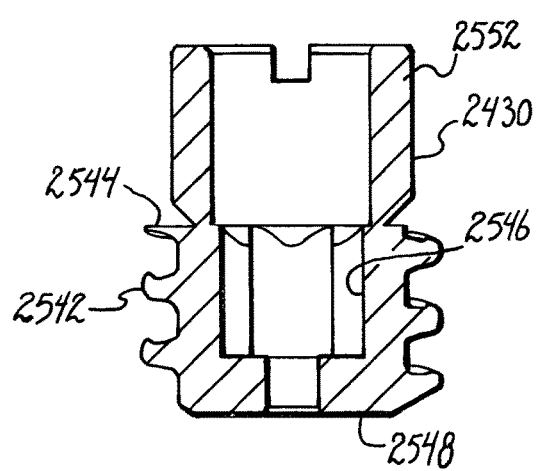
Figure 121:
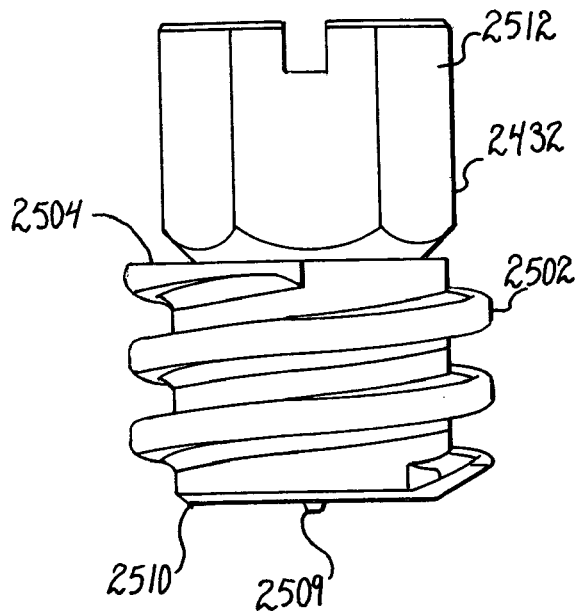
Figure 122:
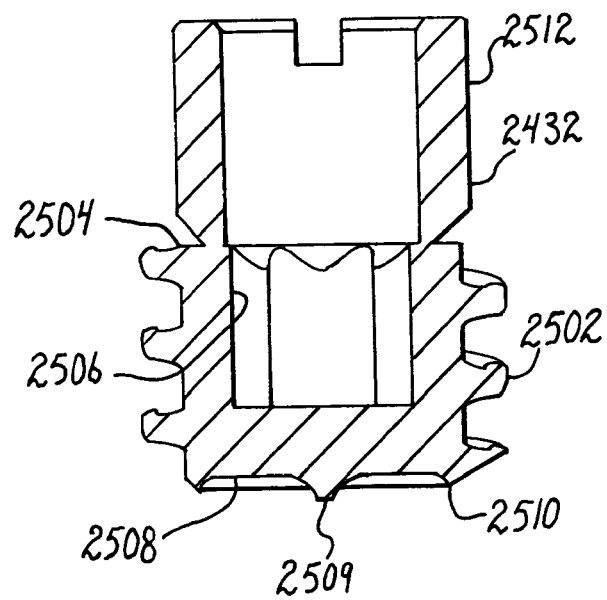

With reference to FIGS. 99 and 119 and 120, also cooperating with the bone anchors 2001 is the closure top 2430 having a an outer helically wound guide and advancement structure 2542, a top surface 2544 of the guide and advancement structure, an internal drive 2546 and a break-off head 2552, the same or similar to the respective guide and advancement structure 2522, top surface 2524, internal drive 2526 and break-off head 2532 previously discussed herein with respect to the closure top 2431. The closure top 2430 includes a planar bottom surface 2548 adjacent the guide and advancement structure 2542. As illustrated in FIGS. 98 and 99, the planar bottom surface 2548 remains flush with a corresponding sleeve surface and does not enter into the bore 2441, 2451 or 2461, allowing sliding movement of the cord 2422 with respect to the bone screw receivers 2010 cooperating with the closure tops 2430.

The assembly 2401 may be assembled as follows: First, after the bone screws 2001 are implanted, the distance between the screws is measured. Thereafter, the spacer/liner combinations 2410 and 2411 are cut to a desired length based upon the measurement made between the bone screws. A tool (not shown), similar to a pipe cutter is usually used to rotate and cut the spacer/liner combination to the desired length at an end opposite the graduated surfaces of the respective spacer. Also at this time, in view of the resulting spacer/liner length, cooperating sleeves 2405 and 2406 of desired sizes are chosen. Because the sleeves are made from a hard material, typically a metal or metal alloy, it is not practical to cut the tube portions thereof to a desired length during the surgical procedure. Therefore, a variety of sleeves 2406 and 2407 are typically provided to end users having at least three different tube portion lengths.

With particular reference to FIG. 97, the cord 2422 is first slid into the coupler 2424 with the end 2494 being placed within the coupler at the threaded end 2481, the cord 2422 being fed therethrough until the knobbed end 2488 of the cord is captured within the coupler recess 2486. The rod 2425 threaded end 2482 may be mated with the coupler thread 2481 at this time or at the very end of the procedure. The cord 2422 is then successively threaded through the connector elements as shown by the arrow G in FIG. 97, some of the components, such as the spacer liner combinations 2410 and 2411 and the blocker/bumper 2418/2417 having been previously assembled. With reference to FIG.

99, as the cord 2422 is threaded into the assembly elements, the spacer/liner combinations 2410 and 2411 and the spacer 2412 are placed into position covering or overlapping tubular portions of the sleeves 2405, 2406 and 2407. The cord 2422 is typically much longer than shown in FIGS. 97 and 99 and then cut to length near the end 2494 after being fully assembled with the remaining elements of the assembly 2401, so that the cord may be grasped and tensioned either before or after the assembly 2401 is fixed to the bone screws 2001. If pre-tensioning is desired, at this time, prior to implanting the assembly, a tensioning tool (not shown) known in the art is used to pull upon and put tension on the cord 2422 near the end 2494. The cord 2422 is preferably tensioned until the bumper compresses and then the set screw 2419 is rotated and driven into the blocker 2418 and up against the cord 2422 using a driving tool (not shown) engaged with an inner drive of the set screw 2419.

The assembly 2401 (either pre-tensioned or in a loosely attached orientation) is implanted by inserting the sleeve body portions into the bone screws 2001 with each receiver 2010 being received between the two flanges of each sleeve. Closure tops 2430 and 2431 are chosen by the surgeon based upon whether a sliding or a gripping relationship is desired with the particular receiver 2010.

With reference to FIG. 99, the final tensioned assembly 2401 is shown that is substantially dynamically loaded and oriented relative to the cooperating vertebra, providing relief (e.g., shock absorption) and protected movement with respect to flexion, extension, distraction and compressive forces placed on the assembly 2401 and the connected bone screws 2001 as well as providing more rigid support at the rod 2425. During complex spinal movements, the spacers 2412, 2413 and 2415 are able to move or flex away from and towards the flanges of the sleeves 2405, 2406 and 407 without compromising the strength and integrity of the assembly 2401. It is noted that a problem encountered with dynamic spinal implant systems is the need to provide adequate support with respect to bending sheer. Most spinal movements are not purely bending movements, e.g., flexion and extension. Most movements include both bending and tension, extension or compression. Such bending shear is not well resisted by a cord and spacer alone that performs well in tension, but not when the tension includes a vector force. The present invention advantageously provides a hard, non-elastic extension of a rigid sliding sleeve body, the extension further located within an optional non-elastic liner of the spacer 2413 or 2415. Such features protect against vector forces while still allowing for advantageous tension of the cord 2422 as well as improved compression provided by the outer bumper 2417. The cord 2422 and the sleeves 2405, 2406 and 2407 allow for some twisting or turning, providing some relief for torsional stresses. Furthermore, the compressed bumper 2417 and the fixed contact between the sleeves and one end of each spacer, as well as the fixed contact between the bumper 2417 and the blocker 2418 places some limits on torsional movement as well as bending movement, to provide spinal support. The cord 2422 (in tension) and bumper 2417 (in compression) allow for compression and some extension of the assembly 2401 located between the two bone screws 2001, e.g., shock absorption. Another advantage of embodiments of the present invention is that because of the inelastic sleeve extension that slides within and is overlapped by the typically elastic spacer located between two bone screws, the resulting assembly 2401 is more stable than a cord and spacer alone, therefore strength of the assembly does not rely solely upon the amount of tension placed upon the cord. Therefore, in embodiments according to the invention, it is not necessary to place as much tension on the cord 2422 as would be required for a more traditional cord and spacer arrangement, thus protecting the cord from damage of over stressing.

If removal of the assembly 2401 from any of the bone screw assemblies 2001 is necessary, or if it is desired to release the assembly 2401 at a particular location, disassembly is accomplished by using the driving tool (not shown) with a driving formation cooperating with internal drives of the closure structures 2430, 2431 and 2432 to rotate and remove such closures from the receivers 2010. Disassembly is then accomplished in reverse order to the procedure described previously herein for assembly.

Eventually, if the spine requires more rigid support, the connecting member assembly 2401 according to the invention may be removed and replaced with another longitudinal connecting member, such as a solid rod or bar, having the same width or diameter as body portions of the sleeves 2405, 2406 and 2407, utilizing the same receivers 2010 and the closure structures 2432. Alternatively, if less support is eventually required, a less rigid, more flexible assembly, for example, an assembly 2401 having spacers and bumpers made of a softer more compressible material than the spacers and bumpers being replaced thereby, also utilizing the same bone screws 2001.

Figure 115:
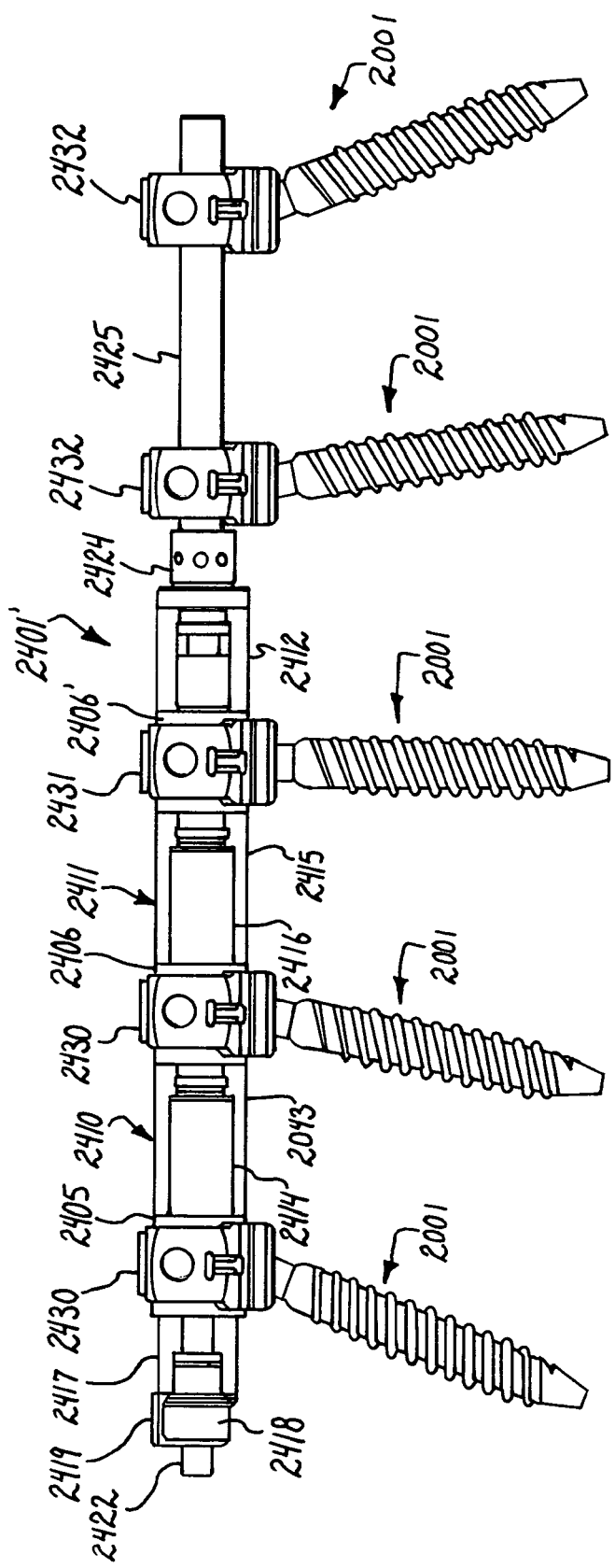
FIG. 115 is a side elevational view of another embodiment of a longitudinal connecting member according to the invention shown attached to five polyaxial bone screws.
Figure 116:
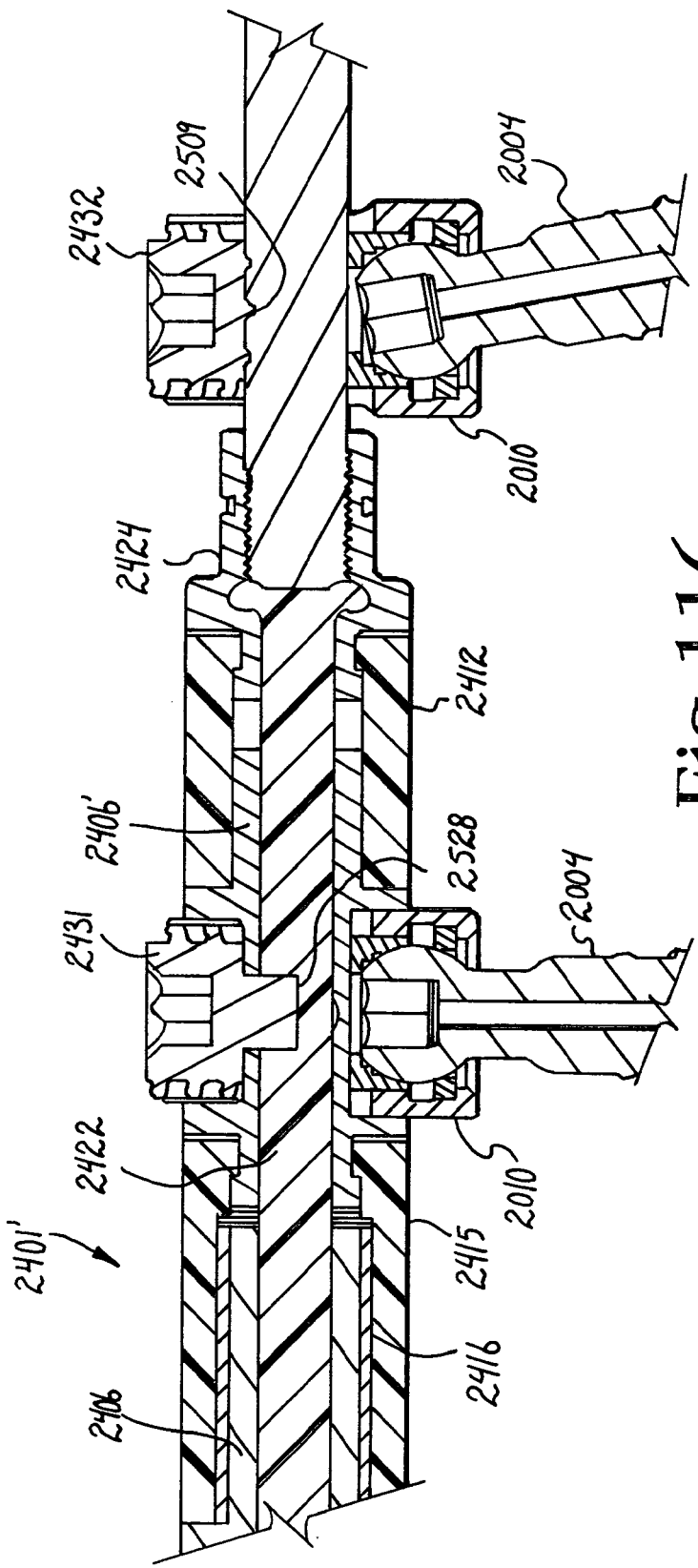
FIG. 116 is an enlarged and partial side elevational view of the connecting member of FIG. 115 with portions broken away to show the detail thereof.

With reference to FIGS. 115-116, an alternative longitudinal connecting member assembly according to the invention, generally 2401' is illustrated wherein the sleeve 2407 is replaced by a sleeve 2406' that is the same as the sleeve 2406 with the exception that the knobbed end portion 2462 that provides a push-on fixed element attachment is replaced by a cylindrical extension slidingly received within the spacer 2412, illustrating one of the many segmental stiffness choices available to a surgeon with assemblies according to the invention.

With reference to FIGS. 123-139 further alternative connecting members according to the invention are shown that include one or more sleeves with cooperating, spacers, bumpers and an inner tensioned cord, such as, for example, the connecting member, generally 3201, shown in FIG. 133. With particular reference to FIGS. 123-131, a bone screw 3001 is illustrated with a hard, inelastic, flanged sleeve, generally 3204 through which a tensioned cord 3206 extends. The cord 3206 is not shown in FIGS. 123-131, but see, for example, FIG. 133, that also illustrates a cooperating cord blocker or fixer 3210 with a cord fixing set screw 3212, an elastic end bumper 3214, and elastic or inelastic spacers 3216 that are each located about the cord 3206 and are disposed between each pair of bone anchors 3001 of the overall assembly 3201. The assembly 3201 is assembled in the same or similar manner as described above with respect to the assemblies 1 and 2401, for example. The tubular bumper 3214 and tubular spacers 3216 shown in FIG. 133 are transparent, allowing for viewing of the sleeves, generally 3204, and the tensioned cord 3206 in FIG. 133. However, it is foreseen that in other embodiments, the spacers 3216 may be made of materials that may not be transparent or translucent. Also as shown in FIG. 133, at least two types of bone screw closures are utilized, either a slide or slipping closure top 3018 or 3018' or a cord gripping closure top 3018". The tops 3018 and 3018' are substantially identical to the closure top 210 previously described herein, with the top 3018' further including a point and rim. The closure top 3018" is similar to the tops 3018 and 3018', but rather than a point and rim, the top 3018' includes a cord penetrating extension 3171. The slide or slip closure tops 3018 and 3018' engage a respective sleeve 3204 but not the cord 3206, allowing the cord to slip or slide within the polyaxial screw 3001. The grip closure top 3018" extends through the sleeve and grips and fixes the cord 3206 with respect to the sleeve and thus fixes the cord in relation to the polyaxial screw 3001. The illustrated extension 3171 penetrates the cord 3206 and extends into a lower aperture of the respective sleeve. Also, tubular extensions of some of the sleeves 3204 extend into and through some of the spacers 3216. Such spacer overlap with respect to the sleeves provides advantageous anti-shear support for the connecting member 3201. A portion of the cord blocker 3210 also extends into a bore of the bumper 3214. The bumper 3214 also extends about the cord 3206 and is typically made from an elastomer while the outer spacers 3216, although typically elastomeric, may be made from a material with a different durometer, typically (but not always) being tougher and less compressible than the material of the bumper 3214. The sleeves 3204 and the spacers 3216 are typically made from a hard, non-elastic material, such as a metal or metal alloy, like cobalt chromium. Flanged portions of the sleeves 3204 are located on either side of the bone screw receivers 3010, the flanges abutting against the spacers 3216 or the bumper 3214, the flanges extending radially outwardly to an extent to fully engage ends of adjacent spacers or the bumper, resulting in a stable, secure, substantially full contact between the individual elements of the assembly 3201. Furthermore, the flanges allow for assembly and dynamic setting of the connector 3201 prior to implantation, if desired, with the cord 3206 being placed in tension and at least the bumper 3214 being placed in compression. In some embodiments of the invention, tensioning of the cord 3216 and compression of the bumper 3214 and optionally the spacers 3216 may be performed after the assembly 3201 is attached to the bone screws 3001.

Figure 129:
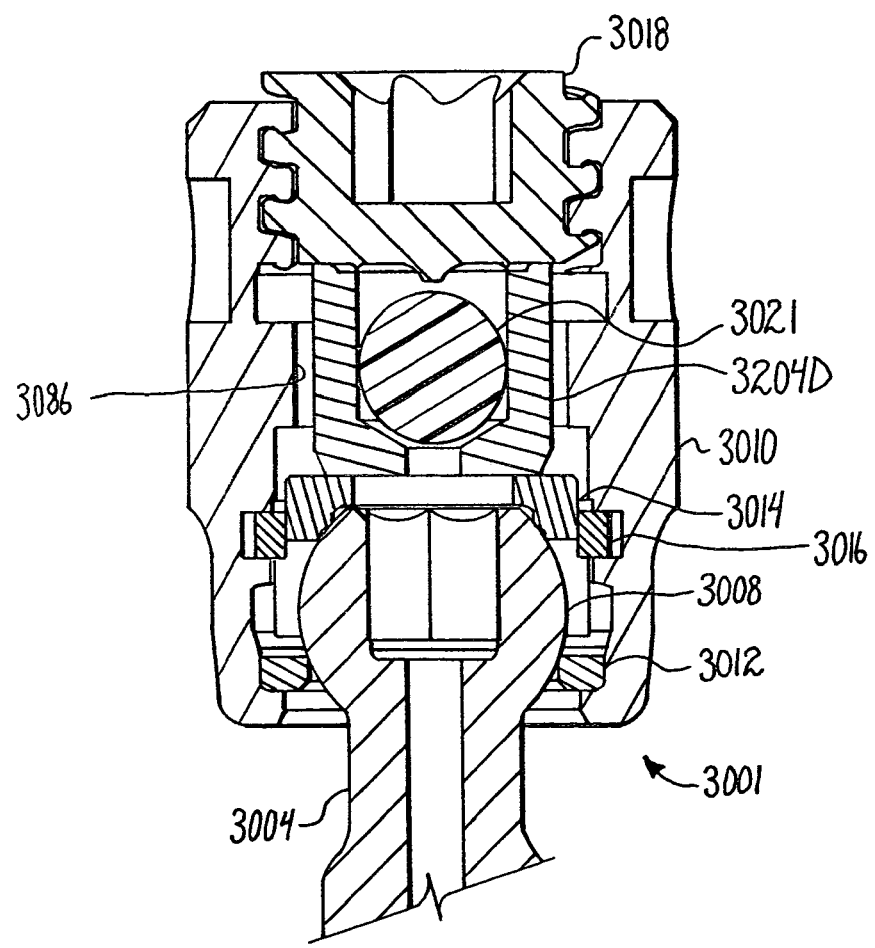

With particular reference to FIGS. 123-129, a bone screw assembly 3001 is illustrated with a particular sleeve 3204D. With reference to FIG. 129, the bone screw 3001 generally includes a shank 3004, a receiver 3010, an open retainer 3012 for capturing a shank upper portion 3008 in the receiver 3010, an insert 3014 having a planar top surface, a spring ring 3016 for holding the insert 3014 during some of the steps of assembly of the bone screw, and shown with the closure top 3018'. Although a particular bone screw is shown, the sleeves 3204 may be utilized with a variety of bone screws, particularly those with inserts such as the insert 3014 having a low profile with either a planar top surface (or a slightly recessed surface), providing adequate space within the receiver for receiving both the insert 3014 at a lower portion thereof and one sleeve 3204 at an upper portion thereof, allowing for a larger or more substantial sleeve than, for example, bone screws having an insert with a U-shaped recess and arm portions that extend upwardly on either side of the sleeve wherein the insert arms and/or the sleeve would both be required to be relatively narrow or thin to both fit between the receiver arms.

Sleeves 3204 of the invention are provided with or without tubular extensions, on one or both sides thereof, and with different lengths of tubular extensions, as best shown in FIG. 132. Thus, each different sleeve 3204 configuration has been further identified with a letter to indicate the type of extension, with FIG. 132 illustrating sleeves 3204A through 3204L. FIG. 132 also illustrates a sleeve 3204M that is a rod/cord coupler and is further illustrated in FIGS. 134-136 and will be described in greater detail below.

The sleeves 3204A-33204F are identical with the exception of the presence or length of one or more tubular extension. Therefore, the sleeve 3204D will be the only sleeve of this group discussed in detail herein with particular reference to FIGS. 123-129.

The sleeve 3204D further includes a body portion 3234 generally sized and shaped for being received within the polyaxial bone screw 3001 receiver 3010 and a pair of opposed tubular extensions 3235 sized and shaped to be slidingly received within the spacer 3216 and over the cord 3206. The illustrated body portion 3234 and tubular extensions 3235 are integral or otherwise fixed to one another. A through bore 3236 extends centrally through the body portion 3234 and centrally through the tubular extensions 3235. The bore 3236 is sized and shaped to slidingly receive the cord 3206. The body portion 3234 further includes a pair of spaced radially extending flanges 3237 and 3238 with a partially cylindrical and partially planar body portion being located therebetween, the body portion having a slightly enlarged or protruding portion or portions illustrated as opposed partially cylindrical and partially planar extensions 3239, sized and shaped to closely fit within the cylindrical inner arm surfaces of the bone screw receiver 3010. The portions 3239 function to center the sleeve within the bone screw receiver 3010 and also advantageously strengthen the sleeve, resulting in better load transfer. It is foreseen that in some embodiments of the invention, the body 3234 with centering structure 3239 may be configured to also extend down into the receiver and abut the bone screw shank upper portion 3008 and thus eliminate the compression insert 3014. Furthermore, in some embodiments, the flanges 3237 and 3238 may be reduced or eliminated as the centering of the sleeve with respect to the bone screw receiver 3010 may be performed by the portion or portions 3239.

In the illustrated embodiment, the flanges 3237 and 3238 are substantially cylindrical having opposed planar and annular side surfaces spaced for closely receiving the bone screw 3001 receiver 3010. The illustrated flanges 3237 and 3238 include a lower cut-out, allowing for a close fit between inner flange surfaces 3240 and the planar receiver base surfaces 3069. The body portion 3239 may be sized and shaped to be receivable within and frictionally fixed to a variety of monoaxial or polyaxial screw heads or receivers, including the receiver 3010. A bore 3241 is formed in the body 3234 between the flanges 3237 and 3238, the bore 3241 transverse to and communicating with the through bore 3236. The bore 3241 is sized and shaped to receive the closure top 3018" therein for frictionally gripping the cord 3206, the extension 3171 penetrating the cord 3206 and extending near or into an aperture 32418 located in the sleeve opposite the opening of the bore 3241 and thus placing the cord 3206 in fixed relation with the bone screw receiver 3010, if desired.

The sleeves generally 3204, as well as the cord blocker 3210 with set screw 3212 may be made from a variety of inelastic materials, including, but not limited to metals, metal alloys, including cobalt chromium, and inelastic plastics including, but not limited to plastic polymers such as polyetheretherketone (PEEK), ultra-high-molecular weight-polyethylene (UHMWP), polyurethanes and composites, including composites containing carbon fiber and layers of different materials.

With reference to FIGS. 130-132, lordotic sleeves 3204G-3204L are also shown. The sleeves 3204G-3204L are identical to the sleeves 3204A-3204F, respectively, with the exception that flanges 3237' and 3238' are provided that slope at an angle, inwardly towards the bone screw receiver 3010 as best shown in FIG. 131 (that illustrates the use of the sleeve 3204J) and also in the assembly 3201 shown in FIG. 133 that illustrates the use of a plurality of lordotic sleeves.

With reference to FIG. 132 and FIGS. 134-136, the sleeve and rod/cord coupler 3204M includes a sleeve body portion 3234', one tubular extension 3235', a single flange 3238" and a partial through bore 3236' substantially similar to the respective sleeve body 3234, tubular extensions 3235, flanges 3238 and through bore 3236 of the other sleeves 3204A-3204F. At an end opposed to the tubular extension 3235', the body portion 3234' is integral with an elongate solid rod portion 3250. Also, formed in the body portion 3234' is an aperture or through bore 3251 transverse to and communicating with the bore 3236', the through bore 3251 sized and shaped to closely receive a cord holding pin 3252. The pin 3252, if used, extends completely through the cord 3206, independently fixing the cord 3206 to the sleeve 3204M. Alternatively, in some embodiments of the invention, the pin 3252 is not used and a closure top 3018" may be inserted within a bore 3241' of the sleeve/coupler 3204M to fix the cord 3206 to the sleeve 3204M. In the illustrated embodiment, the bores 3241' and 3251 are substantially parallel to one another. The rod portion 3250 may be provided in a variety of lengths (or cut to length) to cooperate with one or more bone screws to provide a rigid support end to a dynamic assembly, such as the assembly 3201 shown in FIG. 133.

With reference to FIGS. 137-139, a set of alternative sleeves, generally 3304, are shown that are substantially similar to the sleeves 3204 previously described herein, with the exception of surface features 3345 that allows for a press or friction fit with the receiver 3010. Therefore, the sleeves 3304 each include a sleeve body 3334, two, one or no tubular extensions 3335, a through bore 3336, a pair of flanges 3337 and 3338, a partially cylindrical body portion 3339, inner flange surfaces 3340 and a vertical bore 3341 that are the same or similar to the respective sleeve body 3234, tubular extensions 3235, through bore 3236, pair of flanges 3237 and 3238, partially cylindrical body portion 3239, inner flange surfaces 3240 and vertical bore 3241 of the sleeves, generally 3204 previously described herein. The pair of opposed press fit surface features 3345 are located on either side of the cylindrical portion 3339 and in operation are disposed between the receiver arms at or near a run-out of the guide and advancement structure for the closure top and a discontinuous cylindrical surface 3086. As the sleeve 3304 is pressed downwardly toward the receiver base, the surfaces 3345 engage the surface 3086, providing a snug, but adjustable fit between the sleeve 3304 and the receiver arms.

With reference to FIGS. 140-154 a polyaxial bone screw 4001 that does not include a pressure insert is shown being used in a connecting member 4201 that includes another embodiment of a sleeve, generally 4204, according the invention. The connecting member 4201 includes one or more sleeves, generally 4204 with cooperating, spacers, bumpers and an inner tensioned cord, such as, for example, shown in FIG. 154. The illustrated bone screw 4001 generally includes a shank 4004, an open retainer 4012, a receiver 4010 and is shown in FIG. 140 with a slip or slide closure top 4018 and a gripping closure top 4018' as well as one of the sleeves 4204. The sleeves 4204 are hard, inelastic and flanged, through which a tensioned cord 4206 extends as shown in FIG. 154. FIG. 154 also illustrates a cooperating cord blocker or fixer 4210 with a cord fixing set screw 4212, an elastic end bumper 4214, and elastic or inelastic spacers 4216 that are each located about the cord 4206 and are disposed between each pair of bone anchors 4001 of the overall assembly 4201. The tubular bumper 4214 and tubular spacers 4216 shown in FIG. 154 are transparent, allowing for viewing of the sleeves, generally 4204, and the tensioned cord 4206 in FIG. 154. However, it is foreseen that in other embodiments, the spacers 4216 may be made of materials that may not be transparent or translucent. Also as shown in FIG. 154, two types of bone screw closures are utilized, either the slide or slipping closure top 4018 previously described herein (e.g., closure 2432 of the assembly 2401 or closure 3018' of the assembly 3201) or a cord gripping closure top 4018' similar to the top 2431 of the assembly 2401. The slide or slip closure top 4018 engages a respective sleeve 4204 but not the cord 4206, allowing the cord to slip or slide within the polyaxial screw 4001. The grip closure top 4018' extends through the sleeve and grips and fixes the cord 40206 against a surface of the sleeve and thus fixes the cord in relation to the polyaxial screw 4001. Tubular extensions of some of the sleeves 4204 may extend into and through some of the spacers 4216. Such spacer overlap with respect to the sleeves provides advantageous anti-shear support for the connecting member 4201. A portion of the cord blocker 4210 also extends into a bore of the bumper 4214. The bumper 4214 also extends about the cord 4206 and is typically made from an elastomer while the outer spacers 4216, although typically elastomeric, may be made from a material with a different durometer, typically (but not always) being tougher and less compressible than the material of the bumper 4214. The sleeves 4204 and the spacers 4216 are typically made from a hard, non-elastic material, such as a metal or metal alloy, like cobalt chromium. Flanged portions of the sleeves 4204 are located on either side of the bone screw receivers 4010, the flanges abutting against the spacers 4216 or the bumper 4214, the flanges extending radially outwardly to an extent to fully engage ends of adjacent spacers or the bumper, resulting in a stable, secure, substantially full contact between the individual elements of the assembly 4201. Furthermore, the flanges allow for assembly and dynamic setting of the connector 4201 prior to implantation, if desired, with the cord 4206 being placed in tension and at least the bumper 4214 being placed in compression. In some embodiments of the invention, tensioning of the cord 4216 and compression of the bumper 4214 and optionally the spacers 4216 may be performed after the assembly 4201 is attached to the bone screws 4001.

With particular reference to FIG. 141, three different types of sleeves 4204, shown without tubular extensions, are illustrated. They are a parallel flanged sleeve 4204A, an angled or lordotic sleeve 4204B and a transition sleeve 4204C that includes a rod/cord coupler. As stated above, sleeves 4204 of the invention may be provided with or without tubular extensions, on one or both sides thereof, and with different lengths of tubular extensions, as best shown in FIG. 154. The sleeves 4204A shown in FIG. 154 may include an extension 4800 on one side thereof, pairs of substantially identical extensions 4810 or 4820, or for example, opposing extensions 4830 and 4831 of different lengths, to name a few. The illustrated sleeve with rod/cord coupler 4204C also includes a tubular extension 4840.

With particular reference to FIGS. 142-147, the bone screw assembly 4001 is illustrated with the sleeve 4204A. The sleeve 4204A further includes a body portion 4234 generally sized and shaped for being received within the polyaxial bone screw 4001 receiver 4010 and about the cord 4206. A through bore 4236 extends centrally through the body portion 4234, the bore 4236 being sized and shaped to slidingly receive the cord 4206. The body portion 4234 further includes a pair of spaced radially extending flanges 4237 and 4238 with a partially cylindrical and partially planar body portion being located therebetween, the body portion having a slightly enlarged or protruding portion or portions illustrated as opposed faceted or partially cylindrical and partially planar extensions 4239, sized and shaped to closely fit within the cylindrical inner arm surfaces of the bone screw receiver 4010. The portions 4239 function to center the sleeve within the bone screw receiver 4010 and also advantageously strengthen the sleeve, resulting in better load transfer. The body 4234 with centering structure 4239 further includes a bottom surface 4240 having a roughened or as illustrated, textured surface with ridges or points 4241 configured to abut against, engage and penetrate the domed surface 4040 of the shank upper portion 4008 as best shown in FIG. 146. The surface portion 4241 may also be cupped or radiused without spikes or ridges.

It is foreseen that in some embodiments, the flanges 4237 and 4238 may be reduced or eliminated as the centering of the sleeve with respect to the bone screw receiver 4010 may be performed by the portion or portions 4239. In the illustrated embodiment, the flanges 4237 and 4238 are substantially cylindrical having opposed planar and annular side surfaces 4242 spaced for closely receiving the bone screw 4001 receiver 4010. The illustrated flanges 4237 and 4238 include a lower cut-out, allowing for a close fit between inner flange surfaces 4242 and the receiver base surfaces. The body portion 4239 may be sized and shaped to be receivable within and frictionally fixed to a variety of monoaxial or polyaxial screw heads or receivers, including the receiver 4010. The body portion 4239 may also be configured to provide a lock and release feature as previously discussed herein with respect to the sleeves 3304 shown in FIG. 137, for example. A bore 4243 is formed in the body 4234 between the flanges 4237 and 4238, the bore 4243 transverse to and communicating with the through bore 4236. The bore 4243 is sized and shaped to receive the closure top 4018 or 4018' therein. As illustrated in FIG. 147, the closure top 4018' is inserted in the sleeve 4204A with the extension 4169' extending into the sleeve 4204A for frictionally gripping a cord 4206 (not shown) against an internal surface defining the through bore 4236, and thus placing such cord 4206 in fixed relation with the bone screw receiver 4010, if desired.

The sleeves, generally 4204, as well as the cord blocker 4210 with set screw 4212 may be made from a variety of inelastic materials, including, but not limited to metals, metal alloys, including cobalt chromium, and inelastic plastics including, but not limited to plastic polymers such as polyetheretherketone (PEEK), ultra-high-molecular weight-polyethylene (UHMWP), polyurethanes and composites, including composites containing carbon fiber and layers of different materials.

With reference to FIGS. 141 and 148-150, the lordotic sleeve 4204B is illustrated. The sleeve 4204B is identical to the sleeve 4204A with the exception that flanges 4237' and 4238' are provided that slope at an angle, inwardly towards the bone screw receiver 4010 as best shown in FIG. 148.

With reference to FIG. 141 and FIGS. 151-153, the sleeve and rod/cord coupler 4204C includes a sleeve body portion 4234", a single flange 4238" and a partial through bore 4236" substantially similar to the respective sleeve body 4234, flange 4238 and through bore 4236 of the sleeve 4204A. At an end opposed to the flange 4238", the body portion 4234" is integral with an elongate solid rod portion 4250. Also, formed in the body portion 4234" is an aperture or through bore 4251 transverse to and communicating with the bore 4236", the through bore 4251 sized and shaped to closely receive a cord holding pin 4252. The pin 4252, if used, extends completely through the cord 4206, independently fixing the cord 4206 to the sleeve 4204C. Alternatively, in some embodiments of the invention, the pin 4252 is not used and a closure top 4018' may be inserted within a bore 4243" of the sleeve/coupler 4204C to fix the cord 4206 to the sleeve 4204C. In the illustrated embodiment, the bores 4243" and 4251 are substantially parallel to one another. The rod portion 4250 may be provided in a variety of lengths (or cut to length) to cooperate with one or more bone screws to provide a rigid support end to a dynamic assembly, such as the assembly 4201 shown in FIG. 154.

It is to be understood that while certain forms of the present invention have been illustrated and described herein, it is not to be limited to the specific forms or arrangement of parts described and shown.

What is claimed and desired to be secured by Letters Patent is as follows:

1. A medical implant assembly for insertion into a spine of a patient, the medical implant assembly comprising:
    a rigid end structure configured to be secured to a first bone anchor;
    a flanged sleeve having a through-bore, the flanged sleeve configured to be secured to a second bone anchor and having a flanged portion extending outside of a receiver of the second bone anchor when the flanged sleeve is secured to the second bone anchor;
    a tensionable cord having a first end portion and a second end portion opposite the first end portion, the tensionable cord configured to extend through the through-bore of the flanged sleeve, the first end portion of the tensionable cord being fixedly connected to the rigid end structure;
    a compressible spacer having a spacer through-bore, the tensionable cord configured to extend through the spacer through-bore, the compressible spacer configured to be positioned on the tensionable cord between the rigid end structure and flanged sleeve so as to engage the flanged portion of the flanged sleeve;
    an outer end blocker having a blocker through-bore and a threaded closed bore intersecting the blocker through-bore for releasably engaging a set screw, the outer end blocker having opposite laterally facing side surfaces that are planar and parallel with respect to each other, the side surfaces being parallel to both a first longitudinal axis extending through the blocker through-bore and a second longitudinal axis extending through the threaded closed bore, and the second end portion of the tensionable cord configured to extend through the blocker through-bore;
    a bumper configured to be disposed between the flanged sleeve and the outer end blocker and configured to engage and at least partially overlap with the outer end blocker; and
    a set screw configured to be releasably engaged to the outer end blocker via the threaded closed bore and compressible against the tensionable cord;
    wherein the tensionable cord is configured to be tensioned from the second end portion of the tensionable cord adjacent the outer end blocker, and the tensionable cord is configured to be secured to the outer end blocker by the set screw after the tensionable cord is tensioned, thereby releasably holding the tensionable cord in tension and the bumper in compression,
    wherein the flanged sleeve is configured to be in slidable relation with the tensionable cord after tensioning of the tensionable cord and when the flanged sleeve is secured to the receiver of the second bone anchor, wherein the tensionable cord is configured to be retensioned from the second end portion adjacent the outer end blocker after being inserted into the spine of the patient, and wherein the planar and parallel side surfaces of the outer end blocker are configured to be engaged by a lower end portion of a counter-torque tool while the set screw is being compressed against the tensionable cord within the outer end blocker after the tensionable cord is tensioned and/or retensioned.

2. The medical implant assembly of claim 1, wherein the rigid end structure is a connector, a sleeve, or a rod.

3. The medical implant assembly of claim 1, wherein the compressible spacer is configured to engage the rigid end structure on one end and the flanged sleeve on the opposite end.

4. The medical implant assembly of claim 1, wherein the outer end blocker comprises a body portion and a tubular extension, the body portion and the tubular extension defining the blocker through-bore through which the tensionable cord is configured to extend.

5. The medical implant assembly of claim 4, wherein the tubular extension of the outer end blocker is configured to engage in a frictional fit with a bore of the bumper.

6. The medical implant assembly of claim 1, wherein the tensionable cord is configured to extend through the spacer through-bore between the first bone anchor and the second bone anchor to maintain a minimum distance between the first bone anchor and the second bone anchor.

7. The medical implant assembly of claim 1, further comprising:
the first bone anchor comprising a first receiver, a first fixation portion, and a first closure, the first closure configured to engage the first receiver to fixably retain the rigid end structure within the first receiver while fixably coupling the tensionable cord to the rigid end structure;
the second bone anchor comprising a second receiver, a second fixation portion, and a second closure, the second closure configured to engage the second receiver to fixably retain the flanged sleeve within the second receiver while allowing the tensionable cord to slide within the through-bore of the flanged sleeve.

8. The medical implant assembly of claim 7, wherein the compressible spacer is configured to be positioned between the first receiver and the second receiver so as to maintain a minimum distance between the first receiver and the second receiver; and
the flanged sleeve comprises a body portion and a tubular extension flanged portion, the body portion and the tubular extension flanged portion of the flanged sleeve defining the through-bore of the flanged sleeve through which the tensionable cord is configured to extend, the tubular extension flanged portion of the flanged sleeve configured to be slidingly received within the spacer through-bore of the compressible spacer.

9. The medical implant assembly of claim 8, wherein the rigid end structure comprises a body portion and a tubular extension, the body portion and the tubular extension of the rigid end structure defining a through-bore of the rigid end structure through which the tensionable cord is configured to extend, the tubular extension of the rigid end structure configured to provide a frictional fit with the spacer through-bore of the compressible spacer.

10. The medical implant assembly of claim 9, wherein the tubular extension of the rigid end structure is shorter than the tubular extension of the flanged sleeve.

11. The medical implant assembly of claim 7, wherein the first receiver includes a threaded engagement structure, the first closure having a threaded engagement structure configured to engage the threaded engagement structure of the first receiver to fixably retain the rigid end structure within the first receiver, the first closure further comprising an extension configured to fixably couple the tensionable cord to the rigid end structure through an aperture in the rigid end structure;
the second receiver includes a threaded engagement structure, the second closure having a threaded engagement structure configured to engage the threaded engagement structure of the second receiver to fixably retain the flanged sleeve within the second receiver.

12. The medical implant assembly of claim 7, further comprising:
a third bone anchor comprising a third receiver and a third fixation portion, the third fixation portion configured to be affixed to a vertebra of the spine of the patient between the first bone anchor and the second bone anchor, the third receiver configured to be slidably coupled to the tensionable cord.

13. The medical implant assembly of claim 1, wherein the compressible spacer comprises:
a first annular surface at a first end of the spacer through-bore of the compressible spacer configured to abut a surface of the rigid end structure; and
a second annular surface at a second end of the spacer through-bore of the compressible spacer opposite the first end of the spacer through-bore configured to abut a surface of the flanged sleeve.

14. The medical implant assembly of claim 1, wherein the side surfaces of the outer end blocker are configured to be held with the counter-torque tool to prevent rotation of the outer end blocker as the set screw is tightened.

15. The medical implant assembly of claim 14, wherein the side surfaces extend above a U-shaped lower surface on the outer end blocker.

16. The medical implant assembly of claim 15, wherein the U-shaped lower surface includes a partial cylindrical surface.

17. The medical implant assembly of claim 1, wherein the tensionable cord is configured to be tensioned before being inserted into the spine of the patient from the second end portion adjacent the outer end blocker.

18. The medical implant assembly of claim 17, wherein the tensionable cord is configured to be retensioned before being inserted into the spine of the patient from the second end portion adjacent the outer end blocker.

19. The medical implant assembly of claim 1, wherein the tensionable cord is configured to be tensioned after being inserted into the spine of the patient from the second end portion adjacent the outer end blocker.

20. The medical implant assembly of claim 1, wherein the set screw is configured to compressively engage the tensionable cord after being tensioned in the blocker through-bore without penetration into the tensionable cord.

21. The medical implant assembly of claim 1, wherein the set screw is configured to compressively engage the tensionable cord after being tensioned in the blocker through-bore with penetration into the tensionable cord.

22. The medical implant assembly of claim 1, wherein the flanged sleeve is configured to rotate within the receiver prior to being secured to the second bone anchor.

23. The medical implant assembly of claim 1, wherein the flanged sleeve is configured to not rotate after being positioned within the receiver of the second bone anchor.

24. The medical implant assembly of claim 1, wherein the threaded closed bore is perpendicular to the blocker through-bore.

* * * * *